(12) United States Patent
Maynard et al.

(10) Patent No.: US 9,925,270 B2
(45) Date of Patent: Mar. 27, 2018

(54) BFGF-POLYMER CONJUGATES, METHODS FOR MAKING THE SAME AND APPLICATIONS THEREOF

(71) Applicant: The Regents of the University of California, Oakland, CA (US)

(72) Inventors: Heather D. Maynard, Los Angeles, CA (US); Thi Nguyen, Reseda, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 182 days.

(21) Appl. No.: 14/361,167

(22) PCT Filed: Nov. 28, 2012

(86) PCT No.: PCT/US2012/066905
§ 371 (c)(1),
(2) Date: May 28, 2014

(87) PCT Pub. No.: WO2013/082196
PCT Pub. Date: Jun. 6, 2013

(65) Prior Publication Data
US 2014/0335045 A1    Nov. 13, 2014

Related U.S. Application Data

(60) Provisional application No. 61/564,250, filed on Nov. 28, 2011.

(51) Int. Cl.
*A61K 47/48* (2006.01)
*A61K 38/18* (2006.01)
*A61K 31/795* (2006.01)

(52) U.S. Cl.
CPC ...... *A61K 47/48176* (2013.01); *A61K 31/795* (2013.01); *A61K 38/1825* (2013.01)

(58) Field of Classification Search
CPC .............. A61K 31/795; A61K 38/1825; A61K 47/48176
See application file for complete search history.

(56) References Cited

FOREIGN PATENT DOCUMENTS

EP    WO 2009/135888    * 11/2009    ............ A61K 47/48

OTHER PUBLICATIONS

Benezra et al. (Antiproliferative Activity of Heparin Mimetics vol. 14, No. 12, Dec. 1994 p. 1992-1999).*
Christman et al. (J. Am. Chem. Soc. 2008, 130 16585-16591).*
International Search Report and Written Opinion dated Mar. 8, 2013 in connection with PCT/US2012/06695.
Sangaj, N. et al. "Hepar in mimicking polymer pormotes myogenic differentiation of muscle progenitor cells", Biomacromolecules, 2010, vol. 11, pp. 3294-3300.
Christman, K. L. et al. Nanoscale growth factor patterns by immobilization on a heparin mimicking polymer J. Am. Chem. Soc., 2008, vol. 130, No. 49, pp. 16585-16591.
Rouet, V. et al. "Heparin-like synthetic polymers, named RGTAs, mimic biological effects of heparin in vitro" J. Biomed. Mater. Res. A., 2006, vol. 78, No. 4, pp. 792-797.
Liekens, S. et al. Modulation of fibroblast growth factor-2 receptor binding, signaling, and mitogenic activity by heparin-mimicking polysulfonated compounds Mol. Pharmacol., 1999, vol. 56, No. 11, pp. 204-2213.
Benezra, M. et al. Antiprolierative activity to vascular smooth muscle cells and receptor binding heparin-mimicking polyaromatic anionic compounds, Arterioscler. Tromb. Vasc. Biol., 1994, vol. 14, pp. 1998 and 1999.

* cited by examiner

*Primary Examiner* — Anna Falkowitz
(74) *Attorney, Agent, or Firm* — Quarles & Brady, LLP

(57) ABSTRACT

A heparin mimicking polymer, its conjugate with bFGF, and method of making and using the same are disclosed. In particular, described herein are conjugates of biologic agents (e.g., bFGF) and heparin mimicking polymers having superior stability while retaining full native activity after a variety of stressors.

12 Claims, 36 Drawing Sheets

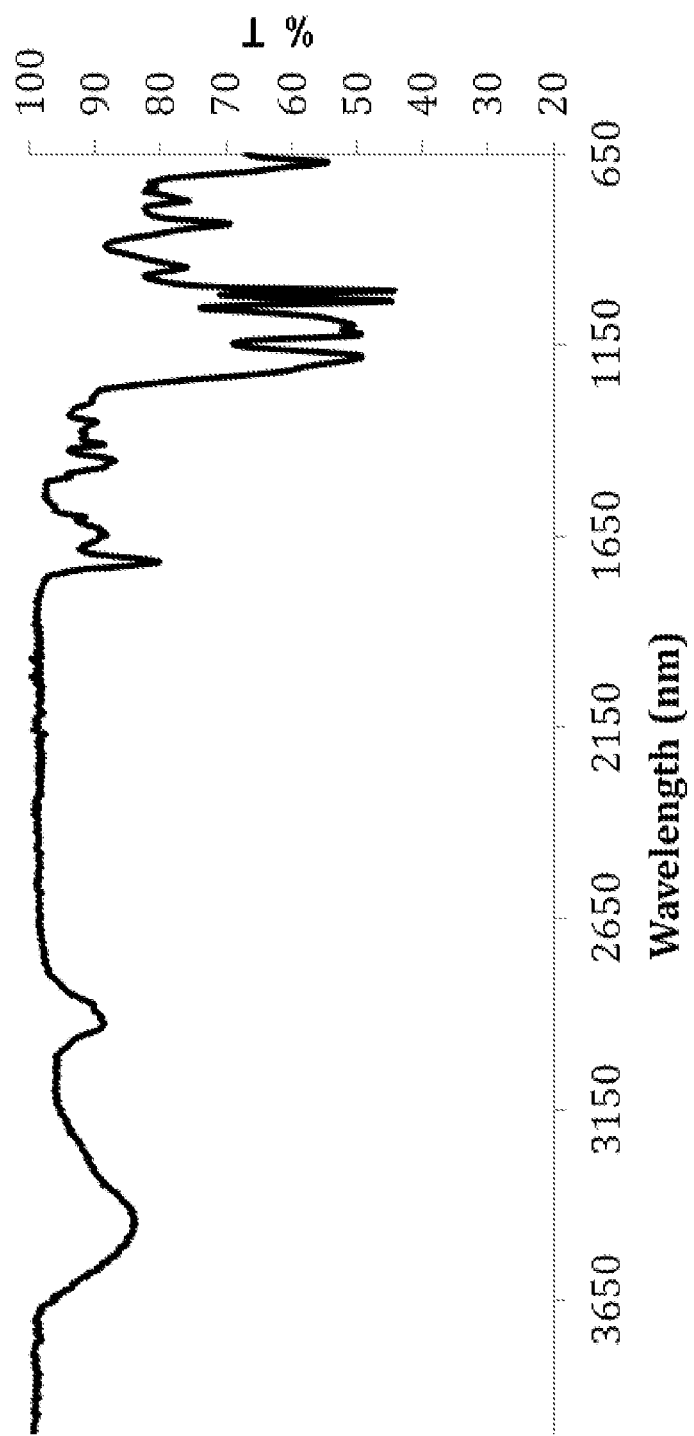

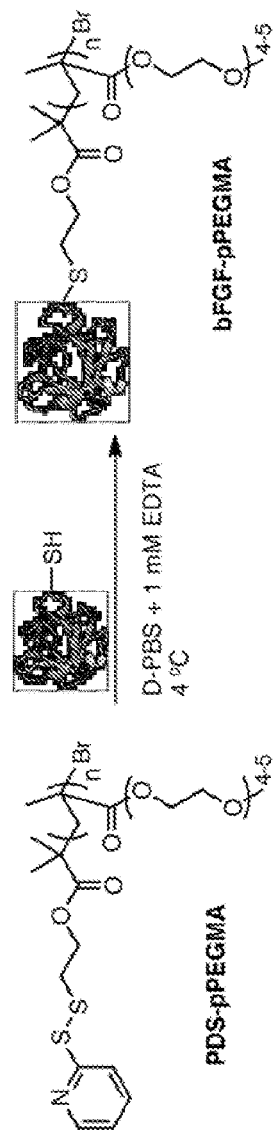
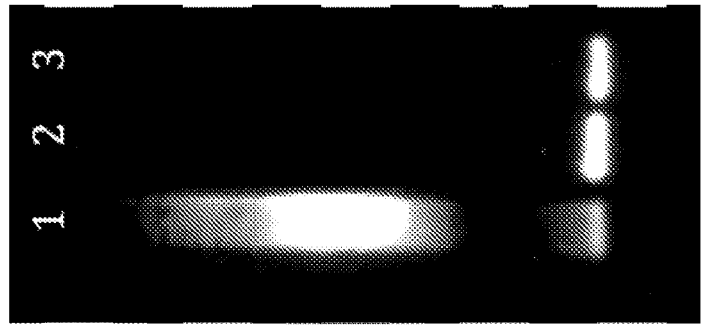
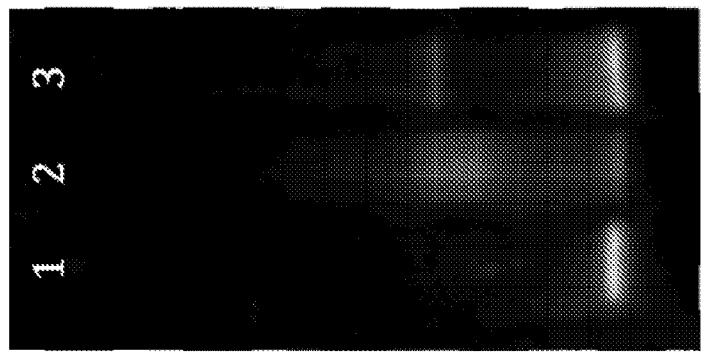
Figure 8A
Figure 8B
Figure 8C

| | Conc. (μg/ml) | Total V collected (ml) | Total m collected (μg) | % bFGF in 2M NaCl fraction | %yield |
|---|---|---|---|---|---|
| Flow through fraction | 6.00E-05 | 0.055 | 3.30E-06 | | |
| Wash 0M NaCl fraction | 7.19E-03 | 0.050 | 3.60E-04 | | |
| Wash 0.5M NaCl fraction | 0.21 | 0.055 | 1.17E-02 | | |
| Elution 2M NaCl fraction | 27.98 | 0.057 | 1.59 | 99.3 | 49.5 |
| bFGF used for conjugation | 16.11 | 0.200 | 3.22 | | |

Scheme 2

Scheme 4

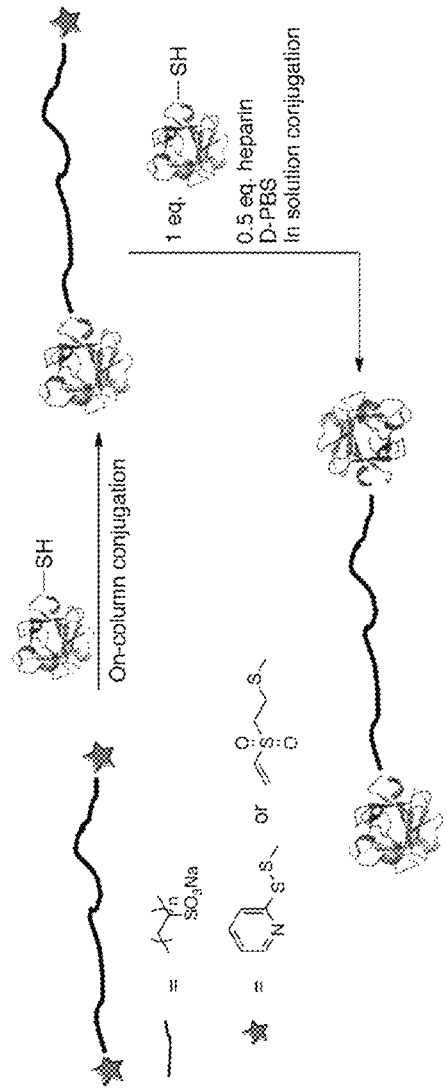

BFGF-POLYMER CONJUGATES, METHODS FOR MAKING THE SAME AND APPLICATIONS THEREOF

CROSS-REFERENCE TO RELATED APPLICATIONS

This application represents the national stage entry of PCT International Application No. PCT/US2012/066905 filed on Nov. 28, 2012, which claims priority from U.S. Provisional Application No. 61/564,250, filed on Nov. 28, 2011, the disclosures of which are hereby incorporated by reference herein in their entirety for all purposes.

STATEMENT REGARDING FEDERALLY-SPONSORED RESEARCH

This invention was made with U.S. Government support on behalf of National Science Foundation (Grant No. CHE-0809832) and the National Institutes of Health (Grant No. R01 EB136774 and No. R01 GM103479). The U.S. Government has certain rights in this invention.

FIELD OF THE INVENTION

The present invention generally relates to biopolymer conjugates with a biologic agent and methods of making and using the same.

BACKGROUND OF THE INVENTION

Basic fibroblast growth factor (bFGF) is unstable and rapidly degrades upon storage and during delivery, which hinders its therapeutic applications. Heparin has been shown to protect bFGF from denaturation by heat and acid, and also to prolong its half-life. Thus, the polysaccharide has been used in controlled release systems of bFGF. However, heparin is difficult to modify and exhibits batch-to-batch variability. It also has significant bioactivity in other, non-target biological pathways. It is known that sulfated and sulfonated small molecules and polymers are capable of mimicking heparin and these have been explored for stabilization of the protein. An important consideration when utilizing such polymers is that high doses of heparin (and heparin-mimicking compounds) have biological effects such as bleeding complications due to anticoagulant activity and anti-angiogenic activity. This activity would be particularly deleterious for therapeutic applications. Covalently binding a heparin-mimicking polymer to bFGF would ensure that a therapeutically useful concentration of the polymer is employed. Despite this advantage, conjugates of heparin mimicking polymers and bFGF have not yet been prepared.

bFGF has been conjugated to other proteins and peptides, but not for the purpose of increasing stability. A histidine-tagged bFGF-8b (related to bFGF) has been non-covalently conjugated to a nitriloacetic acid (NTA) Ni2+ modified poly(acrylamide), but this complex is non-covalent, requires the use of a toxic metal, and was found to be less active than bFGF. PEG-polyanions (pentosan polysulfate and dextran sulfate) have also been utilized to increase stability of a related protein keratinocyte growth factor-2 (KGF-2), but these complexes are also non-covalent. Non-covalent conjugates are likely not to be useful in vivo because of the likelihood of detachment of the polymer upon dilution before reaching target sites. Covalent conjugates of poly (ethylene glycol) (PEG) and bFGF have been synthesized, but these either exhibit significant reductions in protein activity and require addition of heparin to stabilize the conjugate or large concentrations of the conjugate need to be utilized. This invention describes the first conjugate between bFGF and a heparin-mimicking polymer. The conjugate not only retains bioactivity, but is stable to environmental and therapeutically relevant stressors including storage, heat, enzymes, and reduced pH.

SUMMARY OF THE INVENTION

In one aspect, provided herein is a heparin mimicking polymer comprising a reactive group that reacts with a moiety in a target protein causing a covalent attachment of the heparin mimicking polymer to the target protein.

In some embodiments, the heparin mimicking polymer also interacts with a receptor of the target protein, thereby strengthening the interaction between the target protein and receptor. In these embodiments, the heparin mimicking polymer binds to the target protein only, the receptor only, or to both the target protein and the receptor.

In some embodiments, heparin mimicking polymer interacts with the receptor via an electrostatic, hydrophobic, or van der waals interaction.

In some embodiments, the interaction between the target protein and receptor is between a dimer of the target protein and a dimer of the receptor. In some embodiments, the interaction between the target protein and receptor is between a multimer of the target protein and a multimer of the receptor. In these embodiments, the heparin mimicking polymer binds to the target proteins only, the receptors only, or to both the target proteins and the receptors.

In some embodiments, the moiety in the target protein is selected from the group consisting of a free thiol group, an amine group, an aldehyde group, a carboxyl group, a hydroxyl group, a ketone group, an oxo group, an azide group, an alkyne group, and a combination thereof.

In some embodiments, the moiety in the target protein is present naturally in the target protein or added by chemical or biological modification.

In some embodiments, the reactive group is selected from the group consisting of activated disulfides, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, alkynes, derivatives thereof, or a combination thereof.

In some embodiments, the heparin mimicking polymers provided herein have the general structure: —[R1R2C—CR3R4]n-, where R1-R4 are selected from the group consisting of a hydrogen, an alkyl, an aryl, an alkene, an alkyne, or any derivative thereof.

In some embodiments, one of the R1-R4 groups comprises a negatively charged moiety. In some embodiments, the R1-R4 groups comprise multiple negatively charged moieties.

In some embodiments, the negatively charged moiety is selected from the group consisting of a sulfate, a sulfonate, a carboxylate, or any combination thereof.

In some embodiments, the heparin mimicking polymer is selected from the group consisting of poly(styrene sulfonate) (pSS), poly(styrene sulfonate)-co-poly(polyethylene glycol methacrylate) (pSS-co-PEGMA), poly(sodium vinyl sulfonic acid) (pVS), or any combination thereof. In some embodiments, the heparin mimicking polymer comprises one or more of pSS, pSS-co-PEGMA, and pVS.

In some embodiments, the heparin mimicking polymer comprises poly(styrene sulfonate) (pSS). In some embodiments, the heparin mimicking polymer is poly(styrene sulfonate) (pSS).

In some embodiments, the heparin mimicking polymer comprises poly(styrene sulfonate)-co-poly(polyethylene glycol methacrylate) (pSS-co-PEGMA). In some embodiments, the heparin mimicking polymer is poly(styrene sulfonate)-co-poly(polyethylene glycol methacrylate) (pSS-co-PEGMA).

In some embodiments, the heparin mimicking polymer comprises poly(sodium vinyl sulfonic acid) (pVS). In some embodiments, the heparin mimicking polymer is poly(sodium vinyl sulfonic acid) (pVS).

In one aspect, provided herein is a method of making a heparin mimicking polymer as disclosed herein.

In one aspect, provided herein is a composition comprising a heparin mimicking polymer as disclosed herein.

In one aspect, provided herein is a method of treating or ameliorating a disorder. The method comprises administering to a subject an effective amount of a heparin mimicking polymer as disclosed herein.

In one aspect, provided herein is a conjugate comprising a heparin mimicking polymer and a biologic agent, where the heparin mimicking polymer comprises a reactive group that reacts with a moiety in a target protein to form a covalent attachment of the polymer to the target protein.

In some embodiments, the biologic agent is a member of the fibroblast growth factor family.

In some embodiments, the biologic agent is selected from the group consisting of a fibroblast growth factor, a keratinocyte growth factor (KGF), a vascular endothelial growth factor (VEGF), a platelet derived growth factor (PDGF), a placental growth factor (PlGF), a hepatocyte growth factor (HGF), an insulin-like growth factor-binding protein, a TGF-β family members, pleiotrophin (PLN), anti-thrombin III (AT III), a secretory leukocyte protease inhibitor (SLKI), a C1 esterase inhibitor (C1 INH), a valosin-containing protein (VCP), platelet factor 4 (PF-4), interleukin 8 (IL-8), stromal cell-derived factor α (SDF-1α), interferon-gamma (INF-gamma), macrophage inflammatory protein-1 (MIP-1), monocyte chemoattractant protein-1 (MCP-1), interferon-γ-inducible protein-10 (IP-10), an Annexin, apolipoprotein E (ApoE), apolipoprotein B (ApoB), apolipoprotein A-V (ApoA-V), human immunodeficiency virus type-1 gp120 (HIV-1 gp120), cyclophilin A, HIV-Tat transactivating factor (Tat), herpes simplex virus (HSV), dengue virus envelop protein, malaria CS protein, lipoprotein lipase, hepatic lipase, selectins, vitronectin, fibronectin, laminin, heparin-binding growth associated molecule (HB-GAM), adaptor protein (AP), or any combination thereof.

In some embodiments, the biologic agent is basic fibroblast growth factor (bFGF).

In some embodiments, the moiety in the target protein is selected from the group consisting of a free thiol group, an amine group, an aldehyde group, a carboxyl group, a hydroxyl group, a ketone group, an oxo group, an azide group, an alkyne group, or any combination thereof.

In some embodiments, the moiety in the target protein is present naturally in the target protein or added by chemical or biological modification.

In some embodiments, the heparin mimicking polymer is selected from the group consisting of poly(styrene sulfonate) (pSS), poly(styrene sulfonate)-co-poly(polyethylene glycol methacrylate) (pSS-co-PEGMA), poly(sodium vinyl sulfonic acid) (pVS), or any combination thereof.

In some embodiments, the heparin mimicking polymer comprises poly(styrene sulfonate) (pSS). In some embodiments, the heparin mimicking polymer is poly(styrene sulfonate) (pSS).

In some embodiments, the heparin mimicking polymer comprises poly(styrene sulfonate)-co-poly(polyethylene glycol methacrylate) (pSS-co-PEGMA). In some embodiments, the heparin mimicking polymer is poly(styrene sulfonate)-co-poly(polyethylene glycol methacrylate) (pSS-co-PEGMA).

In some embodiments, the heparin mimicking polymer comprises poly(sodium vinyl sulfonic acid) (pVS). In some embodiments, the heparin mimicking polymer is poly(sodium vinyl sulfonic acid) (pVS).

In some embodiments, a plurality of bFGFs are attached to one or more heparin mimicking polymer.

In some embodiments, the conjugate comprises bFGF-pSS-co-PEGMA-bFGF.

In some embodiments, the conjugate comprises bFGF-pSS-bFGF.

In some embodiments, the conjugate comprises bFGF-pVS-bFGF.

In some embodiments, the conjugate comprises bFGF-polyethylene glycol(PEG)-bFGF.

In one aspect, provided herein is a composition that comprises a conjugate as disclosed herein.

In one aspect, provided herein is a method of making a conjugate as disclosed herein.

In one aspect, provided herein is a method of treating or ameliorating a disorder, where the method comprises a step of administering to a subject an effective amount of a conjugate as disclosed herein.

In another aspect, the present invention provides a conjugate comprising a heparin mimicking polymer and a biologic agent. In some embodiments, the biologic agent is bFGF. In some embodiments, the biologic agent can be any heparin-binding protein, including but not limited to: any of the fibroblast growth factors (such as FGF-1, 2, 3, 4, 5, 6, 7, 8, 9, 10, 11, 12, 13, 14, 15, 16, 17, 18, 19, 20, and 21), keratinocyte growth factor (KGF), vascular endothelial growth factor (VEGF), platelet derived growth factor (PDGF), placental growth factor (PlGF), hepatocyte growth factor (HGF), insulin-like growth factor-binding proteins, TGF-β family members, pleiotrophin (PLN), antithrombin III (AT III), secretory leukocyte protease inhibitor (SLKI), C1 esterase inhibitor (C1 INH), valosin-containing protein (VCP), platelet factor 4 (PF-4), interleukin 8 (IL-8), stromal cell-derived factor α (SDF-1α), interferon-gamma (INF-gamma), macrophage inflammatory protein-1 (MIP-1), monocyte chemoattractant protein-1 (MCP-1), interferon-g-inducible protein-10 (IP-10), annexins (Annexin I, II, III, IV, V and, VI), apolipoprotein E (ApoE), apolipoprotein B (ApoB), apolipoprotein A-V (ApoA-V), human immunodeficiency virus type-1 gp120 (HIV-1 gp120), cyclophilin A, HIV-Tat transactivating factor (Tat), herpes simplex virus (HSV), dengue virus envelop protein, malaria CS protein, lipoprotein lipase, hepatic lipase, selectins, vitronectin, fibronectin, laminin, heparin-binding growth associated molecule (HB-GAM), and adaptor protein (AP).

In some embodiments, the heparin mimicking polymer comprises a reactive group that reacts with a moiety in a biologic agent (e.g., a protein such as bFGF) causing covalent attachment of the polymer to the biologic agent. For example, an embodiment of such a heparin mimicking polymer can include a reactive group(s) that reversibly reacts with free thiol groups (e.g., cysteines) in the biologic agent.

In another aspect, the present invention provides a composition comprising a conjugate that comprises a heparin mimicking polymer and a biologic agent.

In another aspect, the present invention provides a method of making a conjugate comprising a heparin mimicking polymer and a biologic agent.

In another aspect, the present invention provides a method of making a heparin mimicking polymer, with or without a reactive group. In some embodiments, the reactive group is at one terminus or both termini of the heparin mimicking polymer. In some embodiments, the reactive group is a substituent or pendant group on the heparin mimicking polymer.

In some embodiments, the reactive group reacts with a free thiol in the biologic agent. Examples of such reactive groups include, but are not limited to, activated disulfides (also called thiol-disulfide exchange reagents) such as pyridyl disulfide, 5-thio-2-nitrobenzoic acid, and disulfide reductants, Michael acceptors such as maleimides, maleimide derivatives including dihalomaleimides, and vinyl groups including vinyl sulfones and acryloyl derivatives, haloacetyl and other alkyl halide derivatives, aziridines, and arylating agents.

In some embodiments, the reactive group reacts with a free amine in the biologic agent. Examples of such reactive groups include, but are not limited to, isothiocyanates, isocyanates, acryl azides, activated esters such as N-hydroxysuccinimide and para-nitrophenyl, sulfonyl chlorides, aldehydes and glyoxals (with or without reductive amination), epoxides (also called oxiranes), carbonates, arylating agents, imidoesters, carbodiimides, and anhydrides.

In some embodiments, the reactive group reacts with a carboxyl group in the biologic agents. Examples of such reactive groups include, but are not limited to, amines via amination chemistry, diazoalkanes and diazoacetyl compounds.

In some embodiments, the reactive groups react with hydroxyl groups in the biologic agents. Examples of such reactive groups include, but are not limited to, epoxides (also called oxiranes), carbonyldiimidazoles, carbonates and chloroformates, alkyl halogens, and isocyanates.

In some embodiments, the reactive group reacts with a aldehyde, ketone, or any other oxo moiety introduced into the biologic agent. Examples of such reactive groups include, but are not limited to, aminooxy (hydroxylamines), hydrazines, and amines (with and without reductive amination).

In some embodiments, the reactive group reacts with azide or alkyne groups introduced in the biologic agent. Examples of such reactive groups include, but are not limited to, alkynes and amines.

In some embodiments, the moiety that reacts with the reactive group is present naturally in the biologic agent. In some embodiments, the moiety that reacts with the reactive group is added to the biologic agent by chemical modification (e.g., by chemical synthesis) or biological modification (e.g., inclusion of non-naturally amino acids via recombinant synthesis).

In another aspect, the present invention provides a method of treating or ameliorating a disorder, comprising administering to a subject a conjugate comprising a heparin mimicking polymer and a biologic agent.

In some embodiments, provided herein are copolymers of poly(styrene sulfonate)-co-poly(polyethylene glycol methacrylate) (pSS-co-PEGMA) and methods for utilizing the same. The copolymer is heparin mimicking and binds to the heparin-binding domain of a biologic agent, such as bFGF and VEGF. In this invention, the polymer was synthesized by reversible addition-fragmentation chain transfer (RAFT) polymerization to contain a pyridyl disulfide end group. Previously, the polymer had been synthesized with a vinyl sulfone end group. The conjugate with bFGF was prepared by modification of a free cysteine of the protein with the polymer via a disulfide bond, which is reversible.

In some embodiments, provided herein are conjugates comprising copolymers of poly(styrene sulfonate)-co-poly (polyethylene glycol methacrylate) (pSS-co-PEGMA) and methods for utilizing the same.

In some embodiments, provided herein are conjugates comprising poly(sodium vinyl sulfonic acid) (pVS) polymers.

In some embodiments, a polymer-biologic agent conjugate comprises multiple copies of a biologic agent (e.g., bFGF and VEGF or any other heparin binding biomolecules), such as two or more copies, three or more copies, four or more copies, five or more copies, six or more copies, seven or more copies, eight or more copies, nine or more copies, ten or more copies, 12 or more copies, 15 or more copies, or 20 or more copies.

In some embodiments, a polymer-biologic agent conjugate comprises multiple copies of a heparin mimicking polymer (e.g., pSS-co-PEGMA or pVS), such as two or more copies, three or more copies, four or more copies, five or more copies, six or more copies, seven or more copies, eight or more copies, nine or more copies, ten or more copies, 12 or more copies, 15 or more copies, or 20 or more copies.

BRIEF DESCRIPTION OF THE DRAWINGS

FIGS. 1A-1H depict the synthesis and characterizations of an embodiment of present invention, PDS-pSS-co-PEGMA. (A) Synthesis scheme; (B) 1H NMR spectrum in $D_2O$; (C) GPC trace of PDS-pSS-co-PEGMA before and after radical exchange in DMF 0.1M LiBr; (D) Kinetic studies of the RAFT polymerization at 70° C.: kinetic trace and conversions determined by 1H NMR spectroscopy (left), MWs and PDIs determined by GPC (right), ratios of incorporating monomers determined by 1H NMR (bottom); (E) FT-IR spectrum of the polymer; (F) GEMMA spectrum of the polymer taken in 20 mM Ammonium Acetate (EMD=4.51 nm, d=0.90 g/cm$^3$ calculated using formula: $d=MW/(N_a*EMD^3*\pi/6)$; (G) UV-Vis spectra of the polymer before and after radical exchange with AIBN; and (H) Results of quantitative analysis of the PDS end group retention after radical exchange and purification.

heparin v.pSS; B) heparin, pSPM-co-HEMA, and pSPM; C) heparin v. pAMPS-co-HEMA; and D) heparin, pVS and pAHPS.

Figure 14:
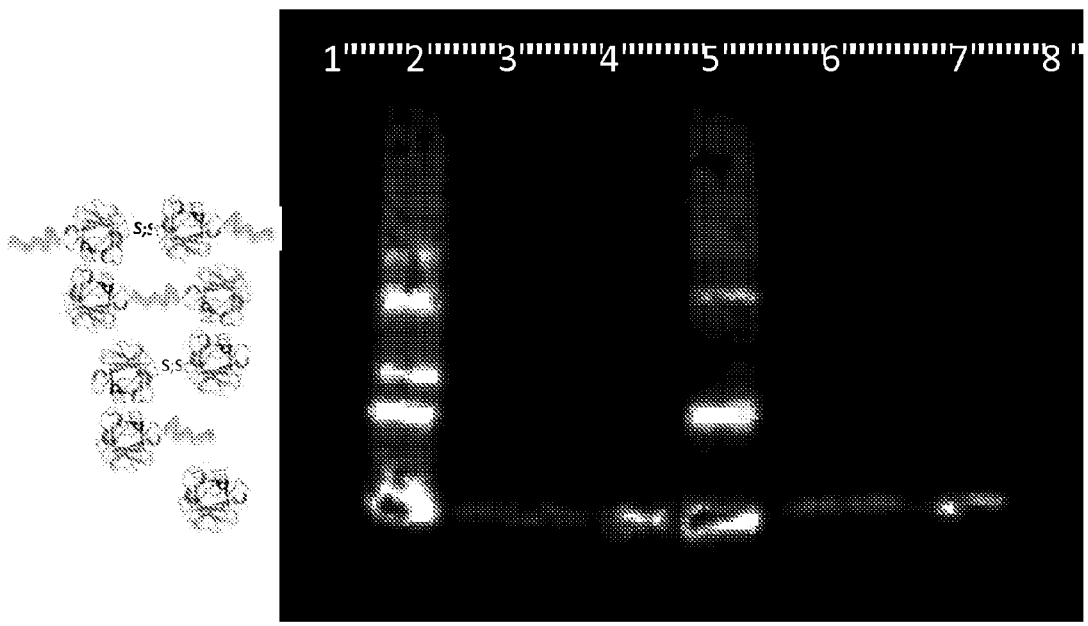

FIG. 14 depicts an exemplary Western blot of bFGF-PEG-bFGF, lane 1: protein ladder, lane 2: 2 M fraction under non-reducing conditions, lane 3: 2 M filtrate under non-reducing fractions, lane 4: bFGF under non-reducing conditions, lane 5: 2 M fraction under reducing conditions, lane 6: 2 M filtrate under reducing conditions, lane 7: bFGF under reducing conditions, lane 8: protein ladder.

Figure 15:
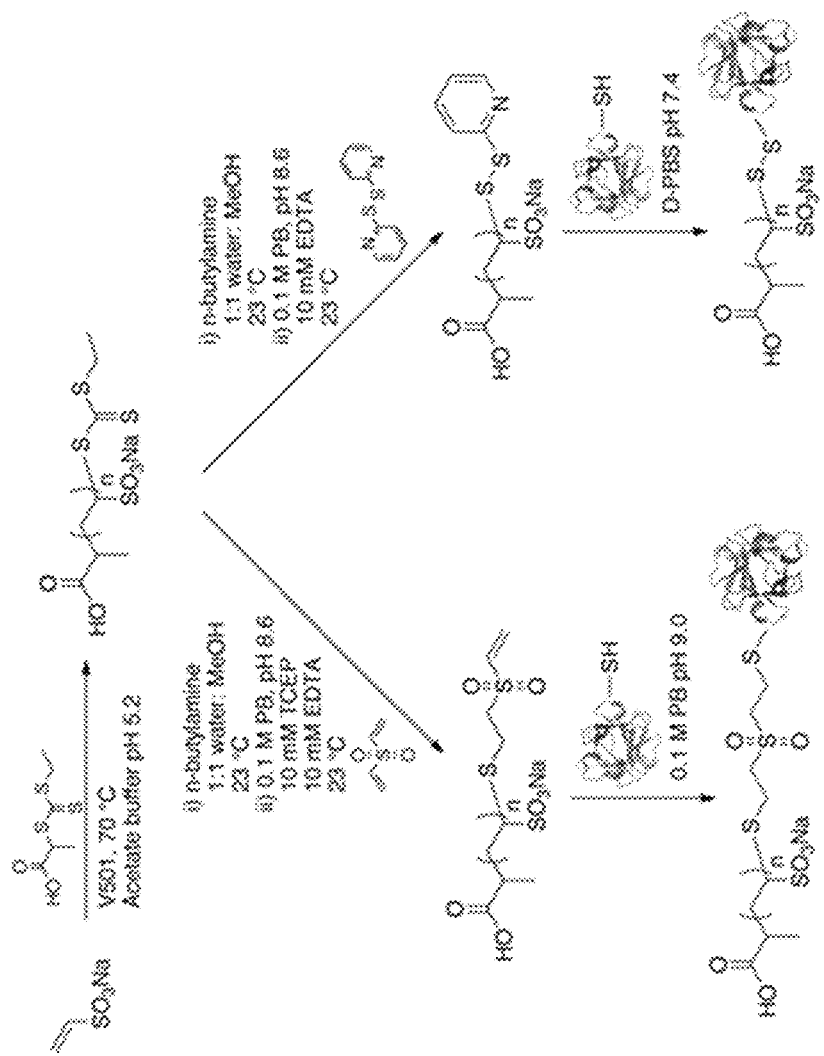

FIG. 15 shows Scheme 1: Synthesis of bFGF-pVS conjugate, Route #1.

Figure 16:
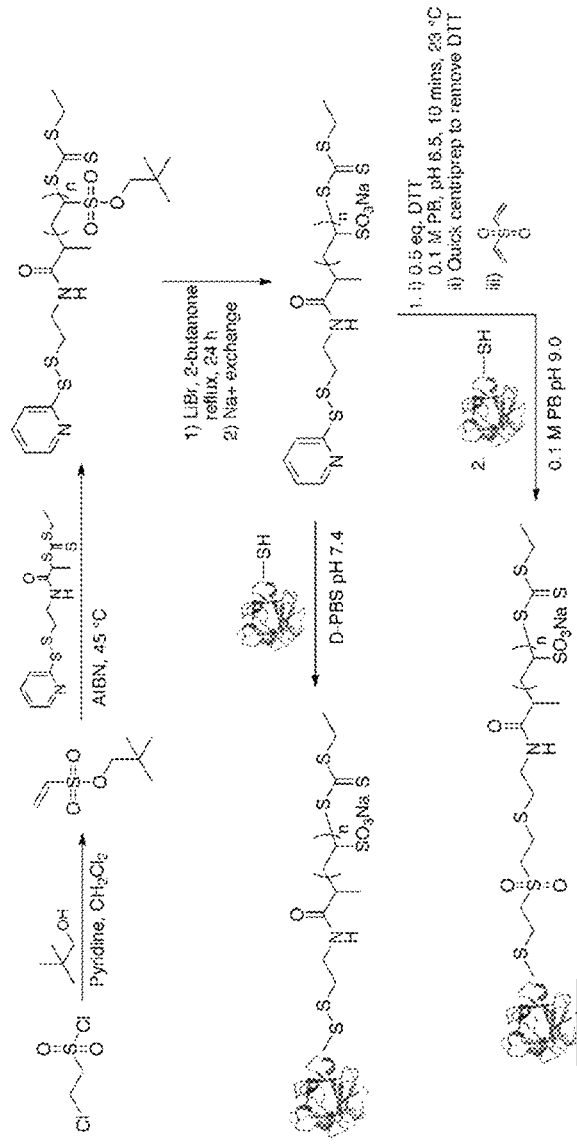

FIG. 16 shows Scheme 2: Synthesis of bFGF-pVS conjugate, Route #2.

Figure 17:
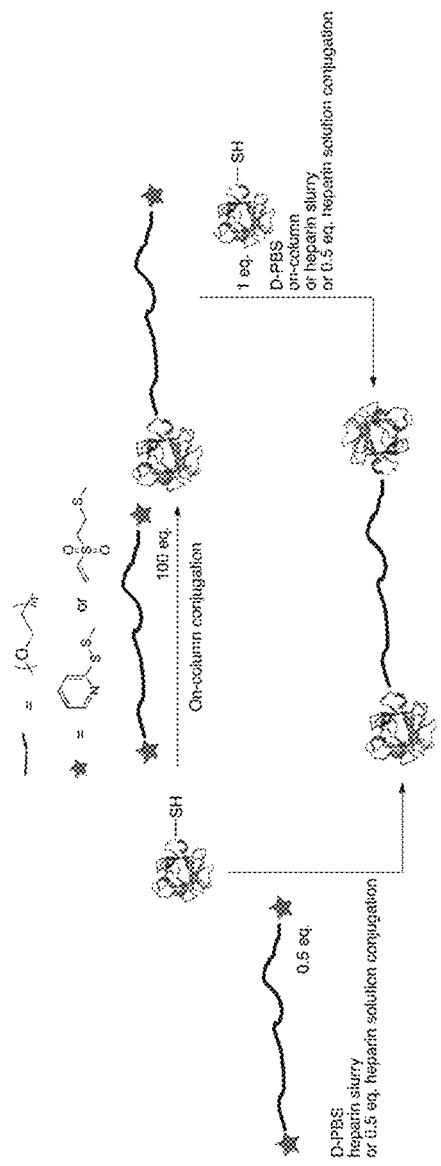

FIG. 17 shows Scheme 4: Synthesis of bFGF-PEG-bFGF.

FIG. 18 shows Scheme 6: Synthesis of bFGF-pVS-bFGF.

DETAILED DESCRIPTION OF THE INVENTION

As described herein, "a heparin mimicking polymer" refers to a polymer that interacts with a target molecule, such as a protein or receptor, in a manner that is similar to the interaction between heparin and the target molecule. In some embodiments the interaction between heparin mimicking polymer and the target molecule is an electrostatic interaction. This may result, for example in the polymer stabilizing a protein or inducing a biological response as does heparin.

In one aspect, the present invention provides a heparin mimicking polymer.

In another aspect, the present invention provides a conjugate comprising a heparin mimicking polymer and a biologic agent. In some embodiments, the biologic agent is bFGF. In some embodiments, the biologic agent can be any heparin-binding protein, including but not limited to: any of the fibroblast growth factors (such as FGF-1, 2, 3, 4, 5, 6, 7, 8, 9, 10, 11, 12, 13, 14, 15, 16, 17, 18, 19, 20, and 21), keratinocyte growth factor (KGF), vascular endothelial growth factor (VEGF), platelet derived growth factor (PDGF), placental growth factor (PlGF), hepatocyte growth factor (HGF), insulin-like growth factor-binding proteins, TGF-β family members, pleiotrophin (PLN), antithrombin III (AT III), secretory leukocyte protease inhibitor (SLKI), C1 esterase inhibitor (C1 INH), valosin-containing protein (VCP), platelet factor 4 (PF-4), interleukin 8 (IL-8), stromal cell-derived factor α (SDF-1α), interferon-gamma (INF-gamma), macrophage inflammatory protein-1 (MIP-1), monocyte chemoattractant protein-1 (MCP-1), interferon-γ-inducible protein-10 (IP-10), annexins (Annexin I, II, III, IV, V and, VI), apolipoprotein E (ApoE), apolipoprotein B (ApoB), apolipoprotein A-V (ApoA-V), human immunodeficiency virus type-1 gp120 (HIV-1 gp120), cyclophilin A, HIV-Tat transactivating factor (Tat), herpes simplex virus (HSV), dengue virus envelop protein, malaria CS protein, lipoprotein lipase, hepatic lipase, selectins, vitronectin, fibronectin, laminin, heparin-binding growth associated molecule (HB-GAM), and adaptor protein (AP).

In some embodiments, the heparin mimicking polymer comprises a reactive group that reacts with a biologic agent (e.g., a protein such as bFGF) causing covalent attachment of the polymer to the biologic agent. For example, an embodiment of such a heparin mimicking polymer can include a reactive group(s) that reversibly reacts with free thiol groups (e.g., cysteines) in the biologic agent.

In another aspect, the present invention provides a composition comprising a conjugate that comprises a heparin mimicking polymer and a biologic agent. In some embodiments of the composition, the heparin mimicking polymer comprises a reactive group that reacts with a biologic agent (e.g., a protein such as bFGF) causing covalent attachment of the polymer to the biologic agent. For example, an embodiment of such heparin mimicking polymer can include a reactive group(s) that reacts with free cysteines, heparin mimicking polymer that reacts with free thiol groups (e.g., cysteines) reversibly.

In another aspect, the present invention provides a method of making a conjugate comprising a heparin mimicking polymer and a biologic agent according to the various embodiments disclosed herein.

In another aspect, the present invention provides a method of making a heparin mimicking polymer of the various embodiments disclosed herein.

In another aspect, the present invention provides a method of treating or ameliorating a disorder, comprising administering to a subject a conjugate comprising a heparin mimicking polymer and a biologic agent of the various embodiments disclosed above or below.

bFGF

Basic fibroblast growth factor (bFGF), a 16-kDa polypeptide, is a member of a family of 23 fibroblast growth factors. The protein, also called fibroblast growth factor 2 (FGF2), plays a crucial role in embryonic development, angiogenesis, tissue regeneration, bone regeneration, development and maintenance of the nervous system, stem cell self renewal, and wound repair. As a result bFGF is promising for a wide range of therapeutic applications. However, bFGF is unstable and degrades rapidly upon storage and delivery, and this instability has hindered clinical use of this protein. Association with the polysaccharide heparin can stabilize bFGF. However, heparin has biological activity itself that can be deleterious, is difficulty to modify, and exhibits batch-to-batch variability. It also has significant bioactivity in other, non-target biological pathways.

This invention provides a highly effective way to stabilize the growth factor by conjugation of a heparin-mimicking polymer to the protein. Covalently binding a heparin-mimicking polymer to bFGF ensures that the minimum therapeutically useful concentration of the polymer is employed. bFGF-heparin mimicking polymer conjugates are stable to environmental stressors including storage, acidic pH, heat, and enzymes; the conjugates still induce cell proliferation after treatment. The stable bFGF-polymer conjugates will be useful for any commercial application where bFGF would have activity, including wound healing for chronic and acute wounds, burn repair, bone regrowth, cardioprotection, neuronal protection and regeneration, and many different kinds of tissue regeneration. The conjugates should also be useful for the use and study of bFGF in research settings. Possible products include, but are not limited to, a topical treatment for a variety of clinical settings including wound healing, as a injectable therapeutic for a variety of diseases, as cell culture additives for stem cell self renewal, and for use as a reagent in research settings. The polymer employed in the example provided in this invention is poly(styrene sulfonate)-co-poly(poly(ethylene glycol methacrylate) (pSS-co-PEGMA), although numerous other negatively charged polymers including, but not limited to those, containing sulfonates, sulfates, and carboxylates can be utilized. bFGF is the protein demonstrated, however, any heparin binding protein could be utilized. These include, but are not limited to: fibroblast growth factors (such as FGF-1, 2, 3, 4, 5, 6, 7, 8, 9, 10, 11, 12, 13, 14, 15, 16, 17, 18, 19, 20, and 21), keratinocyte growth factor (KGF), vascular endothelial growth factor (VEGF), platelet derived growth factor (PDGF), placental growth factor (PlGF), hepatocyte growth factor (HGF), insulin-like growth factor-binding proteins, TGF-β family members, pleiotrophin (PLN), antithrombin III (AT III), secretory leukocyte protease inhibitor (SLKI), C1 esterase inhibitor (C1 INH), valosin-containing protein (VCP), platelet factor 4 (PF-4), interleukin 8 (IL-8), stromal cell-derived factor α (SDF-1α), interferon-gamma (INF-gamma), macrophage inflammatory protein-1 (MIP-1), monocyte chemoattractant protein-1 (MCP-1), interferon-g-inducible protein-10 (IP-10), annexins (Annexin I, II, . . . , VI), apolipoprotein E (ApoE), apolipoprotein B (ApoB), apolipoprotein A-V (ApoA-V), human immunodeficiency virus type-1 gp120 (HIV-1 gp120), cyclophilin A, HIV-Tat transactivating factor (Tat), herpes simplex virus (HSV), dengue virus envelop protein, malaria CS protein, lipoprotein lipase, hepatic lipase, selectins, vitronectin, fibronectin, laminin, heparin-binding growth associated molecule (HB-GAM), and adaptor protein (AP). This considerably widens the types of commercial applications and products this invention may lead to.

In particular, described herein are methods for stabilizing bFGF by covalent conjugation of a heparin mimicking polymer, poly(sodium 4-styrenesulfonate-co-poly(ethylene glycol) methyl ether methacrylate) (pSS-co-PEGMA). The bFGF-pSS-co-PEGMA conjugate retained bioactivity after synthesis and was stable to a variety of environmentally and therapeutically relevant stressors such as heat, mild and harsh acidic conditions, storage, and proteolytic degradation compared to native bFGF. The bFGF-heparin mimicking polymer conjugate was also significantly more active than bFGF-poly(ethylene glycol) methyl ether methacrylate) (bFGF-pPEGMA) after applied stress, demonstrating the value of the heparin mimicking polymer to stabilize this growth factor. Also described herein are applications of the clinical use of bFGF and for the stabilization of heparin-binding growth factors in general.

This invention is the first conjugate of bFGF that has a heparin-mimicking polymer attached.

This invention is the first bFGF-polymer conjugate that fully retains bioactivity.

This invention is the first bFGF conjugate that is stable to numerous stressors. These include exposure to heat, to enzymes, to moderate and low pH, and stirring.

bFGF is an important protein with many therapeutic uses. However, the protein must be stabilized during storage and delivery. Molecules employed thus far to stabilize bFGF have difficulties associated with their use. Most have biological activity in the body such as anticoagulant and antiangiogenic activities and associated complications. Furthermore, some of the natural polysaccharides utilized for this purpose are difficult to modify or exhibit batch-to-batch variability.

In some embodiments, heparin and heparin-mimicking additives inhibit binding to the bFGF receptors at moderate to high concentrations, lowering or inhibiting the biological activity of the protein, which can counteract the desired effect. For example, high concentrations of heparin can inhibit human umbilical vein endothelial cells and human dermal fibroblasts, which can counteract the regular effects of bFGF in wound healing and other applications to produce the desired counteraction.

The use of a synthetic polymer conjugate has advantages compared to these non-covalent stabilizers: (1) Because the polymer is conjugated to the protein, the minimum therapeutically useful dose to stabilize the protein is required. The polymer is attached to the protein and stabilizes it due to its proximity to the heparin binding domain. Yet, the protein itself is still completely active. The concentration required in the conjugate to stabilize the protein is non-toxic (see FIG. 5) and does not inhibit biological activity of the bFGF (see FIGS. 4A and 4B). (2) Unlike typically used stabilizing polymers and materials, the polymer of the conjugates does not need to be removed prior to use. The bFGF-heparin mimicking polymer can be used directly, without requiring removal of the polymer or release of the protein prior to application (see FIG. 4A). (3) A covalent conjugate of bFGF may have additional advantages in in vivo type applications. It is well known the covalent polymer conjugates increase the pharmacological properties of proteins. (4) Non-covalent conjugates may not be useful in vivo because of the likelihood of detachment of the polymer upon dilution before reaching target sites.

Method of Stabilization: Conjugation with Polymers

In one aspect, stabilization of a molecule (e.g., a protein) can be achieved by conjugating the molecule to modifying molecules (e.g., synthetic polymers).

Covalent conjugation of synthetic polymers, in particular poly(ethylene glycol) (PEG), has been widely explored as a means to improve the half-lives of proteins in vivo, and to lower the immunogenicities and/or antigenicities of proteins. Consequently, a number of PEGylated proteins have been approved by the US Food and Drug Administration for treatment of a variety of diseases. However, therapeutic proteins often suffer from instability during storage and use, and PEG does not necessarily stabilize proteins to external stressors. Yet despite this drawback, there are only a few reports of conjugating polymers that stabilize the proteins: Keefe et al. demonstrated that covalently binding poly (carboxybetaine) to α-chymotrypsin improved stability and at the same time retained the enzyme's native binding affinity. In some embodiments, polystyrenes with pendent groups such as trehalose sugars can be added to create conjugates "(e.g., lysozyme conjugates) that are stable to high temperatures and repeated lyophilization.

In some embodiments, polystyrene with pendent trehalose sugars are attached to target proteins (e.g., lysozyme) to form conjugates stable to high temperatures and repeated lyophilization.

In one aspect, provided herein are methods for stabilizing a protein that is a member of a large class of therapeutically useful biologics, namely the heparin-binding proteins, using a polymer specifically designed to interact with the heparin-binding domain of the growth factor.

In some embodiments, polysaccharides such heparin are attached to target proteins. A considerable number of proteins interact with the polysaccharide heparin and make up the class of heparin-binding proteins, including proteases, growth factors, chemokines, lipid-binding proteins, pathogens, and adhesion proteins. Their key biological functions are wide ranging and include blood coagulant processes, cell differentiation, angiogenesis, inflammation processes, host defense and viral infection mechanisms, lipid transport and clearance, and cell adhesion and interaction. Since the introduction of heparin in the early 1900s as an anticoagulant agent, it is now known that the role of heparin in the body is far reaching. Crystallography studies have defined the heparin-binding motifs on numerous proteins, and researchers have found that in many cases their interactions with heparin were critical for both bioactivity and stability.

In some embodiments, polymers mimicking heparin are conjugated with a biologic agent such as a desired target protein or other biomolecules. In some embodiments, an important heparin-binding protein, basic fibroblast growth factor (bFGF) is stabilized by conjugation of a heparin mimicking polymer.

bFGF is a therapeutic target widely investigated because of its crucial role in diverse cellular functions including: embryonic development, angiogenesis, tissue regeneration, bone regeneration, development and maintenance of the nervous system, stem cell self renewal, and wound healing. bFGF is a potent stimulator of proliferation, differentiation and migration of multiple cell types. Therefore, bFGF is promising for a wide variety of applications in regenerative medicine and in other fields of medicine. However, due to bFGF's extreme instability in storage and delivery, its therapeutic effectiveness is not yet widely realized.

Since heparin is the natural stabilizer of bFGF, many researchers employ heparin in controlled release systems of the growth factor. However, heparin itself is difficult to modify, is susceptible to desulfation, suffers from batch-to-batch variation and impurities, and has significant bioactivity in other, non-target biological pathways. In addition, it has been reported to inhibit normal growth of certain cell types including human umbilical vein endothelial cells and human dermal fibroblasts, which could possibly counteract the desirable effects of bFGF. It is known that sulfated and sulfonated polymers can mimic heparin.

In one aspect, provided herein are novel and stabilized conjugates of heparin binding molecules such as bFGF. Thus far, only PEG has been covalently conjugated to bFGF and histidine-tagged bFGF has been non-covalently associated with nitriloacetic acid-nickel modified poly(acrylamide). However, these conjugates have significantly reduced protein activity, require addition of heparin to stabilize the conjugate, or large protein concentrations must be used to elicit a biological effect.

In some embodiments, a heparin mimicking polymer, e.g., poly(sodium 4-styrenesulfonate-co-poly(ethylene glycol) methyl ether methacrylate) (pSS-co-PEGMA), is covalently conjugated to a biologic agent such as bFGF. In some embodiments, a heparin mimicking polymer, e.g., poly(sodium vinyl sulfonic acid) (pVS), is covalently conjugated to a biologic agent such as bFGF. In some embodiments, the conjugation to the biologic agent alters its stability.

Compared to existing covalent conjugates of bFGF, bFGF-heparin mimicking polymer conjugates have many advantages. The bFGF-PEG conjugates that have been reported all have lower activities or require the addition of a stabilizer. Only one has shown enhanced stability by providing an increase in thermal stability at 37° C.; however, this conjugate had over 60% loss of bioactivity. The bFGF-heparin mimicking polymer completely retains activity, and further shows remarkable stability to storage at 4° C., to treatment with high temperature (55° C.), to incubation with the enzyme trypsin, and to both treatment with pH 4.7 buffer and 1% TFA (see FIGS. 4A and 4B).). In some embodiments, the bFGF-heparin mimicking polymer is stored at 4° C. for a day or longer; two days or longer; four days or longer; a week or longer; 2 weeks or longer; 3 weeks or longer; 4 weeks or longer; 5 weeks or longer; 6 weeks or longer; 7 weeks or longer; 8 weeks or longer; 3 months or longer; 4 months or longer; 6 months or longer; or a year or longer.

Compared to reported non-covalent conjugates of related proteins, the stability of the covalent bond as described in this invention is important for in vitro and in vivo work where loss of the associated polymer may occur. In addition, the use of a histidine tag-nickel interaction requires that the protein be expressed with this tag and that toxic metals be used to form the conjugate. Furthermore, covalent conjugates are well known to have longer lifetimes and enhanced pharmacology properties in vivo, another advantage of this invention.

In some embodiments, conjugation to a biologic agent alters its reactivity. In some embodiments, conjugation to a biologic agent changes both its stability and reactivity, simultaneously or sequentially. For example, in some embodiments, conjugates of a biologic agent (e.g., bFGF) do not show increased stability, but have altered reactivities such as gain or loss of cytotoxicity.

Interactions Between Heparin Mimicking Polymers and Target Molecules

In some embodiments, disclosed herein is a heparin mimicking polymer that also interacts with the receptors of the biologic agent and promotes its binding to the biologic agent (e.g., bFGF), in a manner similar to heparin. In some embodiments, the heparin mimicking polymer that promotes the interaction between the biologic agent and its receptor comprises sulfated or sulfonated polymers. Promoting the interaction between the biologic agent and its receptor can be achieved via binding to the biologic agent, its receptor or both.

In some embodiments, disclosed herein is a heparin mimicking polymer that binds to and stabilizes the interaction between a dimer of the biologic agent and a corresponding dimeric receptor; for example, a heparin mimicking polymer can bind to two bFGFs and facilitate their binding to a dimeric receptor thereof. Alternatively, a heparin mimicking polymer can bind to a dimeric receptor of bFGF and facilitate their binding to two bFGFs. Still alternatively, a heparin mimicking polymer can bind to a dimeric receptor of bFGF and two bFGFs at the same time and facilitate their interaction.

In some embodiments, covalent conjugation with a target molecule (e.g., a protein or a receptor) is established via formation of a disulfide bond between the heparin mimicking polymer of the target molecule. In some embodiments, polymers that are known to interact with a target protein are selected as candidates of the heparin mimicking polymer prior to further modification of the selected polymers to facilitate disulfide bond formation. For example, pSS-co-PEGMA was selected because we demonstrated that the polymer bound to bFGF in cell culture media, likely through interaction with the heparin-binding domain. bFGF has two free thiol groups (e.g., cysteines). In some embodiments, a pyridyl disulfide (PDS) end group is added to a selected polymer so that the modified polymer that reacts with thiols in a target protein (e.g., bFGF).

Figure 12A:
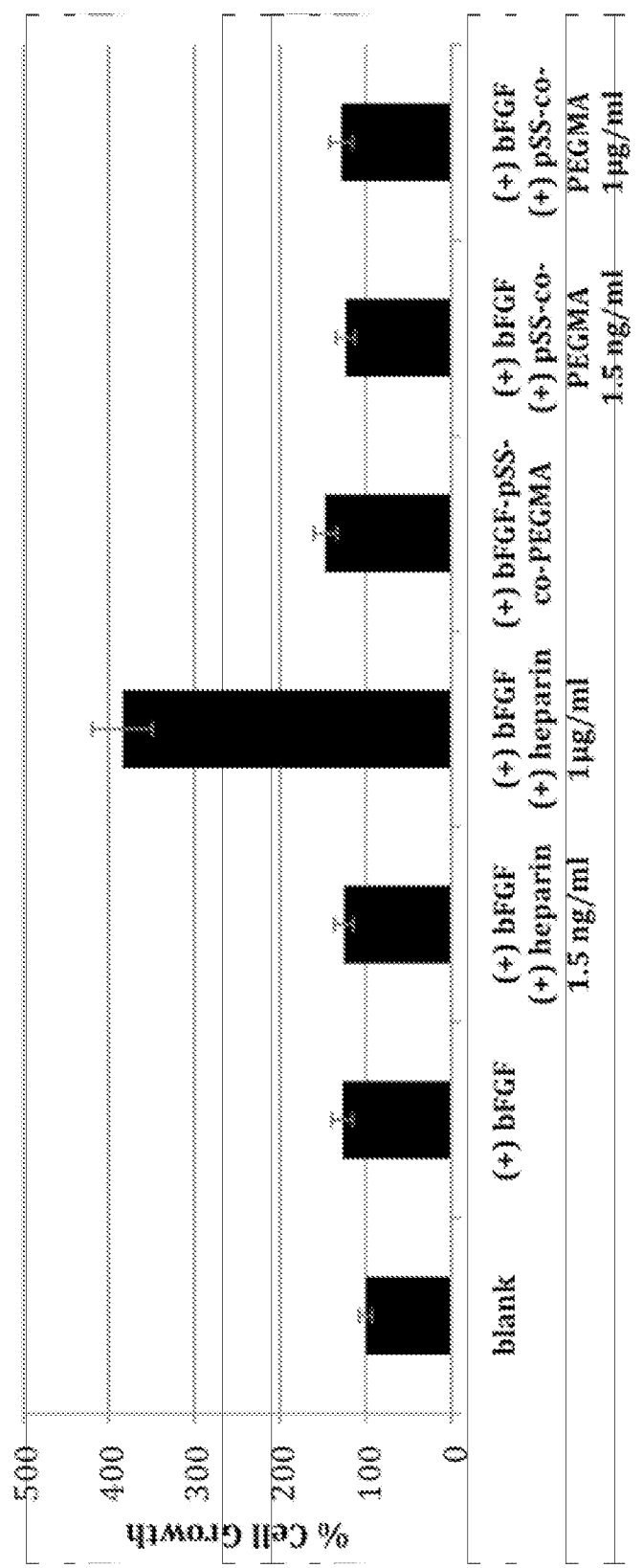
FIGS. 12A-12C depict exemplary results of proliferation study with BaF3 cells. (A) BaF3 cells (FR1C-11), which express FGFR1 but lack heparin sulfate proteoglycans, were seeded at a density of 20,000 cells/well in cultured medium lacking IL-3 in a 96-well-plate. The samples were prepared in the working medium with the final concentrations: 1 ng/ml of bFGF, 1 ng/ml of bFGF with either 1.5 ng/ml or 1 μg/ml of heparin or with 1.5 ng/ml or 1 μg/ml of pSS-co-PEGMA, and 1 ng/ml of bFGF-pSS-co-PEGMA. The cells were incubated for 42 hours. CellTiter® blue assay was performed to quantify percent cell growth. Data was normalized to blank sample group. Each group was done with six replicates. Error bars are standard deviations. Heparin induces dimerization of bFGFs (gold) and bFGFRs (blue and green), depicted in ball & stick rep. shown on heparin binding domain, top B) and surface rendering structure, bottom C).
Figures 12B, 12C:
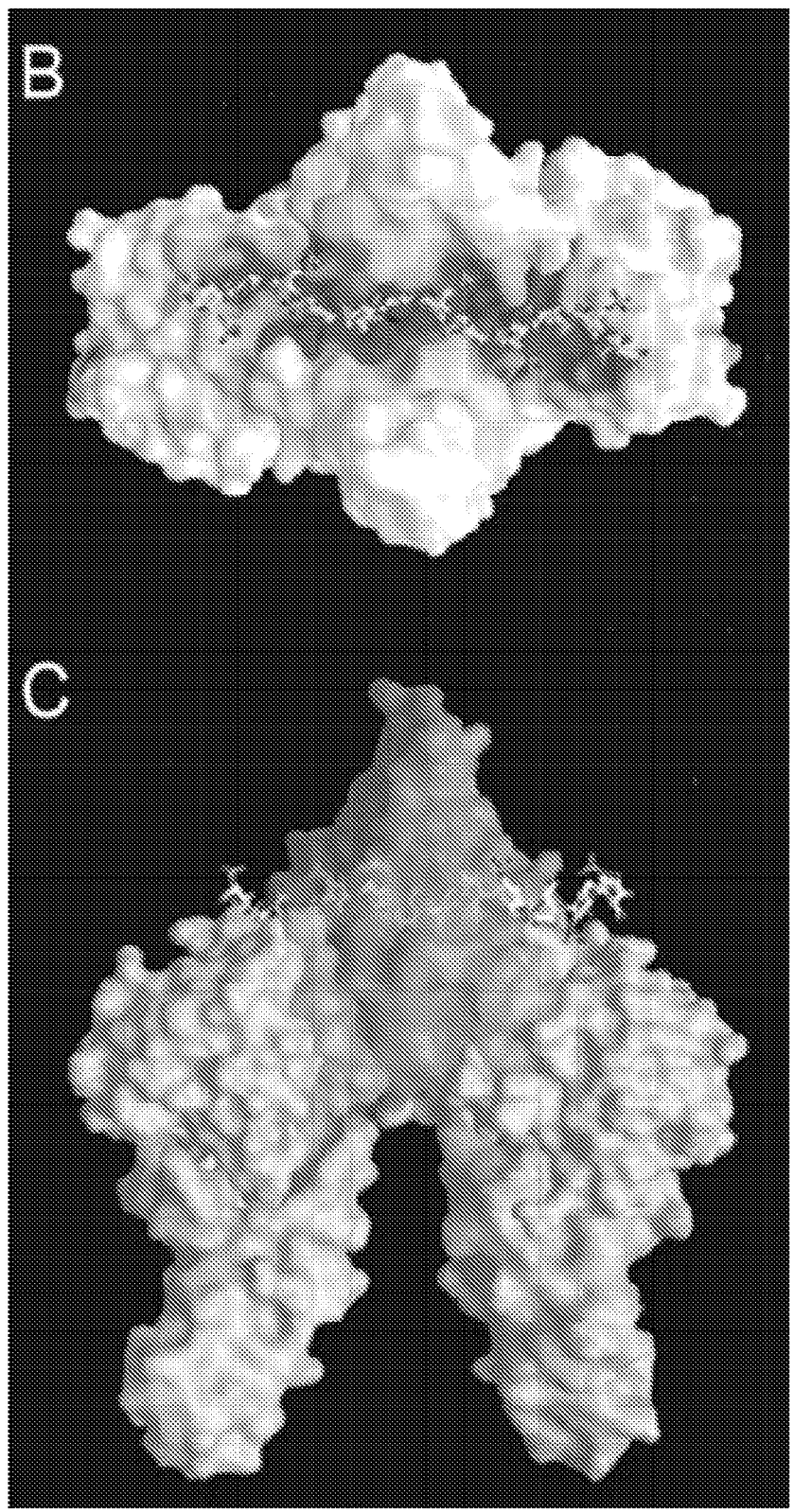
Figure 13A:
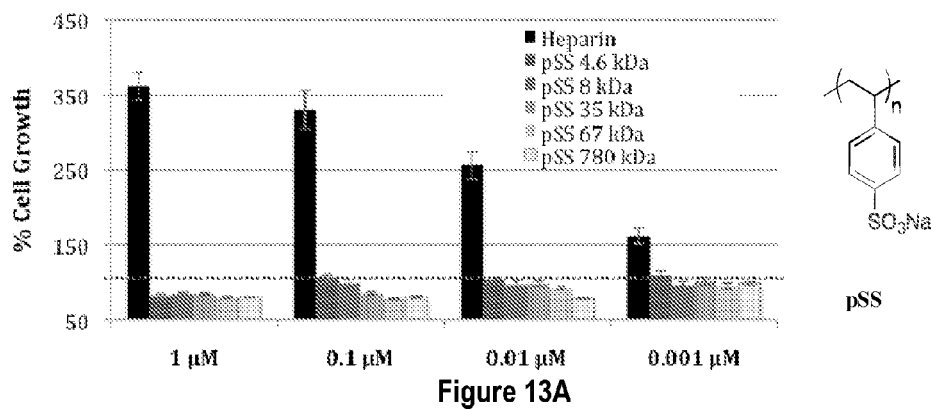
FIGS. 13A-13D depict the exemplary results of screening experiments for new heparin-mimicking polymer. BaF3 cells (FR1C-11) were seeded at a density of 20,000 cells/well in cultured medium lacking IL-3 in a 96-well-plate. The samples were prepared in the working medium to contain 1-2 ng/ml of bFGF with increasing concentrations of the polymers tested (the labels in the x-axis indicate the concentrations of the polymers). The cells were incubated for 42 hours. CellTiter® blue assay was performed to quantify percent cell growth. Data was normalized to the control group, which contained bFGF only. Each group was done with four replicates. Error bars are standard deviations. A)
Figure 13B:
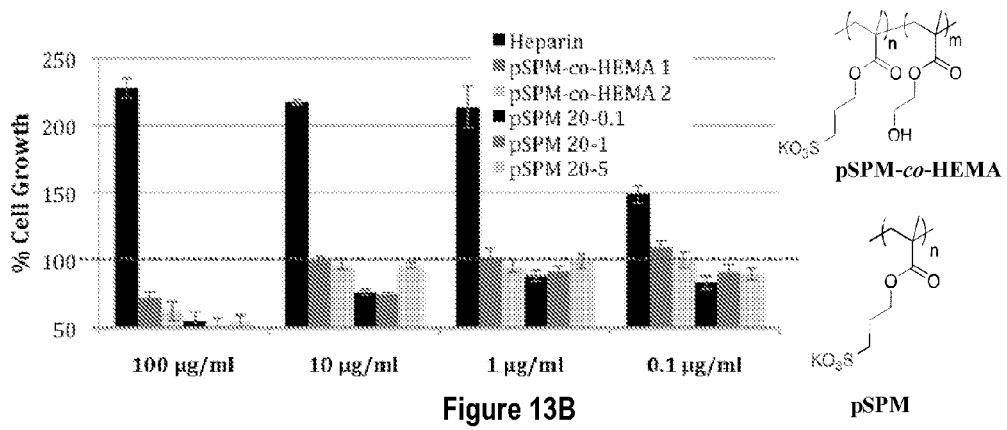
Figure 13C:
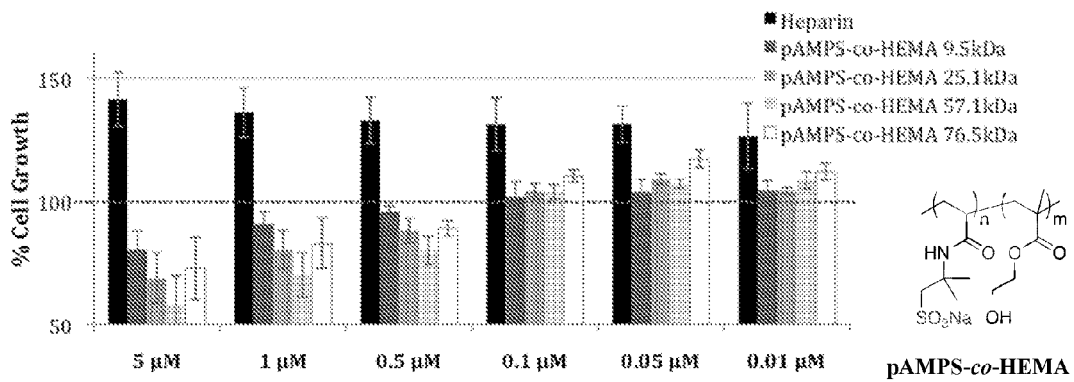
Figure 13D:
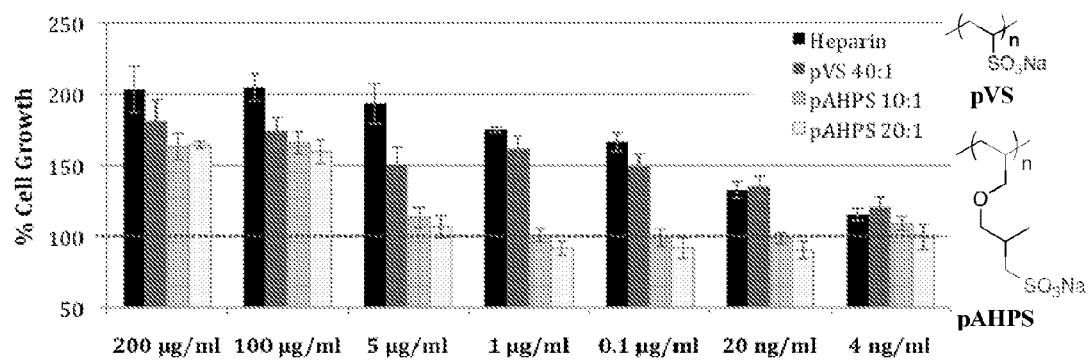

Heparin (as cell surface receptors called heparan sulfate proteoglycans) is also known to increase the mitogenic activity of bFGF by increasing binding to the bFGF receptors (FGFRs). In addition, heparin promotes bFGFR dimerization by providing the "glue" between two bFGFs and two FGFRs (see crystal structure, FIGS. 12B and 12C). In fact, this heparin assisted, ligand-induced dimerization of bFGFRs is required for activity. Poly(sodium 4-styrenesulfonate-co-poly(ethylene glycol) methyl ether methacrylate) (pSS-co-PEGMA) stabilizes bFGF. However, it does not promote the natural biological activity of heparin: to promote bFGF binding to its receptors. Studies of addition of bFGF into the cell medium did not stimulate the proliferation of the BaF3 cells (which express FGFR1 but lack heparan sulfate proteoglycans) unless heparin was included (FIG. 12A). The addition of bFGF-pSS-co-PEGMA, did not induce cell growth compared to when only bFGF was added. Furthermore, when bFGF and high excess of pSS-co- PEGMA (1 µg/ml) was added, the proliferation effect was not observed. This result showed that pSS-co-PEGMA polymer does not participate in receptor binding of bFGF to FGFRs as heparin does. Thus pSS-co-PEGMA does not bind to and activate the receptor. In some embodiments, the new heparin mimicking polymer can induce the dimerization and uptake the FGFRs. This polymer, when conjugated to bFGF, will result in a growth factor that is more active than the native protein.

In some embodiments, a trithiocarbonate end group is further modified or removed to reduce or eliminate cytoxicity.

In some embodiments, the heparin mimicking polymer is poly(sodium vinyl sulfonate) (pVS), as described in the example section. In some embodiments, the heparin mimicking polymer is pSS or pSS-co-PEGMA.

Synthesis of Conjugates

Synthesis of bFGF pVS Mono-Conjugate:

Multiple routes for the synthesis of bFGF-pVS monoconjugate can be used for conjugation to proteins. For example, in a first route (FIG. 15, Scheme 1), pVS was synthesized via RAFT polymerization from sodium vinyl sulfonic acid monomer using 2-(((ethylthio)carbonothioyl)thio)propanoic acid and V501 as CTA and initiator, respectively in acetate buffer at pH 5.2. Briefly, pVS with a trithiocarbonate end group will be subjected to aminolysis conditions with n-butylamine, then allowed to react with divinyl sulfone (DVS) in situ to give pVS with a vinyl sulfone end group. Alternatively, a pyridyl disulfide (PDS) could be installed by reacting the polymer with Aldrithiol™ upon aminolysis. Subsequently, the vinyl sulfone-pVS or PDS-pVS will be conjugated to bFGF via thiol-ene chemistry or reversible disulfide exchange. Any other end group and conjugation may also be utilized including binding to other natural amino acids such as amines and alcohols or unnatural amino acids and modifications.

The on-column conjugation conditions of bFGF to the polymers disclosed in this patent will be used to achieve mono-conjugates. Briefly, bFGF is diluted into 900 µl of 0.1 M PB pH 9.0 or D-PBS+1 mM EDTA, and loaded onto a hand-packed 1 ml-heparin Sepharose Column®. Vinyl sulfone-pVS or PDS-pVS is dissolved in 900 µl of 0.1 M PB pH 9.0 or D-PBS+1 mM EDTA respectively, and loaded onto the column. The column is allowed to incubate at 4° C. for 16 hours. The unconjugated polymers, and weakly bound bFGF are washed off the column with 2×6 ml of 0 M NaCl D-PBS, and 1×3 ml of 0.5 M NaCl D-PBS, respectively. The conjugate is eluted off the column using 2×6 ml of 2 M NaCl D-PBS. To purify the conjugate, the 2M NaCl fraction is subjected to dialysis against D-PBS using MWCO 26,000 tubing for 12 hours at 4° C., then washed for 10 cycles using a CentriPrep® centrifugal membrane MWCO 30,000 with D-PBS at 12.0 rcf for 8 minutes/cycle. The collected conjugate is then characterized by Western blot and ELISA.

In another route (FIG. 16, Scheme 2), a protein reactive group, namely PDS, is incorporated into the CTA, ethyl (1-oxo-1-((2-(pyridin-2-yldisulfanyl)ethyl)amino)propan-2-yl) carbonotrithioate. However, since this CTA is not compatible for aqueous RAFT polymerization, a different polymerization system will be employed. Mori and co-workers showed that bulk RAFT polymerization of neopentyl ethenesulfonate (NES) was controlled using a dithiocarbonate CTA and AIBN as the initiator, and deprotection of poly(neopentyl ethenesulfonate) (pNES) was feasible to obtain pVS (Mori et al., 2010). In our proposed synthetic route shown in Scheme 2, the NES monomer has been synthesized in one step to give 55-60% yield. Synthesis of pNES can be accomplished via RAFT polymerization in the presence of the proposed CTA. The resulting polymer will contain a PDS and a trithicarbonate as end groups. Upon deprotection of the neopentyl ester groups by refluxing pNES with LiBr in 2-butanone and subsequent subjecting to stirring with Na+ Dowex™ ion exchange resins, the desired functionalized pVS will be obtained. The polymer is then readily conjugated to bFGF via disulfide exchange using similar procedure as described above. Any other protecting group or associated positive ion may be utilized.

As depicted, the PDS end group on pVS could be modified into a vinyl sulfone to form irreversible conjugate with bFGF (FIG. 16, Scheme 2). Preliminary data showed that treating a model polymer poly(ethylene glycol) methyl ether acrylate (pPEGA, synthesized using the same CTA) with 0.5 molar equivalent of dithiothreitol (DTT) in 0.1 M PB pH 6.5 successfully reduced the PDS end group selectively within 10 minutes. Upon quick removal of the side product (pyridine-2-thione) and the unreactive DTT via centriprep, the polymer was subjected to stirring with DVS (neat) for one hour at 23° C. to give vinyl sulfone-pPEGA quantitatively with good polydispersity index (PDI). Conjugation of the resulting polymer to a model protein, bovine serum albumin, gave near complete conjugation. Therefore, this synthetic route will be exercised on pVS to produce irreversible bFGF-pVS conjugate via thiol-ene chemistry. Any other polymerization method, end group or conjugation chemistry may be used.

Synthesis of Protein Dimers bFGF-pVS-bFGF:

In some embodiments, bFGF dimers are linked by a polymer, which can be more efficacious than monomers. Dimers linked with the polymer that binds to the receptor discussed above will be extremely active. In short, the polymer tether will present the bFGF in a configuration (i.e., dimer) that is optimal for activation of the receptor. In addition, a heparin mimicking polymer should stabilize the attached growth factors. Finally, the polymer will additionally act to stabilize the tetrameric complex of bFGF with its receptors, as does heparin. Several synthetic approaches for preparing dimers are disclosed below. The first example is the synthesis of a bFGF-PEG-bFGF, which has not yet been reported. The planned synthesis of heparin mimicking polymer dimer conjugates is also disclosed.

Bis-vinyl sulfone modified PEG has been used to create protein dimers via reaction with a surface exposed free cysteine at neutral to basic pH; purification of monoconjugate and unmodified protein from the protein dimer has been achieved with anion and cation exchange chromatography. However, this approach has not been utilized to make bFGF dimers. We have utilized this approach to create a PEG-linked bFGF protein dimer through step-wise reaction on a heparin column. In addition, PEG can also be modified on both sides with maleimide, aminooxy, or pyridyl disulfide, or any other group that reacts with the protein. Bis-maleimide and bis-pyridyl disulfide PEGS are commercially available. In some embodiments, 8-arm PEG is modified with amino-oxy functionalities in order to absorb bFGF onto surfaces to increase cell adhesion. In some embodiments, this method is applicable to linear PEG. Conjugations with these bis-modified PEGS can be performed step-wise on a heparin column, in heparin-resin slurry, or in the presence of excess free heparin.

Synthesis of Vinyl Sulfone-PEG-Vinyl Sulfone:

This procedure was adapted from the work of Lutolf and Hubbell which functionalized 8-arm PEG with vinyl sulfone. PEG (0.5 g, 0.08 mmol) was dissolved in 30 mL dichloromethane (DCM). NaH (20 mg, 0.83 mmol) was added. After hydrogen evolution, divinyl sulfone was added quickly. The reaction was allowed to stir under inert atmosphere at room temperature for three days. The reaction solution was neutralized with acetic acid and filtered. The polymer solution was then precipitated into cold diethyl ether 15 times after which the solution was washed with saturated NaCl, extracted into DCM, and precipitated 5 more times. After drying under vacuum overnight, the polymer was analyzed by NMR and 85% bis-functionalization was observed by comparison of the vinyl sulfone peaks to the PEG peaks.

Scheme 3: Synthesis of vinyl sulfone-PEG-vinyl sulfone

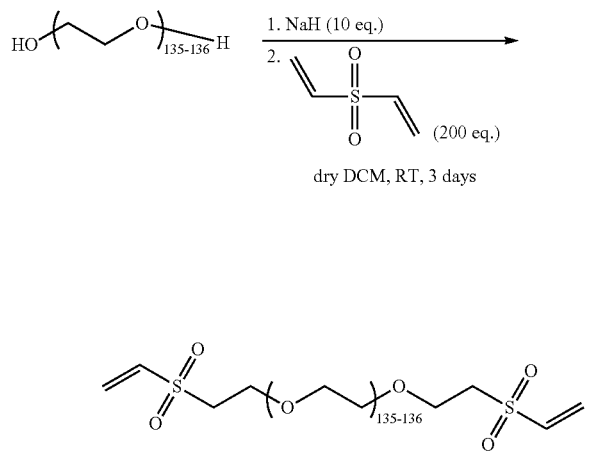

Synthesis of bFGF-PEG-bFGF:

bFGF (41 µg, 2.56 nmol) was diluted to 900 µL in D-PBS pH 8.5, 0 M NaCl, 1 mM EDTA and loaded onto a heparin column at 4° C. 100 equivalents of 6 kDa bis-vinylsulfone PEG (1.6 mg, 0.26 mmol) was dissolved in 900 µL D-PBS pH 8.5, 0 M NaCl, 1 mM EDTA and loaded onto the column at 4° C. and incubated for 12 hours, the flow-through volume was collected for analysis.

To remove free polymer from the column, 6 mLs of D-PBS pH 7.4, 0 M NaCl was rinsed through the column and collected for analysis. 900 uL D-PBS pH 8.5, 0 M NaCl, 1 mM EDTA was also run through the column to switch the pH. bFGF (41 µg, 2.56 nmol) was diluted to 900 µL in D-PBS pH 8.5, 0 M NaCl, 1 mM EDTA and loaded onto the column at 4° C. and incubated for 6 hours. 3 mLs D-PBS pH 7.4, 0.5 M NaCl, 1 mM EDTA was rinsed through the column to release loosely bound bFGF. The volume was collected for analysis. 2×6 mLs D-PBS pH 7.4, 2 M NaCl, 1 mM EDTA was rinsed through the column to release the conjugates and bFGF. All collected volumes were rinsed with D-PBS pH 7.4 and concentrated using a CentriPrep® 3 kDa MWCO centrifugal unit at 12 rcf for 10 minutes/cycle.

The 2 M fraction was then transferred to 30 kDa MWCO centrifugal unit in order to remove unconjugated bFGF for 10 cycles, and the filtrate was collected for analysis. The 2 M fraction was then placed in 26 kDa MWCO dialysis tubing and dialyzed against D-PBS pH 7.4 for 12 hours at 4° C. The 2 M fraction was then concentrated down as before. All fractions were analyzed by ELISA and samples with greater than 2% of the total bFGF in all samples were analyzed by Western Blot. Bands indicating bFGF that was conjugated to PEG through a non-reducible, covalent, S—C bond (bFGF-PEG and bFGF-PEG-bFGF) were observed under reducing conditions (FIG. 14, lane 5). Purification of PEG-bFGF-PEG from monoconjugate and unmodified bFGF will accomplished by FPLC utilizing either an anion, cation, or heparin column.

Synthesis of Bisfunctionalized pVS:

The synthetic approaches to synthesize bisfunctionalized pVS are shown in Scheme 5. Utilizing the pVS that contains a PDS and a trithiocarbonate functional groups (shown in FIG. 16, Scheme 2), a second PDS can be installed by modifying the trithiocarbonate group. In a model study, the bisfunctionalized PDS-pSS-co-pPEGMA-PDS was synthesized by performing aminolysis on the trithiocarbonate-terminated monofunctionalized PDS-pSS-co-pPEGMA in the presence of excess Aldrithiol™. Upon dialysis to purify the bisfunctionalized copolymer, $^1$H NMR, GPC and UV-Vis analyses confirmed a near quantitative conversion. More importantly, no coupling product was detected; PDI remained narrow. Because of its straightforwardness and efficiency, this synthetic method is promising to prepare PDS-pVS-PDS.

Alternatively, both of the PDS and trithiocarbonate end groups of pVS can be modified into vinyl sulfone functional groups. In this approach, instead of excess Aldrithiol™, excess DVS will be added to trap the thiolates formed by aminolysis. If this approach is not high yielding, excess DTT can be used to reduce the PDS and the trithiocarbonate groups. Upon removal of the excess DTT, the polymer will be subjected to neat DVS to form bisfunctionalized vinyl sulfone-pVS-vinyl sulfone. This approach was shown to be effective and high yielding on trithiocarbonate-terminated PDS-pPEGA. Again, any approach to make the material with any end group that can bind covalently to the bFGF may be utilized.

Scheme 5: Synthesis of bisfunctionalized pVS

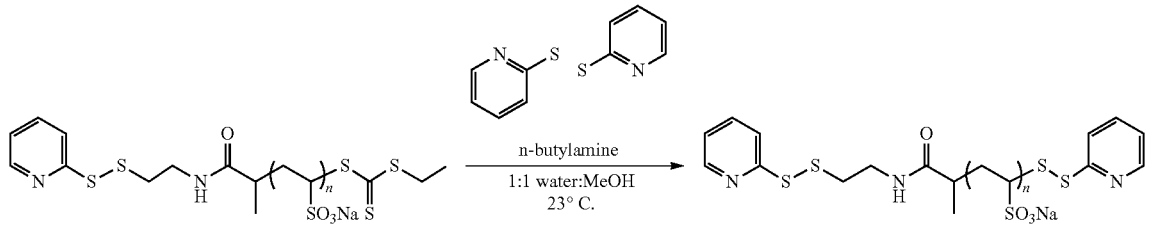

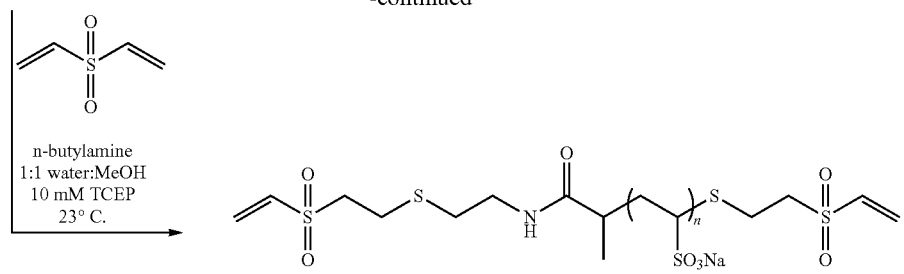

Synthesis of bFGF-pVS-bFGF:

The synthesis of bFGF dimer (bFGF-pVS-bFGF) is proposed over two steps (FIG. 18, Scheme 6). First, bFGF is allowed to conjugate to either PDS-pVS-PDS or vinyl sulfone-pVS-vinyl sulfone using the on-column technique as described above. This method has been shown to produce mostly bFGF-pVS mono-conjugate. Once the excess polymer is removed, the mono-conjugate will be re-subjected to more bFGF in the presence of 0.5 molar equivalent of heparin in D-PBS to induce the formation of bFGF-pVS-bFGF. This conjugate is more active than the native protein, similar to the reactivity of pVS-bFGF monoconjugates.

Applications

For the past three decades, PEG conjugates have been widely utilized as biologic drugs; yet these conjugates still suffer from environmental instability issues, and often require addition of large concentrations of excipients. It is disclosed herein that by careful design of a polymer to mimic a natural polysaccharide, a protein that is normally very unstable can be rendered stable to numerous stresses that would typically inactivate the protein. Since bFGF has far reaching biological activity from wound healing to cardiac repair, and as a result is an important drug target, this stable construct may be useful therapeutically. Indeed, prior results have demonstrated that clinical trials of bFGF in wound healing have failed, potentially due to issues with stability. The results also suggest that the heparin mimicking polymer-bFGF conjugate does not require restrictive storage temperatures (freezing) or require loading of excipients as does the native protein. This is important when considering at-home patient use of any clinically relevant biologic, where storage in a freezer until just before use is not desirable and may not be feasible.

Interestingly, the bFGF-pSS-co-PEGMA conjugate showed superior stability compared to bFGF-pPEGMA. The pPEGMA conjugate was significantly degraded after exposure to storage or heat. With exposure to trypsin and acid, the experimental set-up requires keeping samples refrigerated rather than frozen. Thus, it cannot be ruled out that the typical testing conditions for these stressors, i.e., keeping the samples at 4° C. for 16 hours, caused the degradation rather than the enzyme or acidic conditions. Yet, the data clearly show that the heparin mimicking conjugate is superior to the PEGylated one, in that it can be heated or stored in the fridge without loss of activity, and that the conjugate is stable to acidic conditions that may be found, for example, in wounds. The conjugate is also stable to at least one proteolytic enzyme, which is a typical advantage of a PEGylated conjugate.

As disclosed herein, the resulting conjugate outperformed addition of the same equivalent of non-conjugated polymer or heparin to bFGF. This suggests that the close proximity of the heparin-mimicking polymer protected the bFGF from denaturation. This result is also useful because it shows that a very small amount of polymer can be used for stabilization. A large concentration of heparin stabilized the protein as expected. However, heparin itself has significant cross bioactivity, and thus adding large amounts of the polysaccharide in vivo is not desirable.

Other heparin-binding proteins bind to heparin for stabilization. For example, non-conjugated PEG-polyanions (pentosan polysulfate and dextran sulfate) have been utilized to increase stability of a related protein keratinocyte growth factor-2 (KGF-2); these complexes are non-covalent. Non-covalent conjugates are potentially not useful in vivo because of the likelihood of detachment of the polymer upon dilution before reaching target sites. Thus, the strategy described herein, whereby a heparin mimicking polymer is covalently yet reversibly attached to the protein, could also be used to stabilize other heparin binding growth factors such as KGF-2.

Although the inhibition assay indicated that the bFGF-heparin mimicking polymer conjugate triggered HDF proliferation via the same signal transduction pathway as native bFGF, the heparin-mimicking polymer did not participate in receptor binding as does heparin. Heparin added at high concentrations to normal cells can inhibit the activity of these cells, and this has been proposed to occur by competition with the HS. That the pSS-co-PEGMA mimicked heparin in that it bound to bFGF to stabilize it, but did not participate in receptor binding, could be advantageous: high concentrations of the polymer may not inhibit cellular activity as heparin does.

Advantageously, the invention can be practiced in any setting where bFGF is utilized. In place of addition of bFGF, the bFGF-heparin mimicking polymer conjugate would be utilized. In some embodiments, various embodiments of invention can include, but are not limited to, as a topical treatment for a variety of clinical settings including wound healing, as a injectable therapeutic for a variety of diseases including bone repair and neuron regeneration, as cell culture additives for stem cell self renewal, and for use as a reagent in research settings.

In some embodiments, different molecular weights of heparin mimicking polymers, such as pSS-co-PEGMA or pVS, and different sulfonated and sulfated polymers can be used.

In some embodiments, the heparin mimicking polymer has a molecular weight of about 5 kDa or higher, 10 kDa or higher, 12 kDa or higher, 15 kDa or higher, 18 kDa or higher, 20 kDa or higher, 22 kDa or higher, 25 kDa or higher, 28 kDa or higher, 30 kDa or higher, 32 kDa or higher, 35 kDa or higher, 38 kDa or higher, 40 kDa or higher, 42 kDa or higher, 45 kDa or higher, 48 kDa or higher, 50 kDa or higher, 55 kDa or higher, 60 kDa or higher, 65 kDa or higher, 70 kDa or higher, 80 kDa or higher, 90 kDa or higher, or about 100 kDa or higher.

In some embodiments, different heparin binding proteins are utilized, e.g., keratinocyte growth factor (KGF). In some embodiments, the invention conjugate can be used for stem cell self renewal for cell therapy, e.g., regenerative medicine such as wound healing.

EXAMPLES

A cysteine-reactive heparin mimicking polymer pSS-co-PEGMA was prepared via RAFT polymerization. Conjugation of the polymer to bFGF via disulfide exchange was accomplished using an on-column technique to produce a mono bFGF-pSS-co-PEGMA conjugate. The conjugate exhibited significantly enhanced stability against heat, mild and harsh acidic conditions, storage, and proteolytic degradation compared to native bFGF and the analogous bFGF-pPEGMA conjugate. The polymer targeted the same receptor as unmodified bFGF. While one equivalent of polymer or heparin did not stabilize the growth factor, the same amount of conjugated polymer did. The results together demonstrate that the strategy of conjugating heparin mimicking polymers to bFGF is valuable as a means to stabilize this clinically important protein.

The examples describe stabilization of bFGF by the heparin mimicking polymer conjugate was demonstrated. Requirement to covalently conjugate the polymer was shown. The polymer was shown to be non-cytotoxic. The receptor activation was shown to be the same as bFGF.

Chemicals and reagents were purchased from Fisher or Sigma-Aldrich unless indicated otherwise. bFGF-CF (carrier-free) and ELISA Development DuoSet® kits were purchased from R&D Systems. Heparin was purchased from PromoCell. Rabbit anti-fibroblast growth factor basic antibody and Goat anti-rabbit IgG-HRP conjugate for Western blot were purchased from CALBIOCHEM and Bio-rad, respectively. Human Dermal Fibroblast cells were purchased from PromoCell. BaF3 cells that express FGFR1 (FR1C-11) were kindly provided by Prof. David Ornitz (University of Washington, Saint Louis). Media and supplements for cell culture were either purchased from Promo-Cell, Lonza or Invitrogen. PD173074 was purchased from Cayman Chemical. LIVE/DEAD® viability/cytotoxicity assay kit and CellTiter-Blue® cell viability assay were obtained from Invitrogen and Promega, respectively. HiTrap™ Heparin HP 1 ml was purchased from GE Healthcare. Poly(sodium 4-styrenesulfonate) and poly(ethylene glycol) standards were purchased from Polymer Laboratories. Merck 60 (230-400 mesh) silica gel was used for column chromatography. Dichloromethane was distilled over $CaH_2$ prior to use. 2,2'-azobisisobutylonitrile (AIBN) was recrystallized twice from ethanol and dried prior to use. Copper bromide (CuBr) was purified by stirring in glacial acetic acid for 12 hours, filtering and rinsing with ethanol and diethyl ether, and drying under vacuum. 2-(ethyl trithiocarbonate)propionic acid was synthesized as previously reported.[1]. The 4-styrene sulfonic acid, sodium salt hydrate monomer was pre-treated with $Na^+$-activated DOWEX 50WX8 200-400 mesh resin prior to use. 3-(Pyridin-2-yldisulfanyl)propyl-2-(ethylthiocarbonothioylthio) propanoate and 2-(Pyridin-2-yldisulfanyl)ethanol were synthesized as previously described.

$^1H$ and $^{13}C$ NMR spectroscopy were performed on an Avance DRX 400 or 500 MHz spectroscopy instrument. Infrared spectroscopy was performed on a PerkinElmer FT-IR equipped with an ATR accessory. UV-Vis analyses were performed on a Biomate 5 Thermo Spectronic spectrometer. Gel permeation chromatography (GPC) was conducted on a Shimadzu HPLC system equipped with a refractive index detector RID-10A, one Polymer Laboratories PLgel guard column, and two Polymer Laboratories PLgel 5 µm mixed D columns. DMF containing 0.10 M LiBr at 40° C. was used as the eluent and near-monodisperse poly(methyl methacrylate) standards from Polymer Laboratories were used for calibration at 0.6 ml/min. Chromatograms were processed using the EZStart 7.2 chromatography software. Gel electrophoresis was performed using NuPAGE® 4-12% Bis-tris gels and 2-(N-Morpholino) ethanesulfonic acid sodium dodecyl sulfate (MES SDS) buffer (Invitrogen, Grand Island). ELISA assay result was read on the ELX800 Universal Microplate Reader (Bio-Tek Instrument, Inc., Winooski) with $\lambda$=450 nm and 630 nm for signal and background respectively. Western blot was developed on a FluoroChem® FC2 System version 3.2 (Cell Bioscience, Santa Clara). ImageQuant™ program was used to analyze gel images. Fluorescent signals from CellTiter-Blue® assay were read using SpectraMax M5 microplate reader (Molecular Devices, Sunnyvale). Fluorescent images of the cells were acquired on an Axiovert 200 microscope equipped with an AxioCam MRm camera and FluoArc mercury lamp (Carl Zeiss, Thornwood). NIH Image J software was used to assist cell counting. Mass spectrometry analysis of the conjugates was done on the Electrospray Ionization-Gas-phase electrophoretic mobility molecular analyzer (ESI-GEMMA) instrument (TSI Inc., Shoreview), which consists of an ESI unit with a neutralizing chamber, a nano differential mobility analyzer (DMA) model 3085 and model 3071A, and a condensation particle counter (CPC) type 3025. The detailed description of the instrument and its settings are described elsewhere.[2] Peak Fit (version 4.12, Systat Software) was used to analyze the GEMMA spectra.

Synthesis and Characterization of pSS-Co-PEGMA.

Reversible addition-fragmentation chain transfer (RAFT) polymerization was employed to copolymerize 4-sulfonated styrene (SS) and polyethylene glycol methyl ether methacrylate (PEGMA) (see FIG. 1a). 3-(Pyridin-2-yldisulfanyl) propyl-2-(ethylthiocarbonothioylthio) propanoate was synthesized as previously described[3] and used as the chain transfer agent (CTA) for RAFT copolymerization of SS and PEGMA. The polymerization was performed with an initial feed ratio of [SS]:[PEGMA]:[CTA]:[AIBN]=90:30:1:0.5 using standard Schlenk techniques. The CTA (60 mg, 0.152 mmol), SS (2.83 g, 13.72 mmol), PEGMA (1.31 ml, 4.57 mmol), and AIBN (12.52 mg, 0.076 mmol) were dissolved in 2 ml of Milli-Q water and 2 ml of DMF in a Schlenk tube.

In a different experiment, the polymerization was performed with an initial feed ratio of [SS]:[PEGMA]:[CTA]:[AIBN]=105:30:1:0.5 using standard Schlenk techniques. The CTA (30 mg, 0.08 mmol), SS (1.65 g, 8.00 mmol), PEGMA (0.65 ml, 2.29 mmol), and AIBN (6.26 mg, 0.038 mmol) were dissolved in 5 ml of Milli-Q water and 5 ml of DMF in a Schlenk tube.

The system was sealed and subjected to four freeze-pump-thaw cycles before immersion in a 70° C. oil bath. Aliquots were removed at predetermined time points and diluted in $D_2O$ or DMF for $^1H$ NMR or GPC analysis, respectively. Conversions were calculated by $^1H$ NMR using the sum of the integral values of vinylic protons of SS monomer and PEGMA monomer at 5.9 ppm and 6.2 ppm, respectively, and the sum of integral values of the regions where the monomer protons and the growing polymer protons overlap (7.8-6.3 ppm for SS and 4.0-3.2 ppm for PEGMA). The polymerization was stopped at 83% conversion.

The polymer was purified by dialysis first with 1:1 Milli-Q water:MeOH to remove residual monomer followed by dialysis with pure Milli-Q water (MWCO 8000) and lyophilized to remove solvent. To remove the trithiocarbonate end group, the resulting polymer (17.6 mg, 6.5×10$^{-4}$ mmol) was combined with excess AIBN (6.0 mg, 0.036 mmol) in 1.5 ml of 1:1:1 v/v/v DMF:Dioxane:MeOH in a Schlenk tube. The system was degassed by three cycles of freeze-pump-thaw and stirred for 4 hours at 70° C. The resulting PDS-pSS-co-PEGMA was purified by dialysis in 1:1 water:MeOH (MWCO 3500). UV-vis spectrophotometry was used to monitor the disappearance of the trithiocarbonate group ($\lambda$=309 nm). $\delta$ $^1$H NMR 500 MHz (D$_2$O): 8.6 (1H, CHN), 8.4-8.0 (2H, NCCHCH), 8.0-6.0 (Na$^+$SO$_3^-$ C$_6$H$_4$ side chains), 4.4-2.8 (PEGMA side chains), 2.8-0.0 (polymer backbone). IR (cm$^{-1}$): 3448, 2924, 1718, 1647, 1453, 1410, 1181, 1122, 1035, 1008, 947, 832, 773, 671. The $M_n$=26.1 kDa by NMR, 25.0 kDa by GPC, PDI=1.14 by GPC. See FIGS. 1b and c for $^1$H NMR and GPC spectra, respectively. The results demonstrate that the polymer was made, the end group was intact, and the polymer was well defined.

Synthesis and Characterization of PDS-pPEGMA.

Figure 2A:
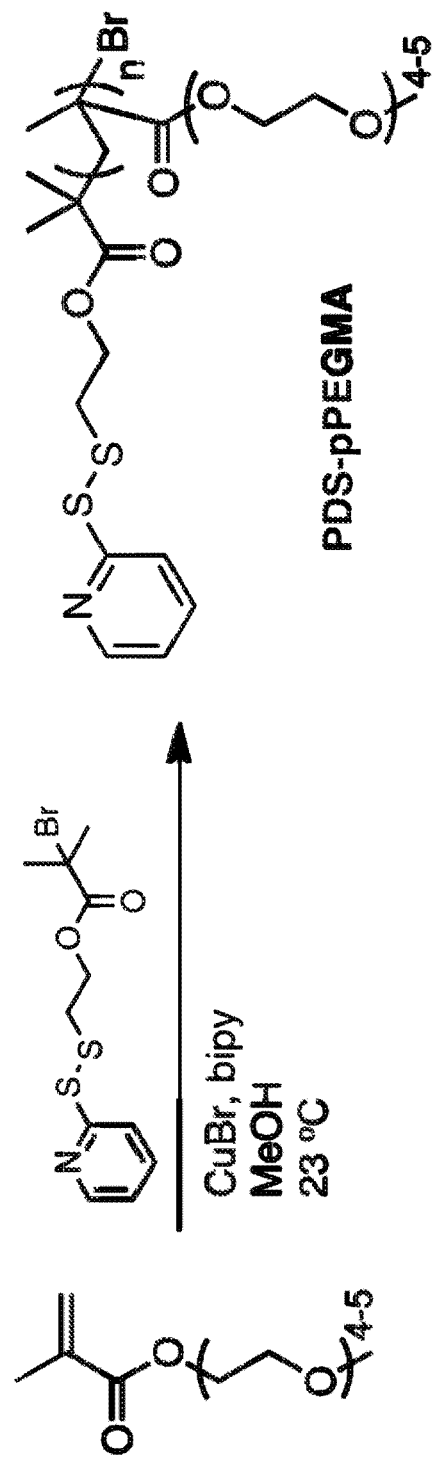
FIGS. 2A-2D depict exemplary synthesis and characterization of PDS-pPEGMA. (A) Synthesis scheme of PDS-pPEGMA; (B) GPC trace of the polymer in DMF 0.1 M LiBr; (C) $^1$H NMR spectrum of the polymer in CDCl$_3$; (D) FT-IR spectrum of the polymer; (E) GEMMA spectrum of the polymer taken in 20 mM Ammonium Acetate (arrow, EMD=4.73 nm, d=0.69 g/cm$^3$ calculated using formula: $d=MW/(N_a*EMD^3*\pi/6)$.
Figure 2B:
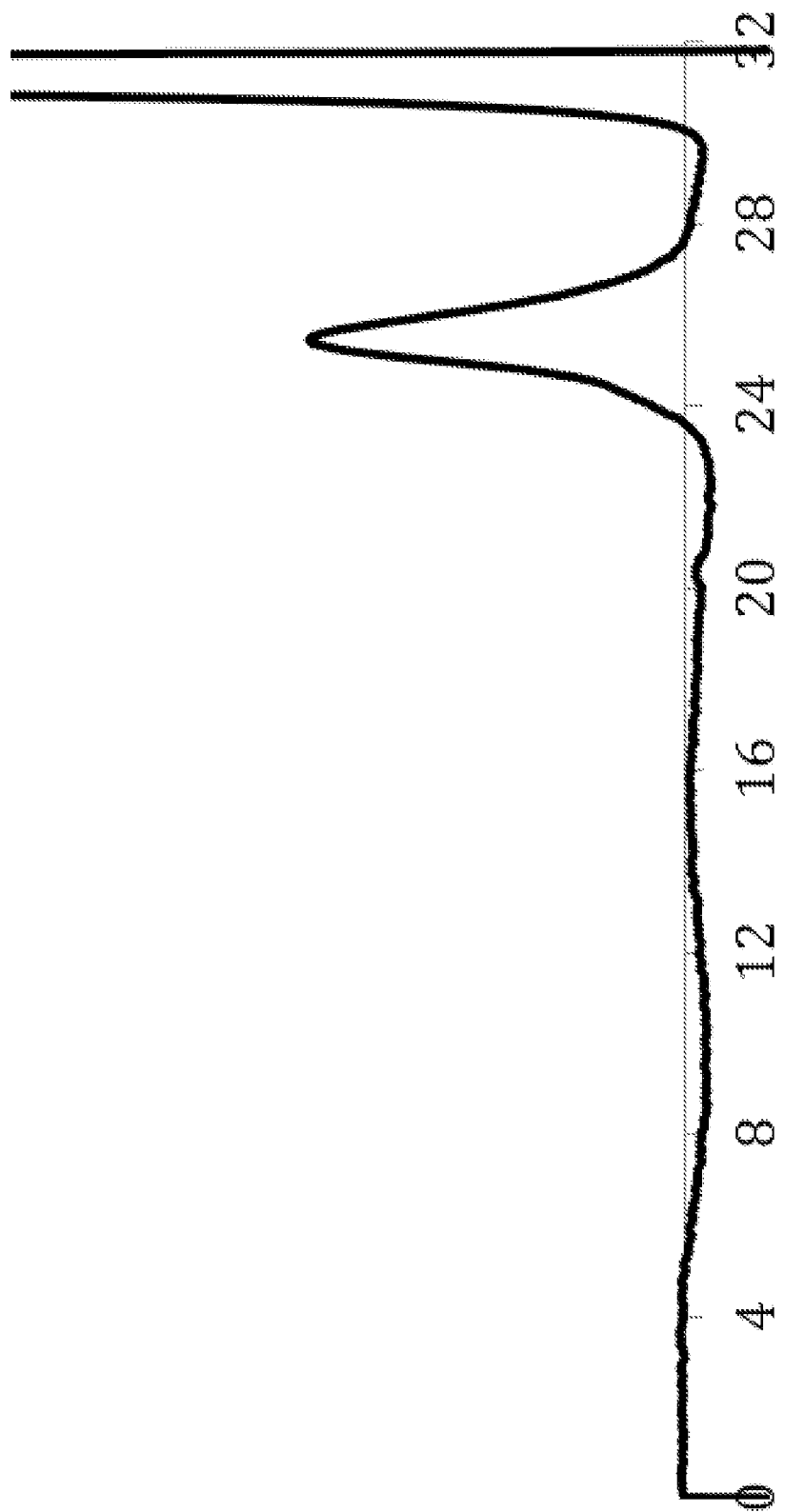
Figure 2C:
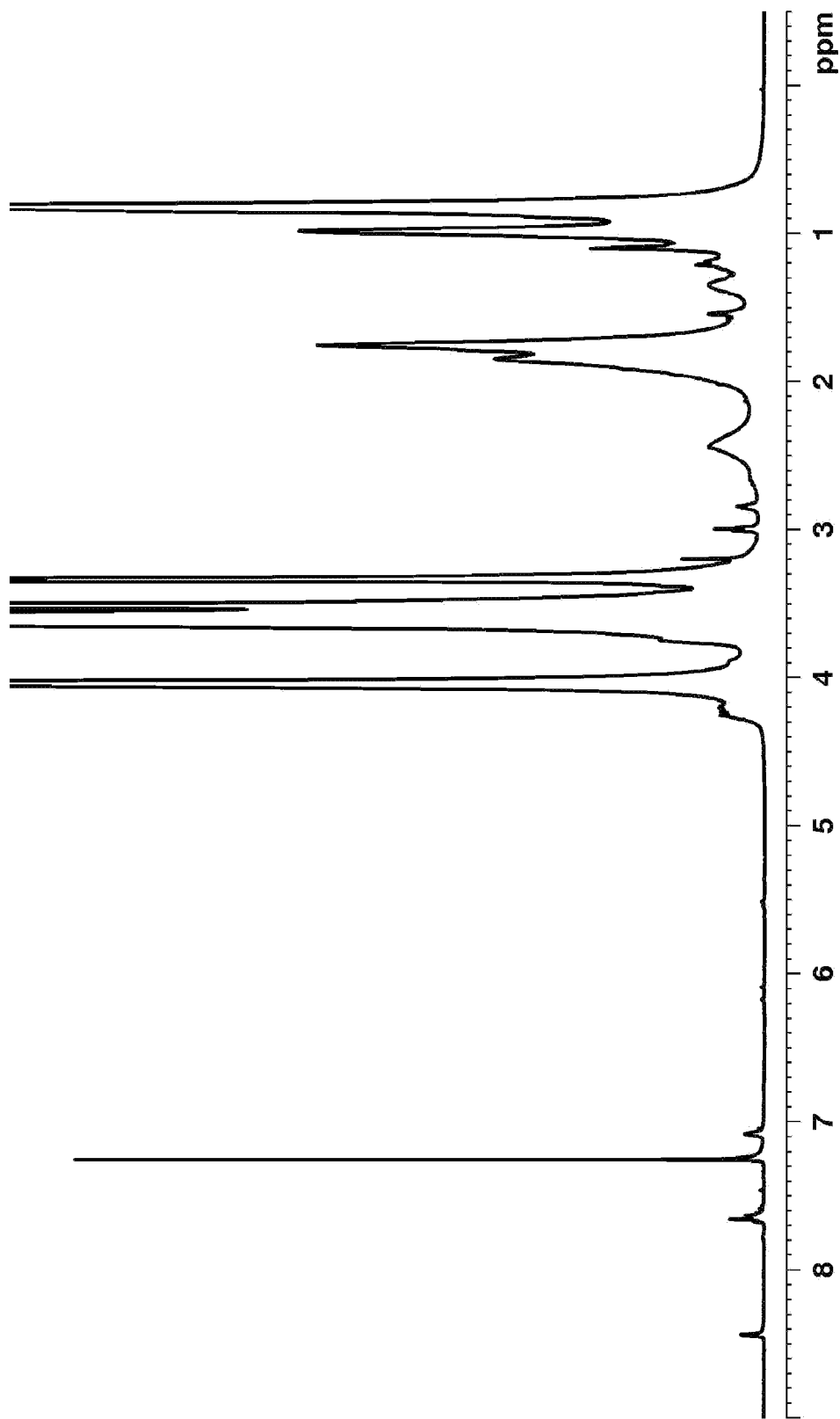
Figure 2D:
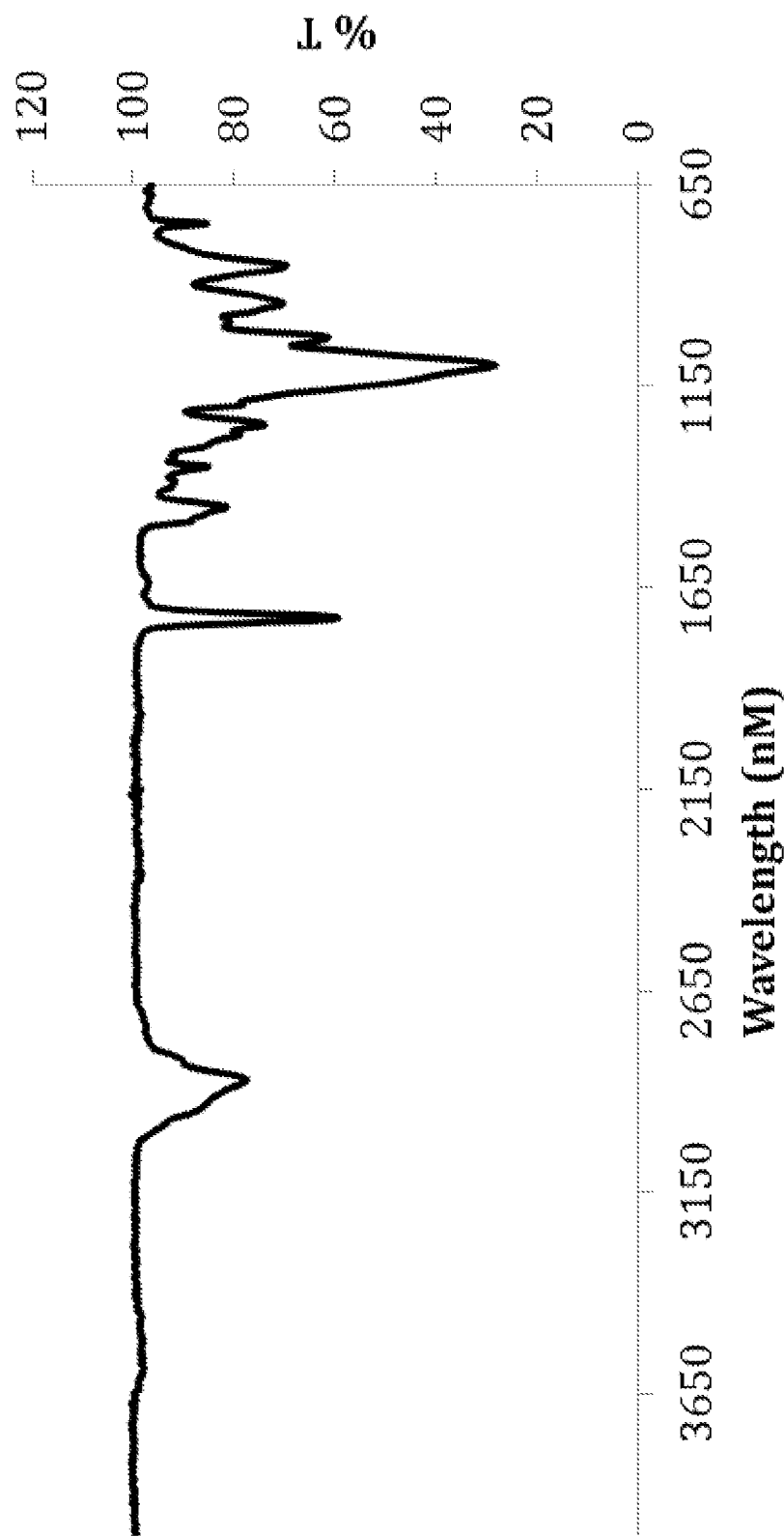

Atom transfer radical polymerization (ATRP) was employed to synthesize PDS-pPEGMA (see FIG. 2a). An ATRP initiator, 2-(pyridin-2-yldisulfanyl)ethyl 2-bromo-2-methylpropanoate was used. In a Schlenk tube, PEGMA (856 mg, 2.85 mmol), 2-(pyridin-2-yldisulfanyl)ethyl 2-bromo-2-methylpropanoate (30 mg, 0.09 mmol), and 2 ml of MeOH were combined, sealed, subjected to five cycles of freeze-pump-thaw. In a two-neck round bottom flask, CuBr (51.2 mg, 0.36 mmol) and 2, 2'-bipyridine (111.5 mg, 0.71 mmol) were combined and subjected to 4 cycles of vacuum-Ar refill. An amount of 2 ml of degassed MeOH was added to the two-neck round bottom flask, and 0.5 ml of the mixture was transferred to the Schlenk tube to start the polymerization. After 6 hours, air was bubbled through the reaction to stop the polymerization. The polymer was purified by dialysis against MeOH with 10 mM EDTA first to remove Cu$^{II}$, then against MilliQ-water (MWCO 3500). $\delta$ $^1$H NMR 500 MHz (D$_2$O): 8.4 (1H, end group NCH), 7.7-7.6 (2H, end group NCCHCH), 7.0 (1H, end group NCHCH), 4.2-2.9 (PEGMA side chains), 3.0 (2H, end group SSCH$_2$), 2.8 (2H, last CH$_2$ in the polymer backbone), 2.7-0.0 (polymer backbone). IR (cm$^{-1}$): 3527, 2873, 1726, 1451, 1350, 1245, 1099, 1029, 945, 852, 747. The $M_n$=23.0 kDa by NMR, 11.1 kDa by GPC and PDI=1.13 by GPC. See FIGS. 2b and c for GPC and $^1$H NMR spectra, respectively. The results demonstrate that the polymer was made, the end group was intact, and the polymer was well defined.

Figure 3A:
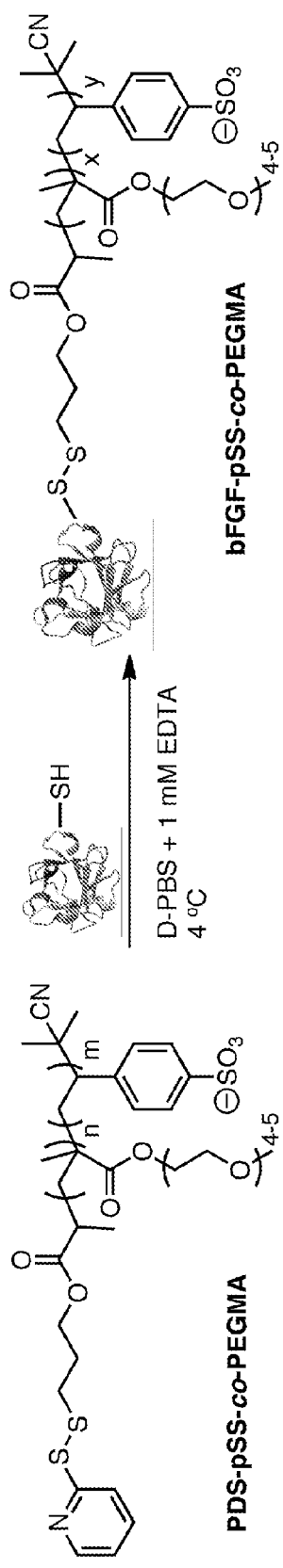
FIGS. 3A-3C depict an exemplary embodiment of the present invention, conjugation of pSS-co-PEGMA to bFGF and characterization. (A) Synthesis scheme of bFGF-pSS-co-PEGMA; (B) Western blots of bFGF-pSS-co-PEGMA from SDS-PAGE (left) and Native PAGE (right), lane 1: bFGF-pSS-co-PEGMA under reducing condition, lane 2: bFGF-pSS-co-PEGMA under nonreducing condition, lane 3: bFGF under nonreducing condition; (C) ESI-GEMMA spectra of bFGF (top), bFGF-pSS-co-PEGMA (bottom, arrow, EMD=5.43 nm, d=0.78 g/cm$^3$, MW$_{calculated}$=39 kDa, MW$_{theoretical}$=42 kDa) in 20 mM ammonium acetate.
Figure 8D:
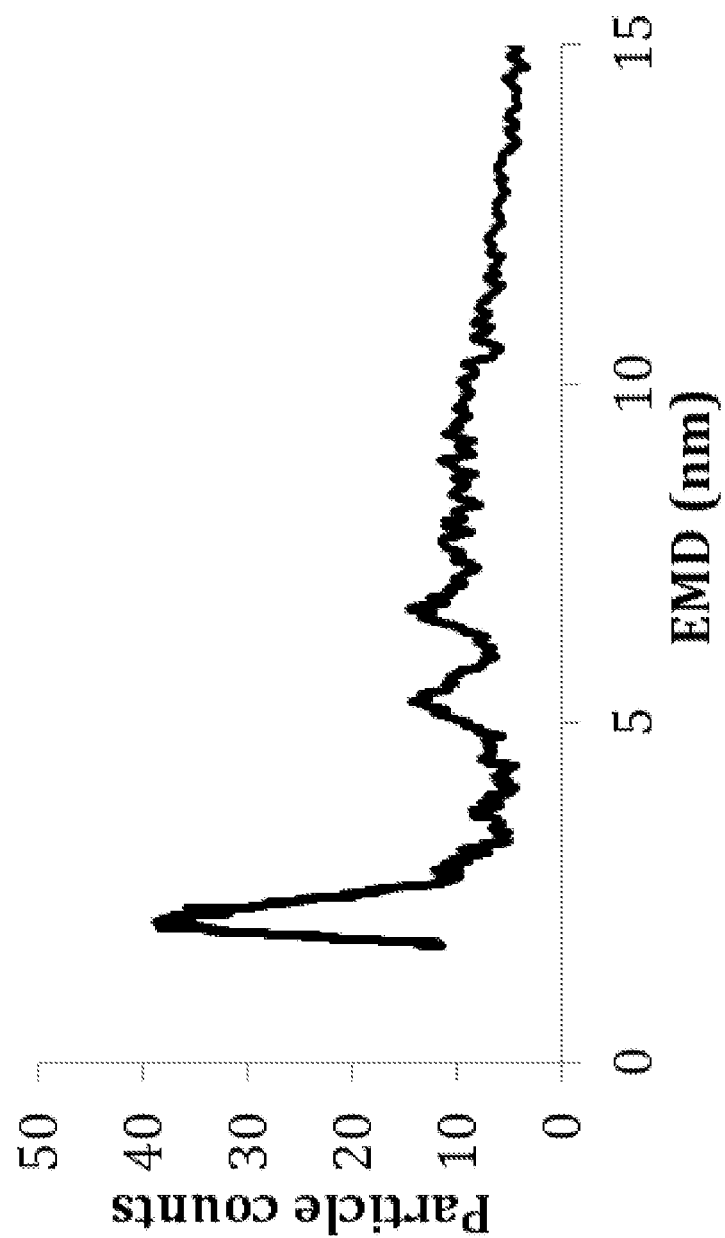
FIGS. 8A-8D depict exemplary synthesis and characterization of bFGF-pPEGMA conjugate. (A) Synthesis scheme; (B) Western blot of bFGF-pPEGMA 21k, lane 1: bFGF-pPEGMA under reducing conditions, lane 2: bFGF-pPEGMA under non-reducing conditions, lane 3: bFGF under non-reducing conditions; (C) Western blot of bFGF-pPEGMA40k (similar assignments); (D) GEMMA spectrum of bFGF-pPEGMA21k (EMD=5.3 nm, d=0.64 g/cm$^3$, MW$_{calculated}$=30 kDa, MW$_{theoretical}$=39 kDa) in 20 mM ammonium acetate; and (E) GEMMA spectrum of bFGF-pPEGMA40k (EMD=6.1 nm, d=0.71 g/cm$^3$, MW$_{calculated}$=56 kDa, MW$_{theoretical}$=50 kDa) in 20 mM ammonium acetate.

Conjugation of PDS-pSS-Co-PEGMA or PDS-pPEGMA to bFGF (See FIG. 3a and FIG. 8a)

Figure 3B:
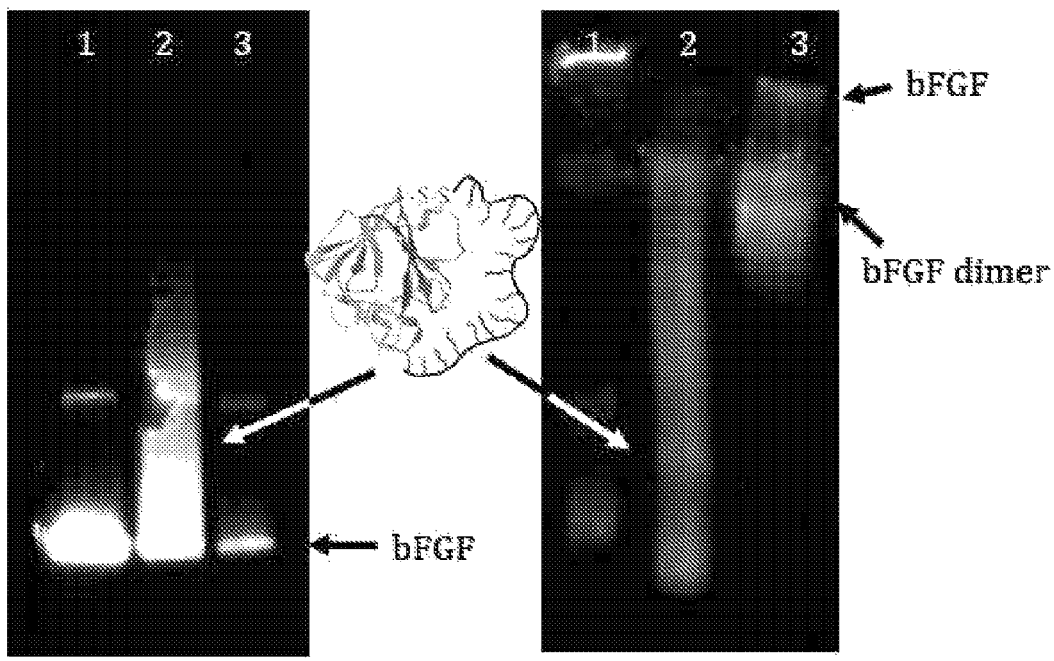
Figures 10A, 10B:
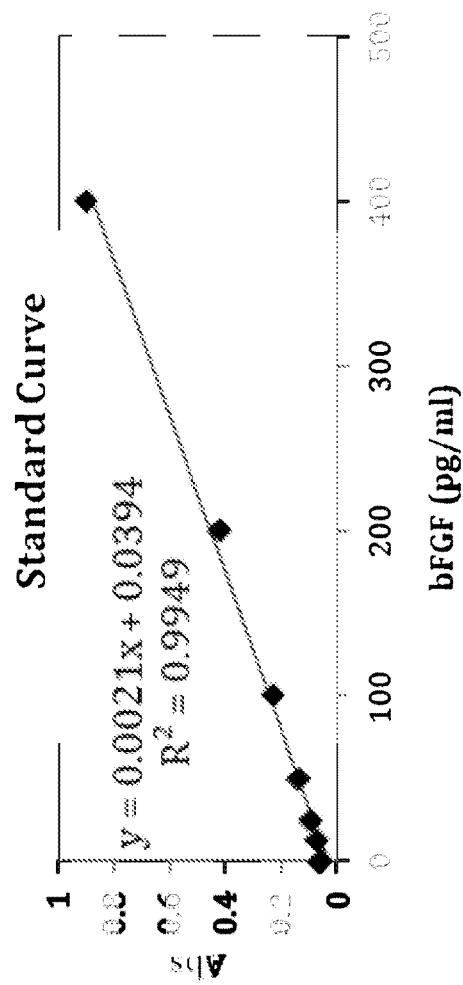
FIGS. 10A & 10B depict the on-column bFGF conjugation efficiency. Quantification of bFGF in the collected fractions from on-column conjugation was performed via ELISA. (A) The percent bFGF in the 2M NaCl fraction was calculated by the dividing the amount bFGF in the 2M NaCl fraction to the total amount of bFGF collected in all fractions. Percent yield was calculated by dividing the total bFGF collected in the 2M fraction to the original amount of bFGF used for conjugation. The concentrations were extracted from standard curve (B).
Figure 11:
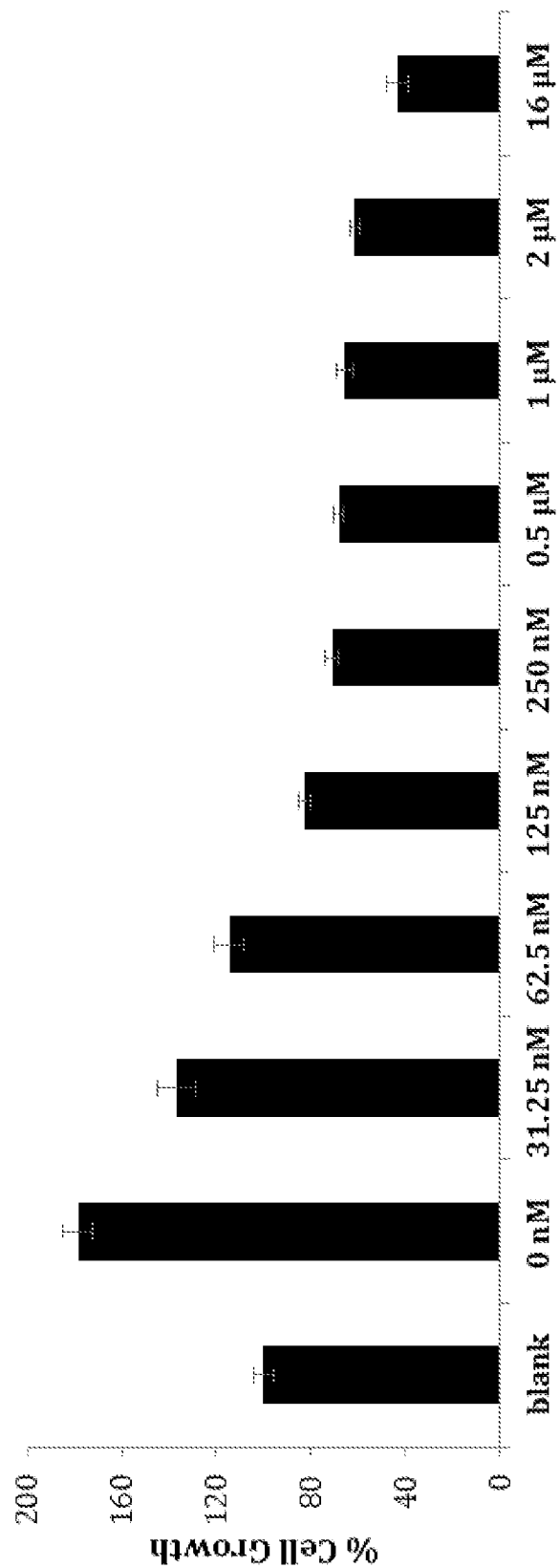
FIG. 11 depicts the exemplary results of screening analysis for optimum concentration of the inhibitor PD173074. Each sample group contained 1 ng/ml of bFGF except for the blank group. The x-axis shows increasing concentration of the PD173074 tested on HDF. The data was normalized to the percent cell growth in the blank.

An on-column conjugation technique was utilized to synthesize bFGF-pSS-co-PEGMA and bFGF-pPEGMA conjugates. Briefly, the conjugation was conducted by adding a polymer solution to heparin sepharose-bound bFGF prior to eluting with increasing salt in Dulbecco's phosphate buffer saline (D-PBS). In this way, the excess polymer was completely removed; typical yield of the isolated conjugate was 50% (see FIG. 10). Western blotting of SDS-PAGE and native PAGE (FIG. 3B and FIG. 8B, C) showed diffuse bands at higher molecular weight typical of protein-polymer conjugates. Furthermore, the bands corresponding to the conjugates disappeared and the signals corresponding to the unconjugated bFGF were more intense under reducing conditions, as expected for conjugates prepared with reversible disulfide bonds.

bFGF (25 µg, 1.6×10$^{-3}$ µmol) was diluted into 900 µl of D-PBS+1 mM EDTA+100 mM trehalose, and loaded onto a hand-packed 1 ml-heparin Sepharose Column®. PDS-pSS-co-PEGMA or PDS-pPEGMA (3.6 mg, 0.14 µmol) was dissolved in 900 µl of D-PBS+1 mM EDTA, and sometimes additionally with 100 mM trehalose, and loaded onto the column, the 900 µl of the flow-through volume was collected for analysis. The column was allowed to incubate at 4° C. for 16 hours. The unconjugated polymer, and weakly bound bFGF were washed off the column with 2×6 ml of 0 M NaCl D-PBS, and 1×3 ml of 0.5 M NaCl D-PBS, respectively. The conjugate was eluted off the column using 2×6 ml of 2 M NaCl D-PBS. The fractions were then desalted, concentrated using a CentriPrep® centrifugal membrane (MWCO 3000) with D-PBS, and stored at −20° C.

To purify the conjugate, the 2M NaCl fraction was subjected to dialysis against D-PBS using MWCO 26,000 tubing for 12 hours at 4° C., then washed for 10 cycles using a CentriPrep® centrifugal membrane MWCO 30,000 with D-PBS at 12.0 rcf for 8 minutes/cycle. The collected conjugate was then used for ELISA, Western blot analyses and cell studies.

Figure 3C:
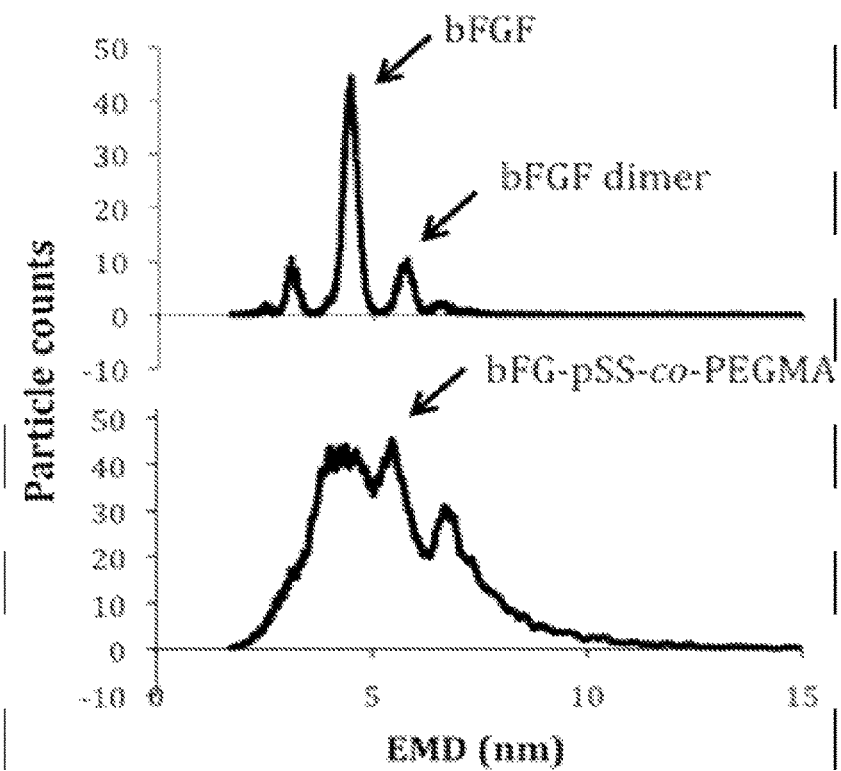

Analyses of the conjugates via matrix-assisted laser desorption/ionization (MALDI) and electrospray ionization mass spectrometry (ESI-MS) were unsuccessful due to difficulties in ionization of analytes and the sample heterogeneity. Therefore, electrospray ionization-gas-phase electrophoretic mobility molecular analysis (ESI-GEMMA) of the conjugate was employed. ESI-GEMMA is an ion mobility method that separates macromolecules based on their electrophoretic mobility in air that is directly related to their electrophoretic mobility diameters (EMD); we have shown previously that the technique can be applied to polymer conjugates. The ESI-GEMMA spectrum of bFGF (MW=16 kDa) showed a major peak at 4.45 nm corresponding to 16,116 Da (FIG. 3C, top). Utilizing the peaks for the bFGF-pSS-co-PEGMA and bFGF-pPEGMA (see FIG. 3C bottom, FIG. 8D) the molecular weights were 39 kDa and 30 kDa when assuming one polymer was attached to the protein (see Tao et al. for details of how the molecular weights were calculated). This agreed reasonably well with the theoretical MWs of 42 kDa and 39 kDa, respectively. The small discrepancy in the MWs was attributed to the inherent polydispersity of the conjugated polymers. The results were significantly different if instead the calculation assumed two polymers were attached to one protein (for example for bFGF-pSS-co-PEGMA the calculated MW of this conjugate was 41 kDa compared to the theoretical MW of 68 kDa). The results strongly support that one polymer was conjugated to bFGF for both conjugates.

Quantification Analysis of bFGF Conjugate Via ELISA.

The fractions collected from on-column conjugation were subjected to enzyme-linked immunosorbant assay (ELISA). The experiment was performed using the recommended protocol from the manufacture. In summary, a 96-well-plate was first coated with the capture antibody solution and incubated for 16 hours at 23° C. Then, the plate was blocked for 2 hours with 1% BSA. The bFGF standards (supplied with the ELISA kit) and samples in triplicate (multiple dilutions/samples sometimes were necessary to accurately detect the level of immunologically active protein) were allowed to incubate for 2 hours at 23° C. Subsequently, detection antibody-biotin conjugate solution was probed for 2 hours before streptavidin-HRP solution was added for 20 minutes. The colorimetric signals were developed by incubating the working plate with 1-Step™ Ultra TMB solution (Pierce Biotechnology, Rockford) for 6 minutes. The assay was stopped by addition of 50 µl of 1M $H_2SO_4$ solution per well. The absorbance signals were recorded at $\lambda=450$ nm, and the background at $\lambda=630$ nm was subtracted. The concentration of bFGF in each sample was determined via extrapolation from the linear standard curve consisting of 0, 12.5, 25, 50, 100, 200, 400, and 800 pg/ml bFGF.

Gel Electrophoresis.

The collected fractions from conjugation were subjected to SDS-PAGE analysis. Samples were assessed under non-reducing conditions using NuPAGE® 4-12% Bis-tris gel, and MES SDS running buffer from Invitrogen. The gel was run at 150V, 200 mA for 40 minutes. The gel was first fixed in fixing solution for 30 minutes before stained with iodine stain and silver stain subsequently.

Western blot analysis.

First, Samples were Assessed Via SDS-PAGE or Native PAGE. Then the gel was transferred to a nitrocellulose membrane (Whatman® Protran BA 95 Nitrocellulose) at 100V for 2 hours. The membrane was immediately blocked with 5% fat-free dry milk 1% BSA for 24 hours at 23° C. before incubation with rabbit anti-fibroblast growth factor basic antibody (1:20 dilution in blocking solution) at 4° C. for 16 hours. The membrane was washed by allowing shaking in Tris-buffer saline Tween-20 (TBST) solution for 3 cycles of 10 minutes each. Subsequently, the membrane was incubated with goat anti-rabbit IgG-HRP conjugate (1:1000 dilution in blocking solution) for 30 minutes at 23° C. After 3×10 minutes of washing in TBST, the membrane was developed for 5 minutes using SuperSignal® West Pico Chemiluminescent Substrate (Thermo Scientific, Waltham) and exposed for 5-15 minutes on a FluoroChem® FC2 system. See FIGS. 3B, 8B, and 8C for western blots). The Western blot analysis demonstrates that conjugates were made.

GEMMA Analysis.

Figure 8E:
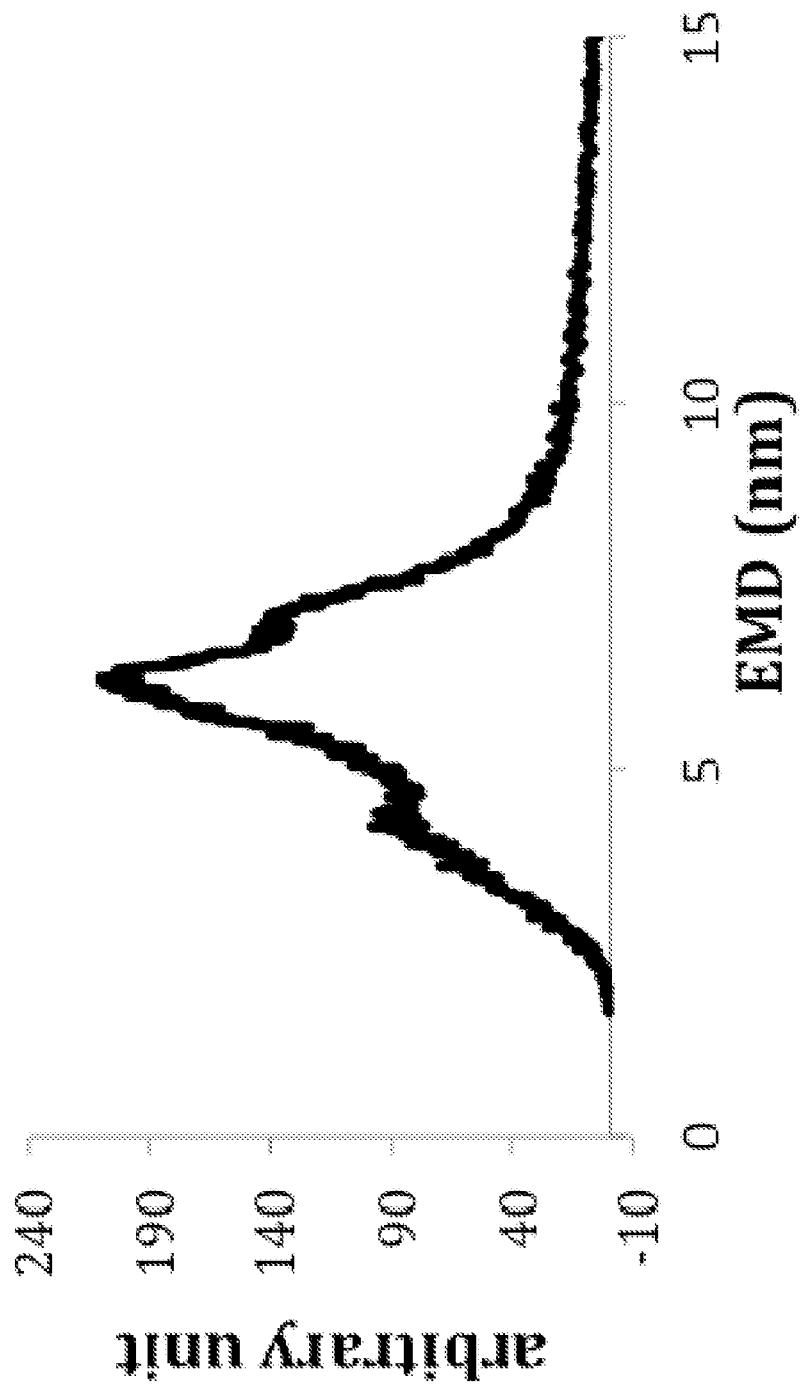
Figure 9:
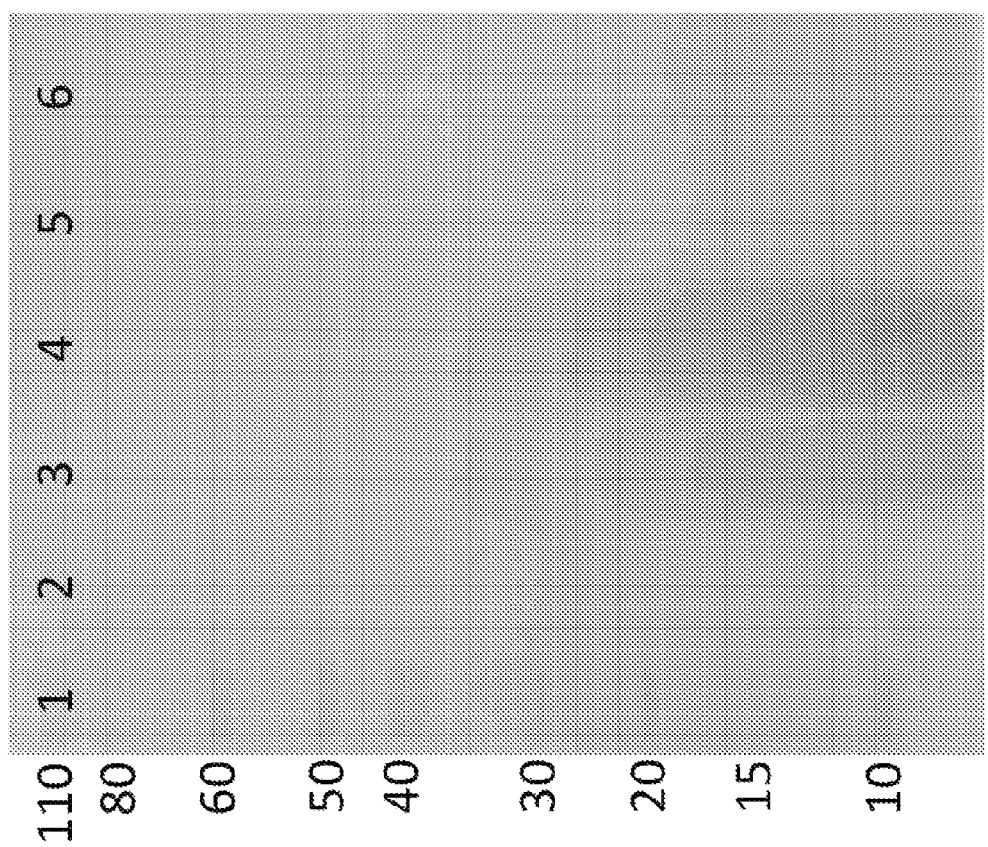
FIG. 9 depicts exemplary SDS-PAGE analysis of collected fractions from on-column conjugation of bFGF to PDS-pSS-co-PEGMA. The gel was stained with iodine stain. Lane 1: protein standards, lane 2: bFGF (not detected), lane 3: pSS-co-PEGMA, lane 4: 0M NaCl fraction, lane 5: 0.5M NaCl fraction, lane 6: 2M NaCl fraction.

Samples of proteins, polymers or conjugates were typically prepared in 20 mM ammonium acetate at the concentration range of 0.2 to 5 µg/ml. The samples were placed in the neutralizer chamber and the inlet flow rate was set to 100 nl/min. An average of 5 to 10 spectra per sample was obtained. The electrophoretic mobility diameter of the protein/conjugate was the centroid of the interested peak calculated by Peak Fit. Lysozyme was used as standard. GEMA results demonstrated that one polymer was attached to bFGF in each case (see FIGS. 3C, 8D, and 8E for GEMMA results).

Quantification Analysis of bFGF Conjugate Via Western Blot.

First, a solution of bFGF was quantified by ELISA. A set of 7-8 different concentrations of bFGF were prepared by serial dilutions. A known volume of each concentration or sample was allowed to incubate with Laemmli sample buffer+600 mM DTT on a dry bath at 85° C. for 3 minutes. Then, all samples were subjected to Western blot analysis as described above. ImageQuant™ program was used to measure the intensity signal from each lane. A standard curve consisting of 7 concentrations was generated with good linear correlation ($R^2=0.99032$). The concentration of a studied sample was extrapolated from the standard curve.

Quantification of Pyridyl Disulfide (PDS) End Group Retention.

To quantify the amount of PDS end group retention, PDS-pSS-co-PEGMA (1.43 mg, $2.74\times10^{-5}$ mmol) was dissolved in 1 ml of 0.1M phosphate buffer (PB) pH 8.0. The volume was split into two halves. In one vial, 4.2 µl of 100 µg/µl of DTT in 0.1M PB was added. The sample was diluted to 1 mL and allowed to incubate at 23° C. for 2 hours. In the second vial, the volume was brought to 1 ml with 0.1M PB (pH 8.0) without DTT to use as the control group. Absorbance of the by-product, pyridine-2-thione, at $\lambda=343$ nm ($\epsilon=8080$ $M^{-1}$ $cm^{-1}$ in water) was assessed via UV-vis spectrophotometry. Percentage of PDS end group retention was calculated using the formula % $PDS =$ $$\frac{[PDS]}{[PDS - pSS - co - PEGMA]} = \frac{Abs_{343}/\varepsilon}{[PDS - pSS - co - PEGMA]},$$

where $Abs_{343}$ was the difference in absorbance between the sample (with DTT) and the control (without DTT) at $\lambda=343$ nm. The experiment was repeated three times and the result was averaged. The molecular weight of the polymer reported by NMR was used to determine the polymer concentration.

Synthesis of 2-(pyridin-2-yldisulfanyl)ethyl 2-bromo-2-methylpropanoate 2-(Pyridin-2-yldisulfanyl)ethanol (698 mg, 3.73 mmol) was dissolved in 15 mL dichloromethane. Triethylamine (1.04 mL, 7.46 mmol) was added drop-wise. The solution was cooled to 0° C. in an ice-bath and 2-bromoisobutyryl-bromide (484 µL, 3.92 mmol) was added drop-wise. The mixture was stirred over 16 hours and allowed to come to room temperature gradually. The crude solution was washed twice with de-ionized water, once with sodium bicarbonate, once with brine, and once more with de-ionized water. The crude product was purified by silica column chromatography (1:1 hexane:ethyl acetate, $R_f=0.7$), and lyophilized to give a clear yellow oil (327 mg, 47% yield). δ $^1$H NMR (500 MHz, $CDCl_3$): 8.41-8.37 (1H, dq, J=4.55, 0.90 Hz, CHN), 7.66-7.62 (1H, dt, J=8.07, 0.94, CHCHCN), 7.60-7.55 (1H, td, J=7.68, 1.82, CHCHCN), 7.05-7.01 (1H, ddd, J=7.30, 4.83, 1.10 Hz, CHCHN), 4.38-0.32 (2H, t, J=6.45 Hz, $SSCH_2$), 3.06-2.99 (2H, t, J=6.45 Hz, $CH_2O$), 1.90-1.82 (6H, s, $CH_3CBr$). δ $^{13}$C NMR (500 MHz, $CDCl_3$): 171.15, 159.42, 149.48, 137.01, 120.80, 119.65, 63.38, 55.45, 36.87, 30.59. FT-IR ($cm^{-1}$): 3045, 2974, 2923, 1732, 1573, 1561, 1446, 1417, 1388, 1370, 1268, 1154, 1106, 1083, 1043, 1010, 985, 860, 835, 804, 758, 733, 716. MALDI-TOF MS (expected, observed) (Da): $[M_{H+}]=(335.97, 335.96)$, $[M_{Na+}]=(357.95, 357.97)$.

Electrospray Ionization-Gas-Phase Electrophoretic Mobility Molecular (ESI-GEMMA) Analysis.

Samples of proteins, polymers or conjugates were typically prepared in 5 or 20 mM ammonium acetate at a concentration range of 0.2 to 5.0 µg/ml. The ESI-GEMMA instrument (TSI Inc., Shoreview, Minn. USA) consists of an electrospray aerosol generator 3480 with a neutralizer chamber, a nano differential mobility analyzer (DMA) model 3085, and a condensation particle counter (CPC) type 3025A. The inlet flow rate and voltages were set to 70 nl/min, and 2-3 kV, respectively. The DMA sheath flow was set to 20 L/min, and the voltage was scanned from −10 to −10 000 V for 135 seconds to detect the electrophoretic mobility diameter (EMD) range of 2-56 nm. Particle counts per EMD were recorded by Aerosol Instrument Manager Software (TSI Inc.). An average of 5-10 spectra per sample was obtained. Curve smoothing was accomplished using the moving average over 7 points in Excel. The EMD of the protein/conjugate was found from the maximum of the peak of interest. Molecular weights were calculated using the formula MW=V*d*$N_a$, where d (in g/cm$^3$) is the effective density modeled to a sphere, $N_a$ is Avogadro's number, and V=(EMD)$^3$*π/6. Lysozyme was used as standard.

Figure 1F:
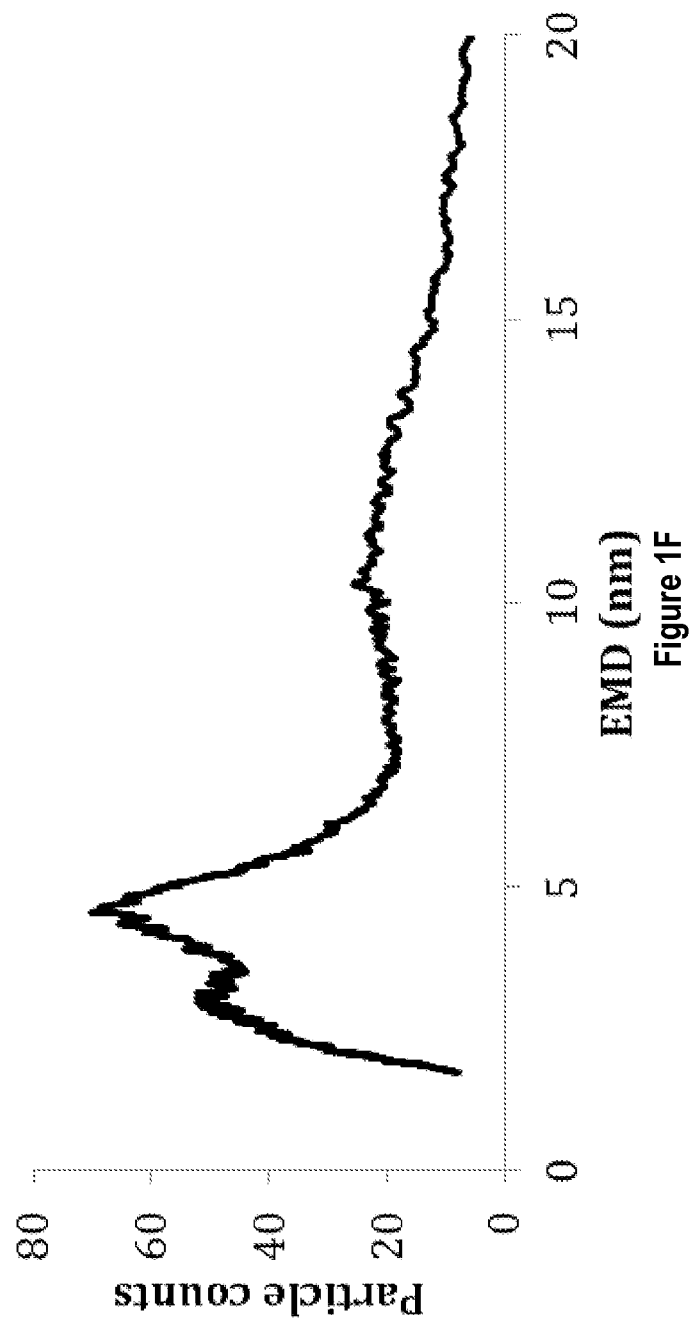
Figures 1G, 1H:
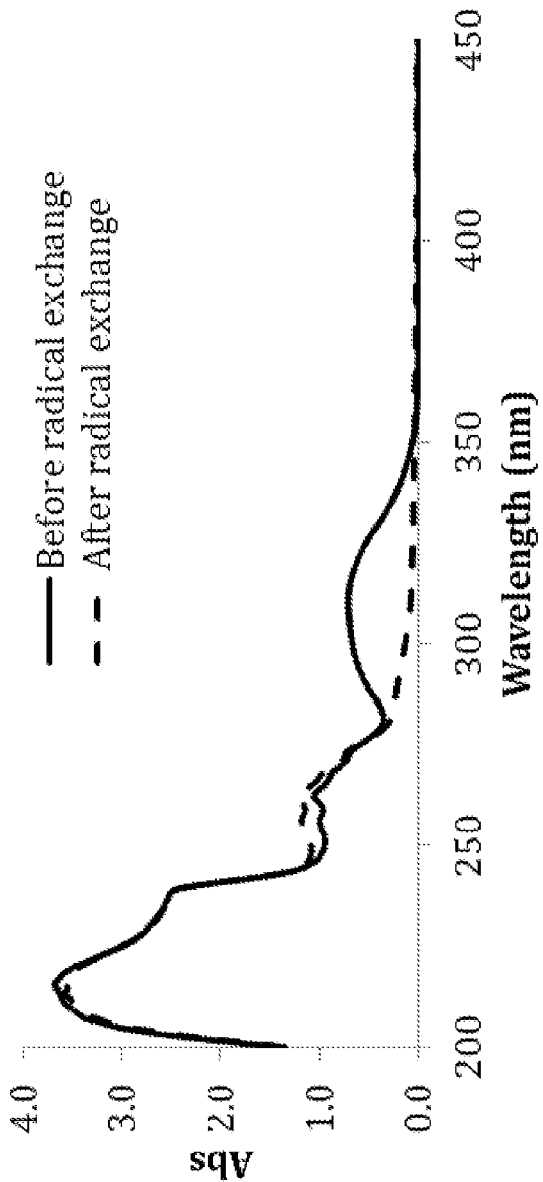
Figure 2E:
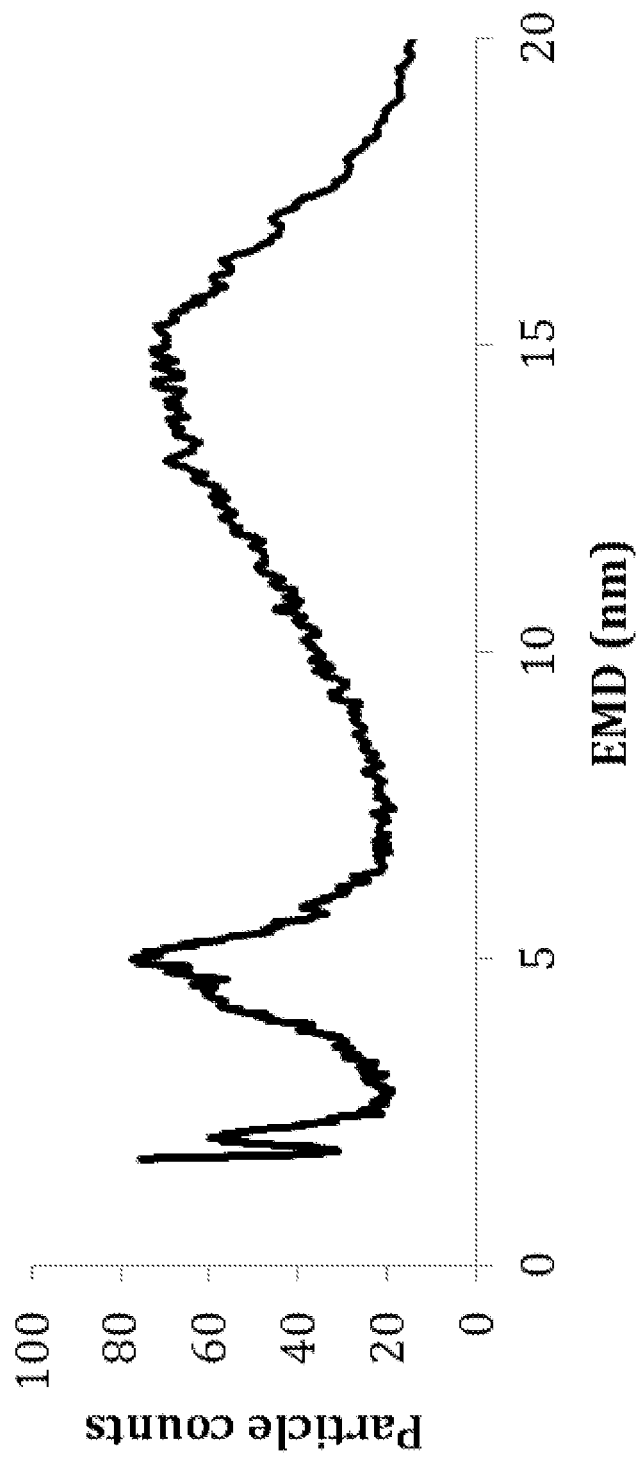

The ESI-GEMMA spectrum of bFGF (MW=16 kDa) showed a major peak at 4.45 nm corresponding to 16,116 Da when the average effective density for proteins (0.58 g/cm$^3$) was used in the calculation. (Kaddis et al., 2007) Effective densities of polymers and analytes in general vary depending on their composition and shape. (Kaddis et al., 2007; Saucy et al., 2004) They were determined experimentally for pSS-co-PEGMA and pPEGMA to be 0.90 g/cm$^3$ and 0.69 g/cm$^3$, respectively (see FIG. 1F and FIG. 2E). The effective densities of bFGF-pSS-co-PEGMA and bFGF-pPEGMA, assuming one protein linked to one polymer molecule, were 0.78 g/cm$^3$ and 0.64 g/cm$^3$, respectively. Employing these values, the experimental molecular weights of the bFGF-pSS-co-PEGMA and bFGF-pPEGMA conjugates were 39 kDa and 30 kDa.

Cell Culture.

Human Dermal Fibroblast (HDF) primary cells were purchased from PromoCell and cultured in PromoCell fibroblast growth medium containing 2% fetal calf serum, 1 ng/ml bFGF, 5 µg/ml insulin, supplemented with 100 µg/ml penicillin and 100 µg/ml streptomycin at 37° C., 5% CO$_2$. HDF cells were passaged every four days or after reaching 80% confluency. HDF cells were used up to passage 12 or 13. BaF3 cells were kindly provided by Dr. David Ornitz laboratory at University of Washing, St. Louis and cultured as recommended. Specifically, the cells were grown in RPMI1640 medium containing 10% newborn bovine calf serum, 2 mM L-glutamine, 0.5 ng/ml of recombinant mouse IL-3, 600 µg/ml of G418, 50 nM of 2-mercaptoethanol, supplemented with 100 u/ml penicillin and 100 µg/ml streptomycin at 37° C., 5% CO$_2$.

Cytotoxicity Study.

Figure 1A:
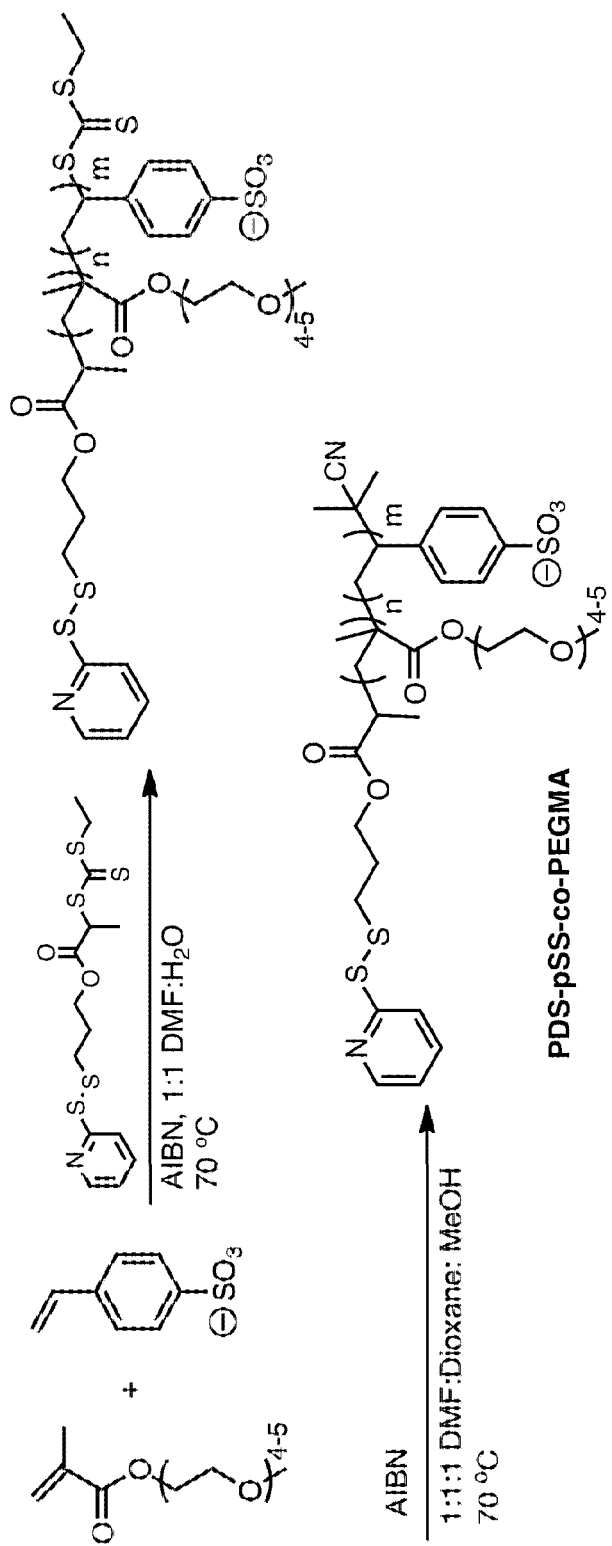
Figure 1B:
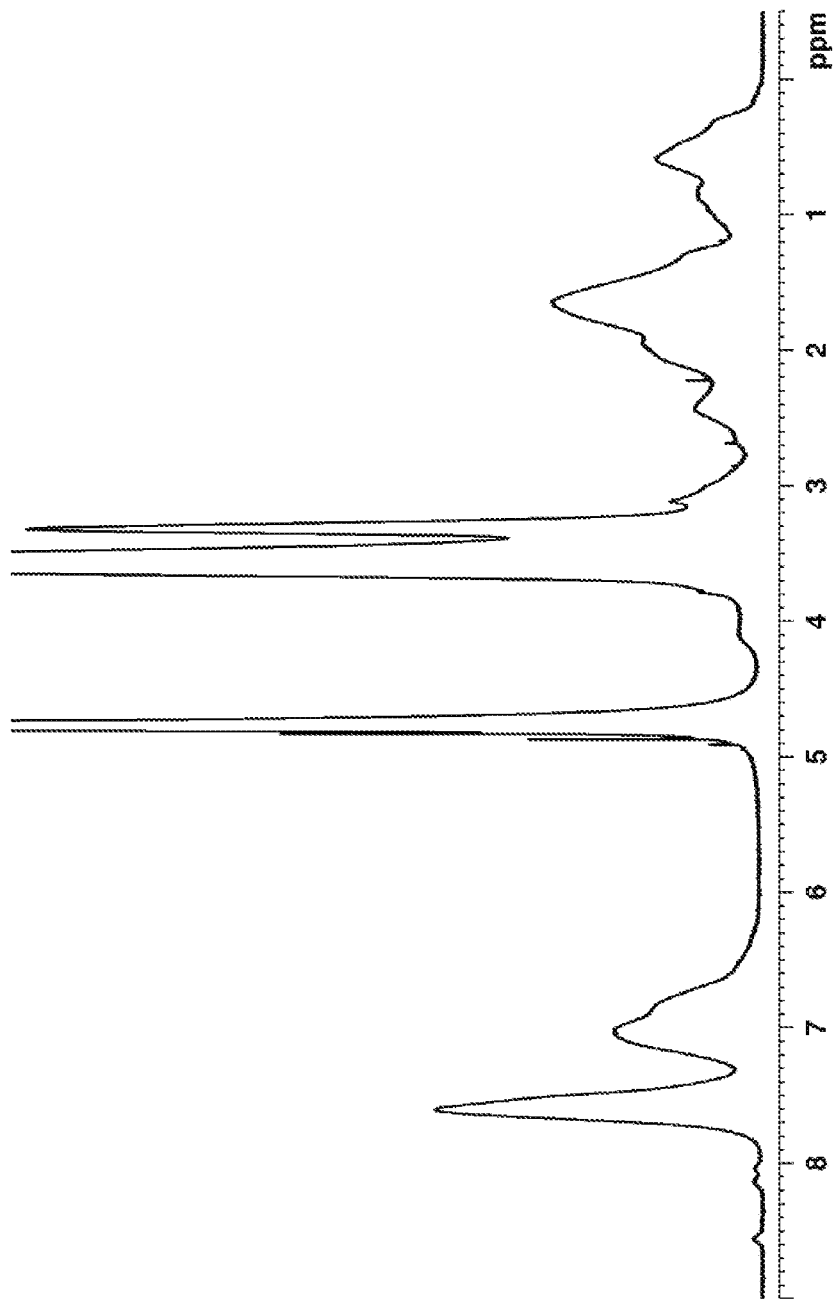
Figure 1C:
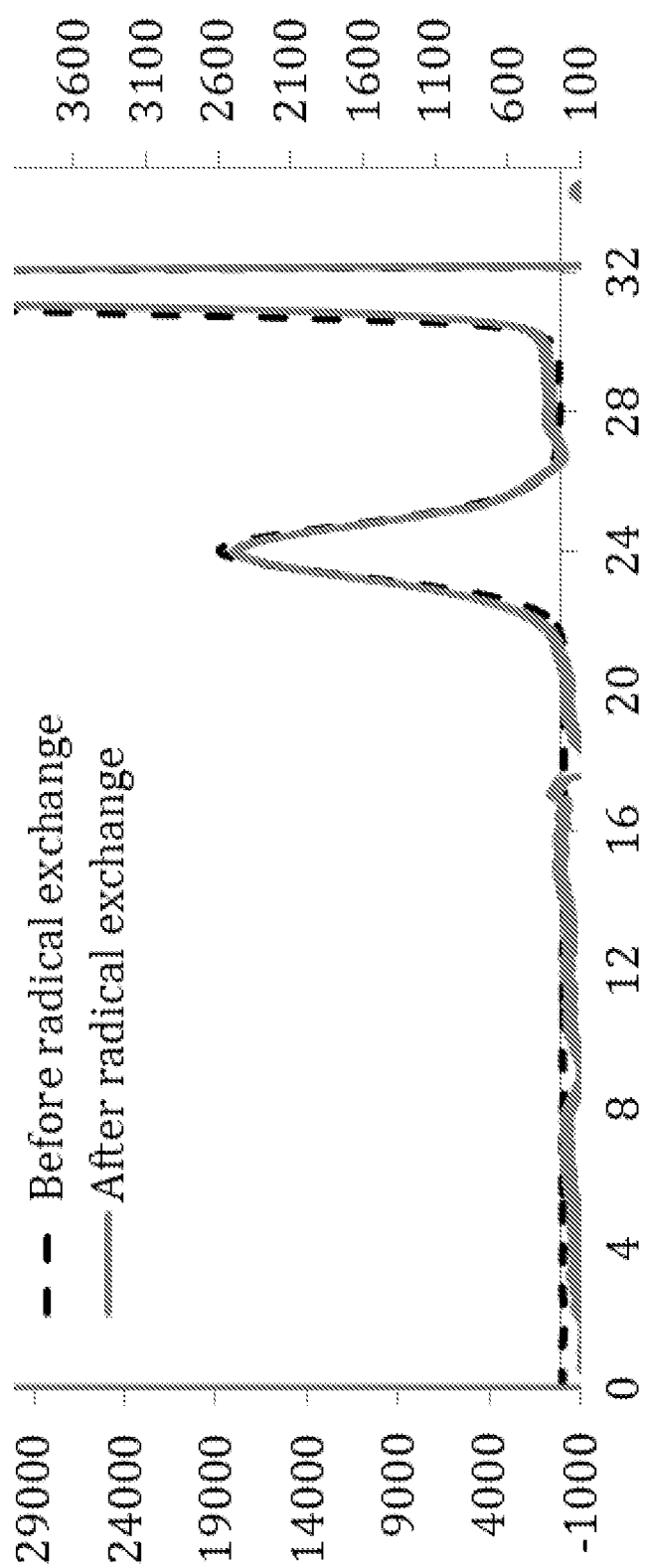
Figure 1D:
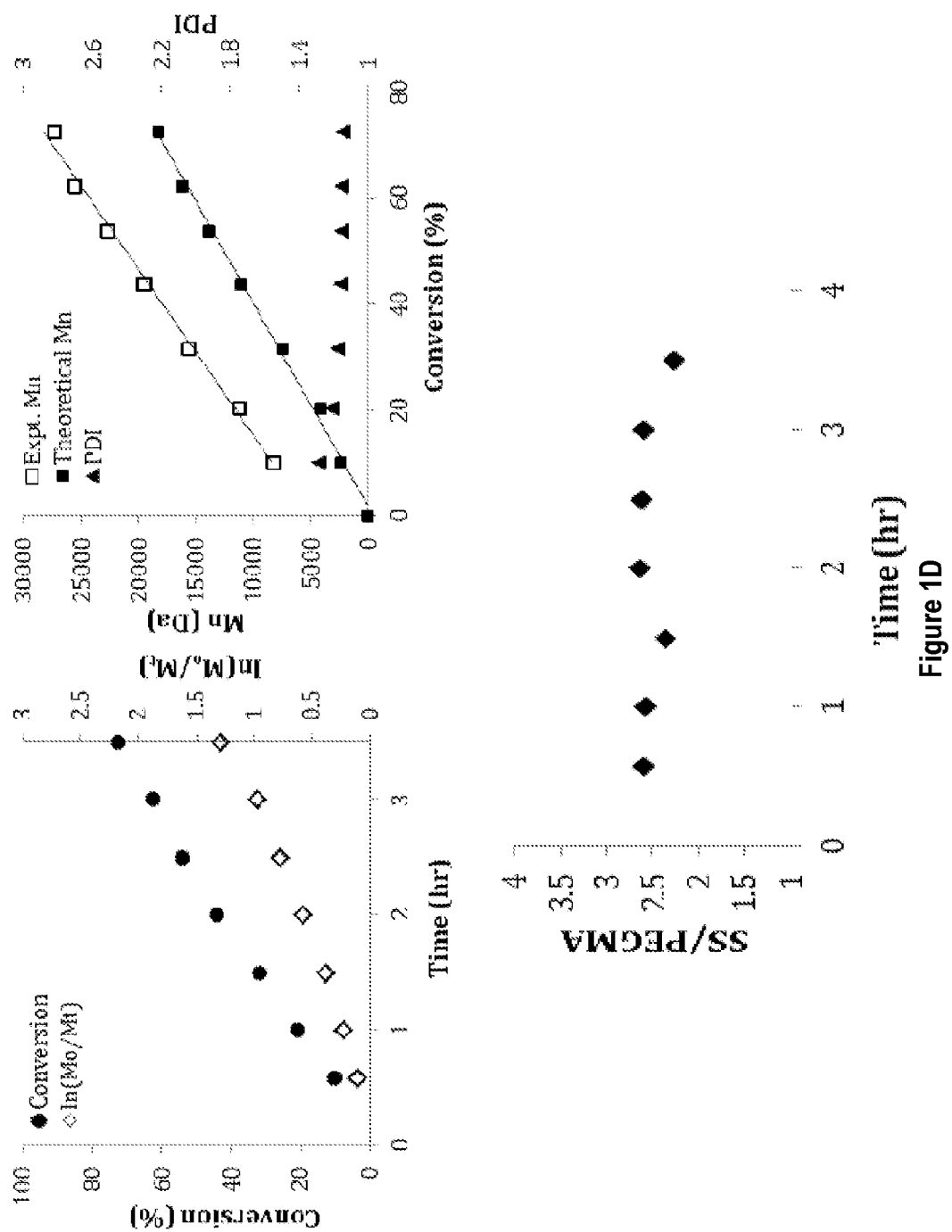

HDF cells were trypsinized and resuspended in fibroblast growth medium lacking bFGF. The cells were plated at a concentration of 5000 cells/well in a 48-well plate and allowed to adhere over 16 hours at 37° C., 5% CO$_2$. Then, the medium in the wells was replaced with 200 µl of the working medium containing various amount of polymer/heparin. After an incubation of 24 hours at 37° C., 5% CO$_2$, cell viability was assessed using LIVE/DEAD® viability/cytotoxicity assay. Briefly, the cells were washed twice with pre-warmed D-PBS, then incubated with 200 µl of 1 µM Calcein AM and 4 µM Ethidium homodimer-1 in D-PBS for 20 minutes at 37° C., 5% CO$_2$. The images of each well under a green channel and red channel were captured on an Axiovert 200 microscope equipped with an AxioCam MRm camera and FluoArc mercury lamp. The numbers of live and dead cells were counted manually using NIH Image J software, and percent live cells was calculated by dividing the number of live cells by the total number of live and dead cells. Each experimental group was done with four replicates, and the whole experiment was repeated four times, one of which was a blinded study. The results demonstrated that there was not change in viability of the copolymer up to 1 mg/mL concentration (see FIG. 5).

pSS-co-PEGMA was selected because it bound to bFGF in cell culture media, likely through interaction with the heparin-binding domain. bFGF has two free cysteines; thus, the polymer was prepared with a pyridyl disulfide (PDS) end group that reacts with thiols. Reversible addition-fragmentation chain transfer (RAFT) polymerization in the presence of 3-(pyridin-2-yldisulfanyl)propyl-2-(ethylthiocarbonothioylthio) propanoate as the chain transfer agent (CTA) produced the desired polymer (FIG. 1A).

Since the trithiocarbonate end group can exhibit cytotoxicity at high polymer concentrations, this group was removed by radical exchange with azobisisobutyronitrile (AIBN). The resulting copolymer PDS-pSS-co-PEGMA had a number average molecular weight (Ma) of 26.1 kDa by NMR and polydispersity index (PDI) of 1.16 (see FIG. 1). The analogous control polymer, PDS-pPEGMA, was prepared via atom transfer radical polymerization (ATRP) in the presence of an initiator 2-(pyridin-2-yldisulfanyl)ethyl 2-bromo-2-methylpropanoate, CuBr and 2,2'-bipyridine (FIG. 2A) and had an $M_n$ of 23.0 kDa by NMR and PDI of 1.13 (see FIG. 2).

Figure 5:
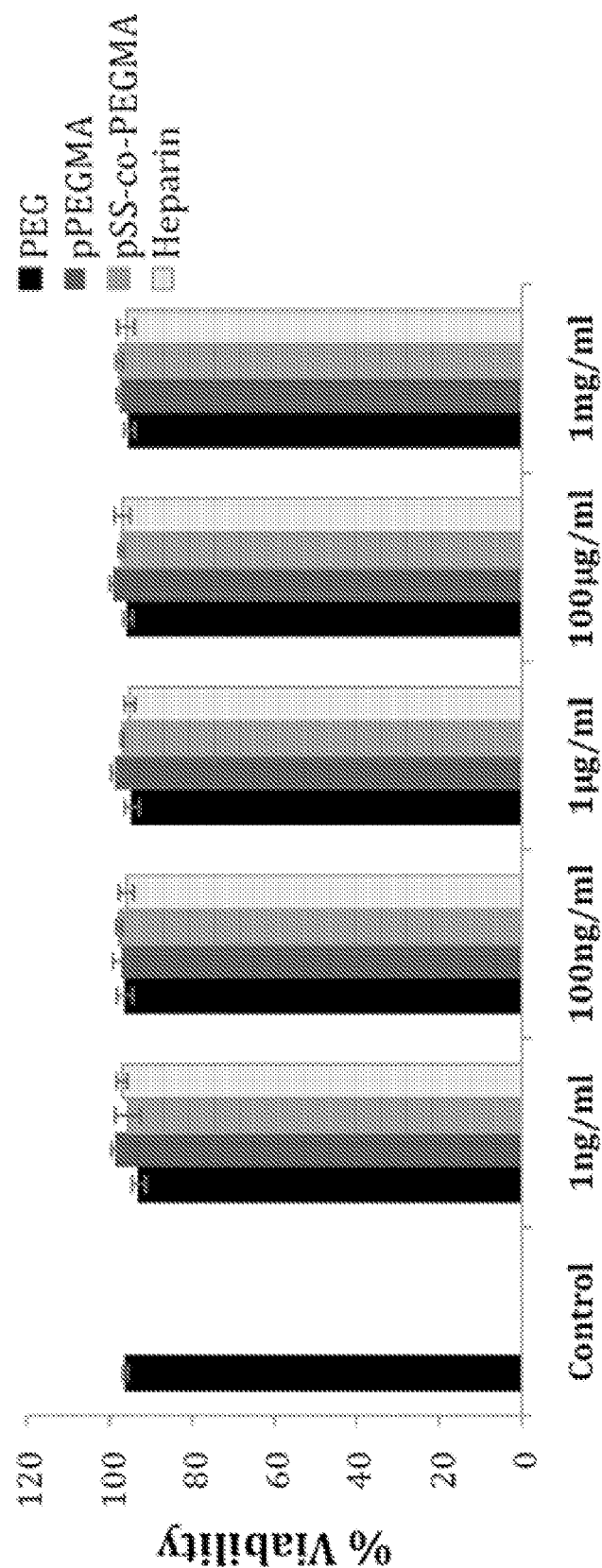
FIG. 5 depicts the exemplary results of a cytotoxicity study. 5,000 HDF cells/well was incubated with various concentrations of each polymer for 24 hours at 37° C., 5% CO$_2$. Then, each well was washed twice with D-PBS and subsequently incubated with 1 μM Calcein AM 4 μM Ethidium homodimer-1 in D-PBS for 20 minutes at 37° C., 5% CO$_2$. Percentage of live cells was calculated by dividing the number of live cells by the total number of live and dead cells. Each experimental group was done with four replicates, and the whole experiment was repeated four times, one of which was a blinded study. Error bars are SEMs. Copoly refers to the heparin mimicking polymer pSS-co-PEGMA. + refers to addition of polymer or heparin that is not covalently attached. bFGF-pPEGMA40K and bFGF-copoly are the control and heparin mimicking polymer conjugate, respectfully.

Next, the cytotoxicity of the pSS-co-PEGMA without the PDS end group was evaluated and compared to nontoxic PEG, control polymer pPEGMA and heparin. PEG 4-kDa was chosen as the control because it has a comparable number of repeating units to the pSS-co-PEGMA (DP=91 and 98, respectively). The cytotoxicity study was performed with normal human dermal fibroblast (HDF) cells. HDF cells play an important role in the wound healing process of skin, and the proliferation of these cells is largely stimulated by bFGF. HDFs were exposed to either pSS-co-PEGMA, pPEGMA, PEG, or heparin at increasing concentrations from 1 ng/ml to 1 mg/ml for 24 hours in the absence of bFGF before assessment with the LIVE/DEAD® cytotoxicity assay. The percent cell viability was the same in the presence of all of the polymers at all concentrations tested, and the same as no polymer added (FIG. 5). This demonstrated that the heparin mimicking polymer pSS-co-PEGMA is non-cytotoxic to HDF cells to at least 1 mg/ml.

Bioactivity Study.

HDF cells were trypsinized and resuspended in Ultra-CULTURE™ serum-free medium supplemented with 2 mM L-Glutamine and 100 u/ml penicillin and 100 µg/ml streptomycin. The cells were plated at a concentration of 2000 cells/well in a 96-well plate and allowed to adhere over 16 hours at 37° C., 5% CO$_2$. On the next day, fresh samples were prepared in the working medium to contain 1 ng/ml of bFGF/bFGF-pSS-co-PEGMA/bFGF-pPEGMA. The control experimental groups were prepared to contain 1 ng/ml of bFGF and either 1.5 ng/ml of heparin, 1 µg/ml of heparin, 1.5 ng/ml of pSS-co-PEGMA, or 1.5 ng/ml of pPEGMA. Then, the medium in the wells was replaced with 100 µl of each sample. After an incubation for 72 hours at 37° C., 5% CO$_2$, CellTiter-Blue® assay was carried out to evaluate cell proliferation. All experimental groups were normalized to the control group, which had only blank medium. Each group was done with six replicates, and the whole experiment was repeated four times, one of which was a blinded study.

Stability Study of bFGF and bFGF Conjugates Under Treatments.

To study the stability of bFGF and bFGF conjugates under various treatments (storage, acidic conditions, protease degradation, and heat), the protein and the conjugates were diluted in medium after these treatments and tested for their bioactivity in promoting HDF proliferation.

An amount of 15 µl of each experimental group was made up to contain 0.5 ng/µl of bGFG or either of the conjugates (e.g., bFGF-pSS-co-PEGMA and bFGF-pPEGMA). The control experimental groups were prepared to contain 0.5 ng/µl of bFGF and either 0.75 ng/µl of heparin, 5 µg/µl of heparin, 0.75 ng/µl of pSS-co-PEGMA, or 0.75 ng/µl of pPEGMA. The control blank group contained 15 µl of D-PBS. The 15 µl/experimental group was split into 4 vials of 3 μl/vial for four separate treatments. In one set of the 3 μl-vials, 27 μl of D-PBS was added to each vial and the samples were stored at 4° C. for 16 hours. In another set of 3 μl-vials, 27 μl of pH 4.7 PBS was added to each vial and the samples were stored at 4° C. for 16 hours. In the third set of 3 μl-vials, 27 μl of 0.1% Trypsin was added to each vial and the samples were stored at 4° C. for 16 hours. The fourth set of 3 μl-vials were stored at 4° C. for 16 hours before 27 μl of 1% TFA was added and treated for 2 hours at 4° C. The samples under no treatment and under heat treatment were prepared fresh in the same way towards the end of the 16 hour-treatment of other samples. The samples under heat treatment were placed in dry bath at 55° C. for 30 minutes. To stop all treatments, the samples were diluted to 1.5 ml of the UltraCULTURE™ serum-free medium to bring to final concentrations to 1 ng/ml of bFGF/bFGF-pSS-co-PEGMA/bFGF-pPEGMA, 1.5 ng/ml or 1 μg/ml of heparin, 1.5 ng/ml of pSS-co-PEGMA/pPEGMA. Then, the medium samples were used for cell proliferation assay as described above. After an incubation for 72 hours at 37° C., 5% $CO_2$, CellTiter-Blue® assay was carried out to evaluate cell proliferation. All experimental groups were normalized to the control group of that treatment group, which had only treated buffer in blank medium. Each group was done with six replicates, and the whole experiment was repeated four times, one of which was a blinded study. A two-way ANOVA and student's T-test were done for statistical analysis. The results demonstrated that the bFGF-heparin mimicking conjugate was stable to the treatment as was the positive control of incubation with 1 μg/mL of heparin. All other sets (heparin mimicking polymer not covalently attached, the PEGylated polymer control, and 1.5 ng/mL (equivalent to the concentration of the heparin mimicking polymer in the conjugate) of heparin) did not exhibit stability (see FIG. 4A).

Figure 4A:
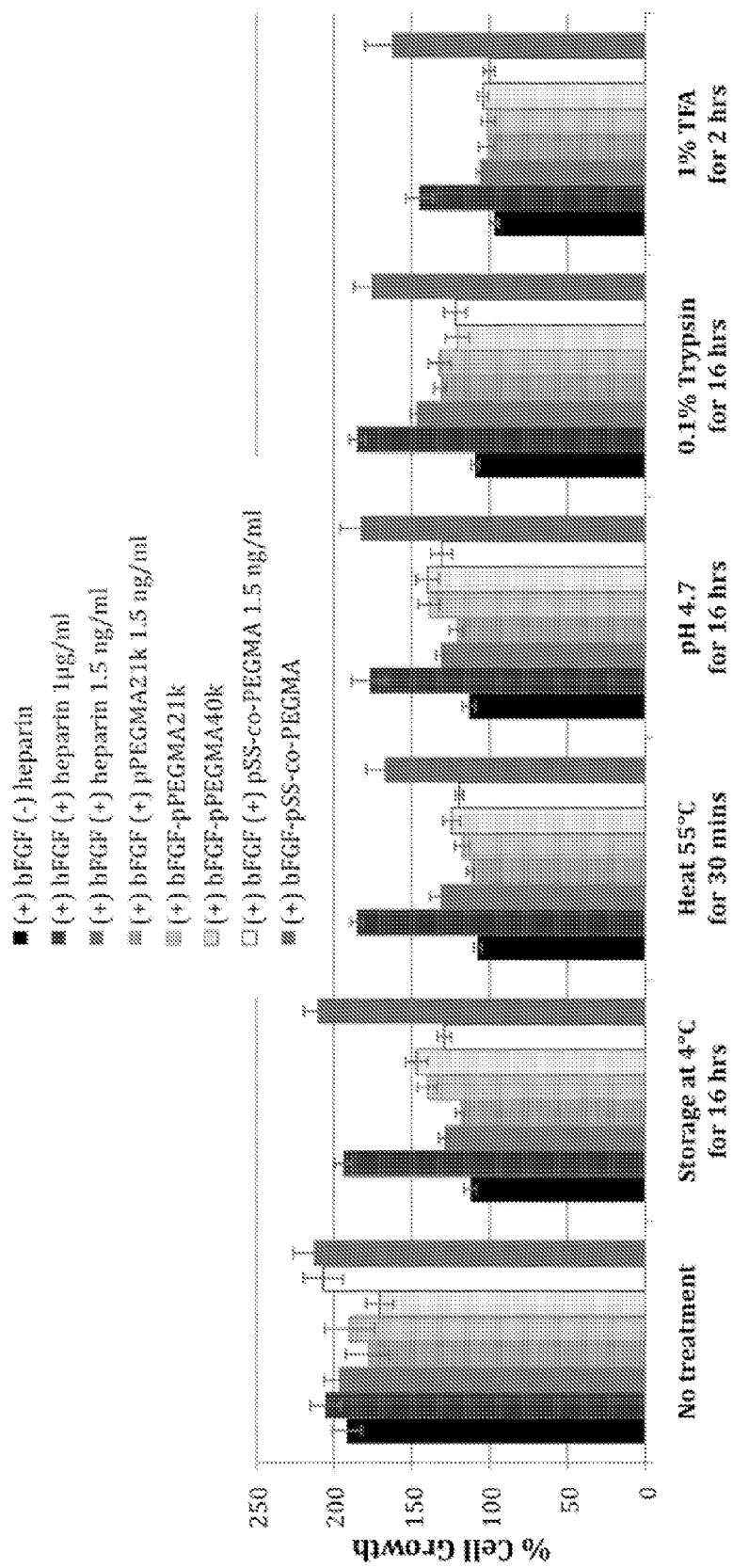
FIGS. 4A & 4B depict exemplary bioactivity study of bFGF-heparin mimicking (bFGF-pSS-co-PEGMA) conjugate in promoting HDF proliferation compared to other control groups before and after the treatments. Preparation of untreated and treated samples is detailed in the Methods section. The concentrations of bFGF and bFGF in the conjugates under treatment were 0.05 ng/μL. The concentration of heparin under treatment was 0.075 ng/μl or 0.05 μg/μl, while the concentrations of the unconjugated polymers were 0.075 ng/μl. The final concentrations of bFGF and bFGF conjugates in the medium were 1 ng/ml. In A), incubation of HDF with each of the samples was carried out for 72 hours. CellTiter® blue assay was performed to quantify percent cell growth. Data was normalized to the blank sample (no bFGF added) in that same treatment group. Each sample was done with six repeats, and the whole experiment was repeated eight times including one blinded study, except (+)bFGF(+)1.5 ng/ml pPEGMA and (+)bFGF-pPEGMA were repeated four times. Error bars are SEM. Statistical analysis was done using two-way ANOVA and Student's T-test. * denotes p<0.05,  denotes p<0.01 and * denotes p<0.001 between the sample indicated and the (+) bFGF (−) heparin within that same stress set. B) Bioactivity study of bFGF-heparin mimicking polymer, bFGF-pSS-co-PEGMA conjugate, after 4-week storage at 4° C. Data was normalized to the blank sample (contained medium only). Each group was done with six replicates.

HDFs were used as the in vitro model to evaluate the bioactivity of the bFGF-heparin mimicking polymer conjugate before and after exposure to various stresses. With careful storage at −80° C. before use for all samples, an addition of 1 ng/ml of bFGF-pSS-co-PEGMA conjugate stimulated cell growth to 213±13%, which was not statistically different than when 1 ng/ml of bFGF (192±9%), bFGF (+) 1 μg/ml of heparin (205±10%), bFGF (+) 1.5 ng/ml of heparin (197±4%), bFGF (+) 1.5 ng/ml of pPEGMA (179±14%), 1 ng/ml of bFGF-pPEGMA (190±6%), or bFGF (+) 1.5 ng/ml of pSS-co-PEGMA (207±5%) were applied (FIG. 4A). Thus, all the samples all had similar activity prior to application of stress.

Stressors were chosen to investigate the stability of the bFGF-pSS-co-PEGMA conjugate in comparison to other groups. The chosen treatments represent environmental stresses that the growth factor (or any heparin-binding protein) could be exposed to. For example, storage in the unfrozen form and exposure to heat during delivery, transport, or use were represented by the "Storage at 4° C. for 16 hours" treatment and "Heat at 55° C. for 30 minutes" treatment, respectively. Incubation at "pH 4.7 for 16 hours" is relevant because mildly acidic conditions are necessary to inhibit bacterial growth during wound treatment.

Furthermore, the stability of the bFGF-heparin mimicking conjugate was challenged against proteolytic degradation and extreme acidic conditions by incubating with 0.1% w/v trypsin for 16 hours and 1% trifluoroacetic acid (TFA) for 2 hours, respectively. The starting concentrations of bFGF and bFGF in the conjugates were equivalent and the concentrations of the unconjugated polymers and heparin were the same at approximately stoichiometric ratios to bFGF. The positive control group contained a large excess (700 molar) of heparin to bFGF. The negative control was native bFGF alone.

In all cases, the bioactivity of bFGF-pSS-co-PEGMA was significantly better than all the other sets including bFGF-PEGMA, and the same as the positive control (FIG. 4A). Upon exposure to storage and mildly acidic conditions, the bioactivity of bFGF-pSS-co-PEGMA was statistically the same as before treatment (213±13%). After storage at 4° C. for 16 hours, the bioactivity was completely retained (210±10%). The percent cell growths of bFGF-pSS-co-PEGMA under heat, trypsin and 1% TFA treatments were 167±12%, 176±11%, and 162±17% respectively. The heparin mimicking conjugate was statistically the same as the positive control, bFGF with 700 molar excess of heparin, in each case. The bFGF-pPEGMA conjugate did exhibit some stability under storage, mildly acidic and trypsin treatments (p<0.01). However, the bFGF-pSS-co-PEGMA conjugate had a significantly better stability profile than the bFGF-pPEGMA conjugate for all treatments (p<0.001 for Storage treatment, p<0.05 for other treatments). This result demonstrates the importance of a heparin-mimicking polymer for the observed protective effect.

Figure 4B:
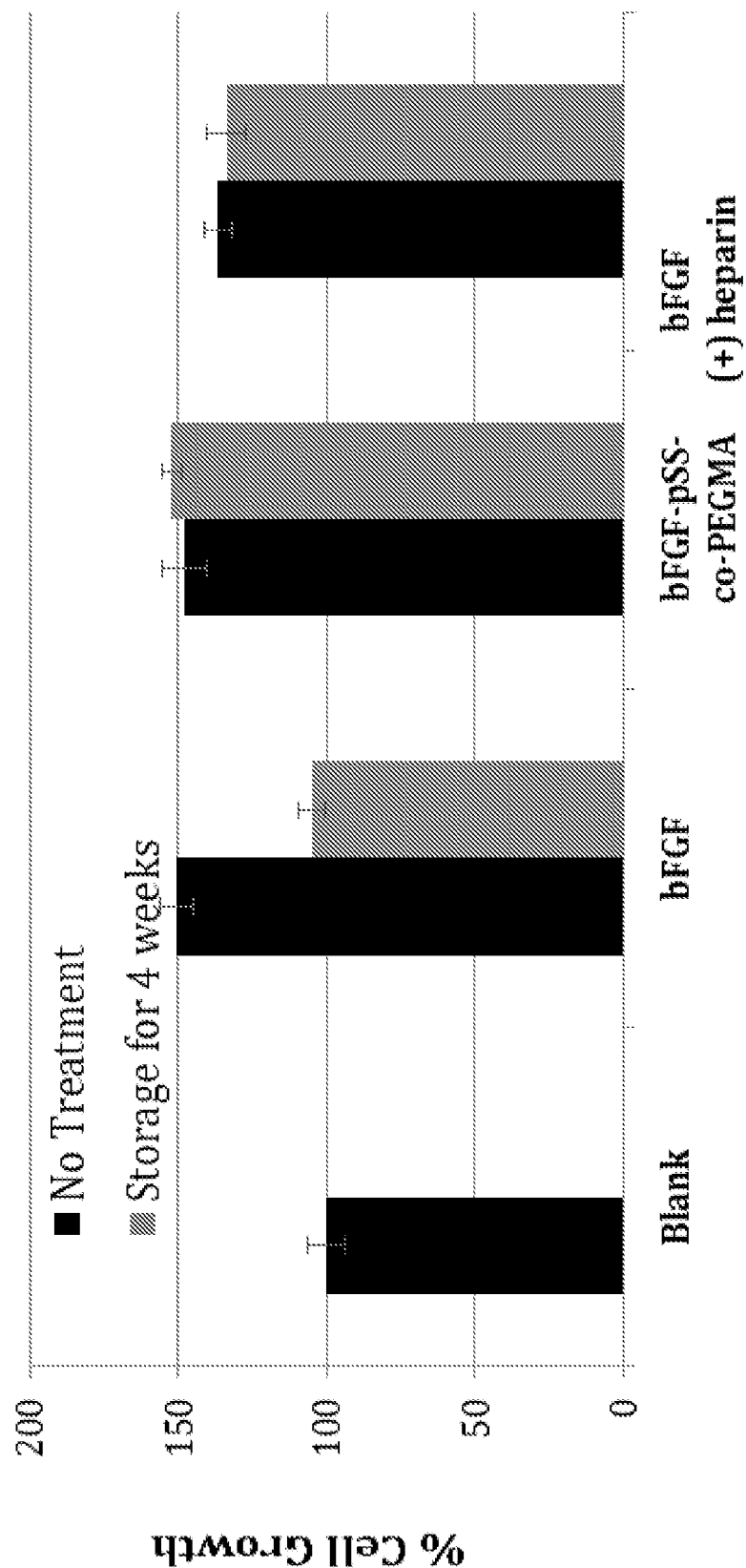

Bioactivity study of bFGF-pSS-co-PEGMA conjugate after long-time storage was also tested. After 4 weeks of storage 4° C. (longest period tested), the activity of the bFGF-pSS-co-PEGMA conjugate was completely retained, demonstrating the long-term storage capacity of the heparin mimicking copolymer conjugate (FIG. 4B).

In these experiments, an amount of 30 μl of each experimental group in D-PBS was made up to contain 0.05 ng/μl of bFGF or bFGF-pSS-co-PEGMA conjugate. The positive control group was prepared to contain 0.05 ng/μl of bFGF and 0.05 μg/μl of heparin. The samples were then stored at 4° C. for 4 weeks. At the end of the treatment time, the samples were diluted to 1.5 ml of the UltraCULTURE™ serum-free medium to bring final concentrations to 1 ng/ml of bFGF/bFGF-pSS-co-PEGMA, and 1 μg/ml of heparin. The samples under no treatment were prepared to the indicated final concentrations in the working medium without serial dilutions. Then, the medium samples were used for cell proliferation assay of Human Dermal Fibroblast (HDF) cells. Sixteen hours prior to the assay, the cells were plated at a concentration of 4,000 cells/well in a 96-well plate and allowed to adhere for 16 hours at 37° C., 5% $CO_2$. Then, a 100 μL of each prepared sample was replaced in each well. After an incubation for 72 hours at 37° C., 5% $CO_2$, CellTiter-Blue® assay was carried out to evaluate cell proliferation. All experimental groups were normalized to the control group, which received only blank medium. Each group was done with six replicates.

Inhibition Assay.

To confirm that the bFGF-heparin mimicking conjugate promoted cell growth by the same transduction pathway as by native bFGF, a potent inhibitor for FGF receptor 1 (FGFR1) was included in the media. PD173074 (N-[2-[[4-(diethylamino)butyl]amino]-6-(3,5-dimethoxyphenyl)pyrido[2,3-d]pyrimidin-7-yl]-N'-(1,1-dimethylethyl)-urea) competes with adenosine-5'-triphosphate (ATP) for binding to the receptors, a key step for FGFR phosphorylation, and shuts down the signal transduction pathways associated with cell proliferation. HDF cells express primarily FGFR1, and PD173074 has been well demonstrated to deactivate FGFR1 phosphorylation at low concentration.

HDF cells were trypsinized and resuspended in UltraCULTURE™ serum-free medium supplemented with 2 mM L-Glutamine and 100 u/ml penicillin and 100 μg/ml streptomycin. The cells were plated at a concentration of 2000 cells/well in a 96-well plate and allowed to adhere over 16 hours at 37° C., 5% $CO_2$. On the next day, the experimental groups were prepared to contain 1 ng/ml of bFGF, or 1 ng/ml of bFGF with 1 µg/ml of heparin, or 1 ng/ml of bFGF-pSS-co-PEGMA; all with an addition of 125 nM of the inhibitor PD173074. The control groups were the replicates but without the addition of the inhibitor. Then, the medium in the wells was replaced with 100 µl of each sample. After an incubation for 72 hours at 37° C., 5% $CO_2$, CellTiter-Blue® assay was carried out to evaluate cell proliferation. All the groups were normalized to the control group, which had only blank medium without the inhibitor. Each group was done with six replicates, and the whole experiment was repeated three times. PD173074 is a specific inhibitor of the bFGF receptor. The results demonstrate that the conjugate binds to this receptor as does bFGF (see FIG. 6).

Figure 6:
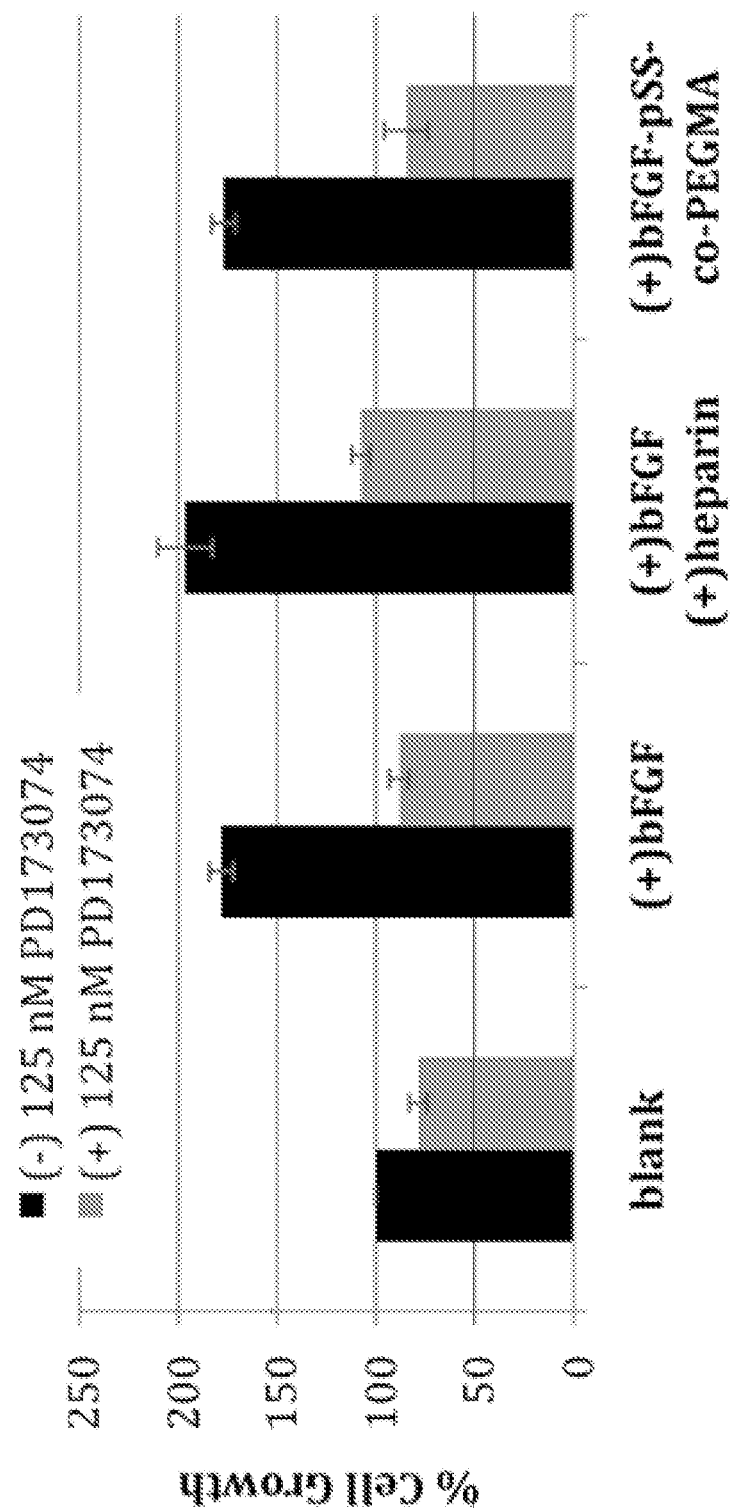
FIG. 6 depicts the exemplary results of an inhibition assay. The medium samples were prepared with and without 125 nM of PD173074. 2,000HDF cells/well was incubated with each of the sample for 72 hours at 37° C., 5% CO$_2$. Each sample group was done with six replicates, and the whole experiment was repeated three times. Error bars are SEMs. + refers to addition of polymer or heparin that is not covalently attached. bFGF-pPEGMA40K and bFGF-copoly are the control and heparin mimicking polymer conjugate, respectfully.
Figure 7A:
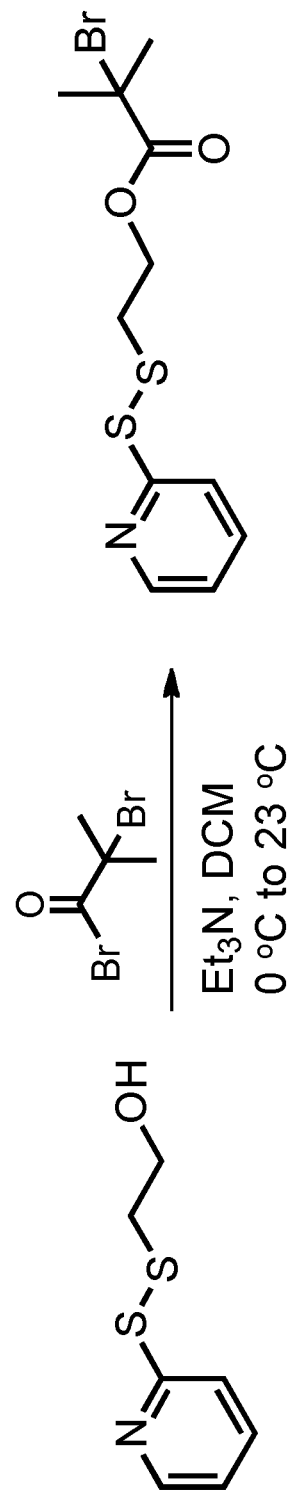
FIGS. 7A-7D depict exemplary synthesis and characterization of 2-(pyridin-2-yldisulfanyl)ethyl 2-bromo-2-methylpropanoate. (A) Synthesis scheme; (B) $^1$H NMR spectrum in CDCl$_3$; (C) $^{13}$C NMR spectrum in CDCl$_3$; and (D) FT-IR spectrum of the compound.
Figure 7B:
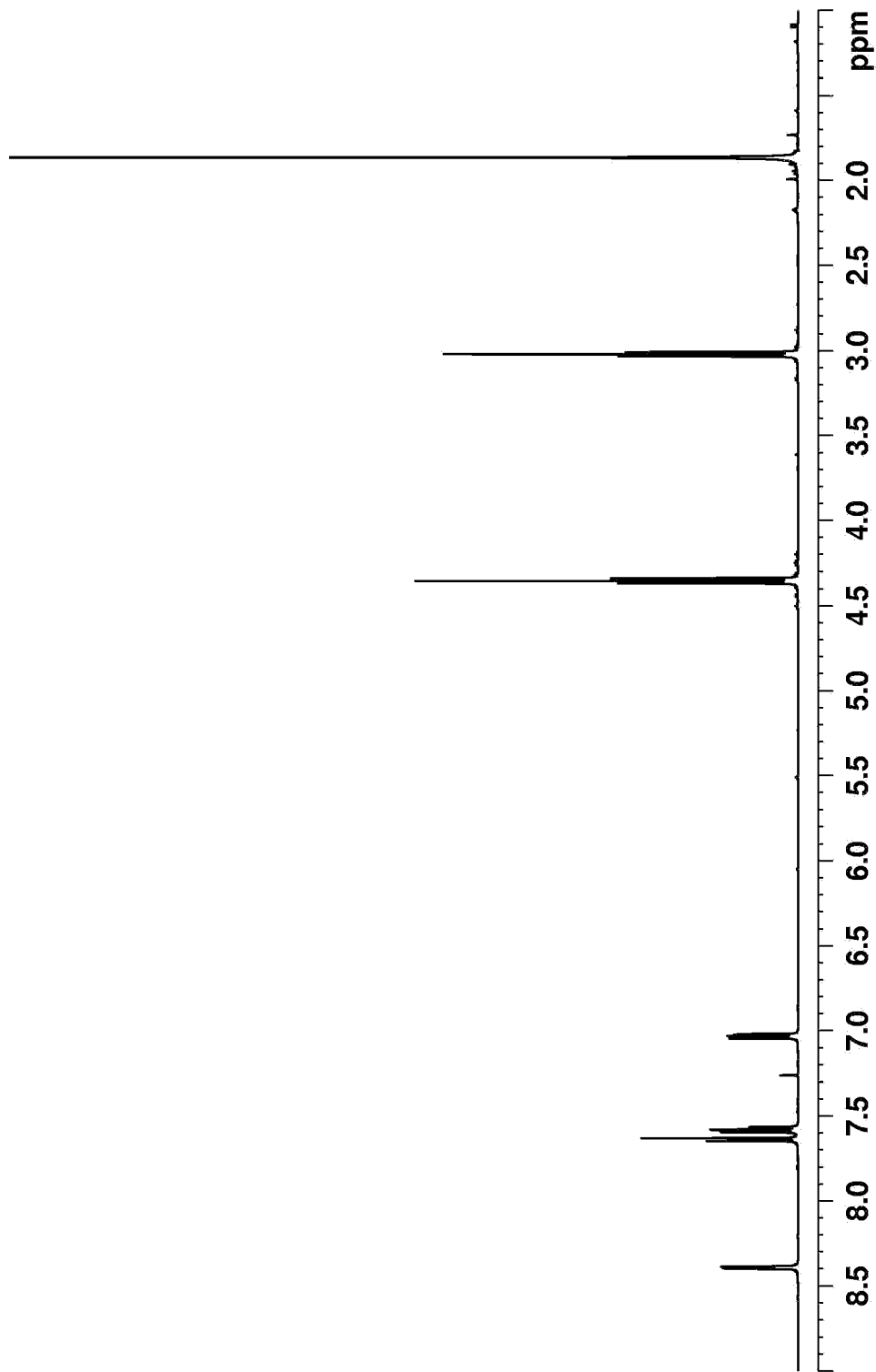
Figure 7C:
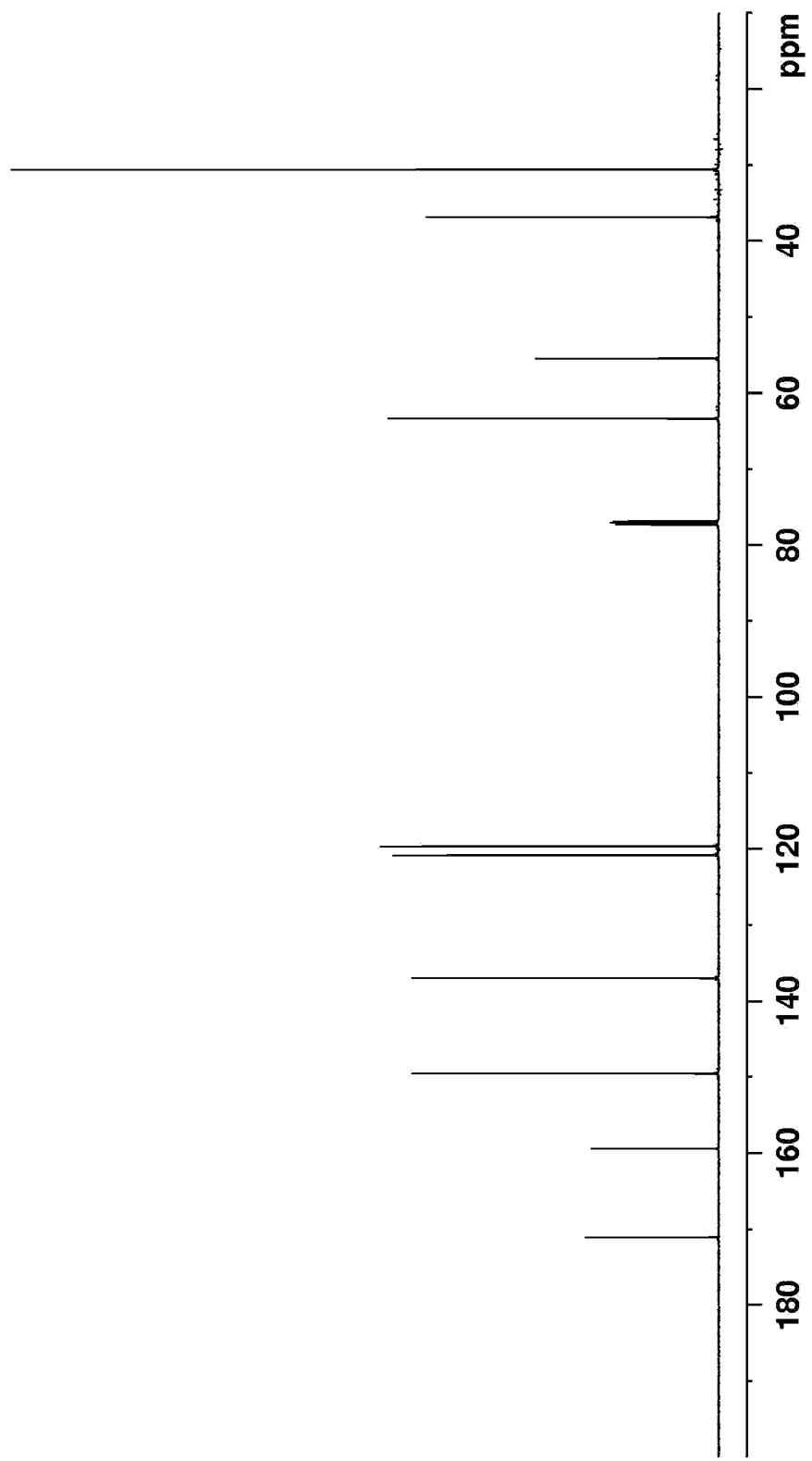
Figure 7D:
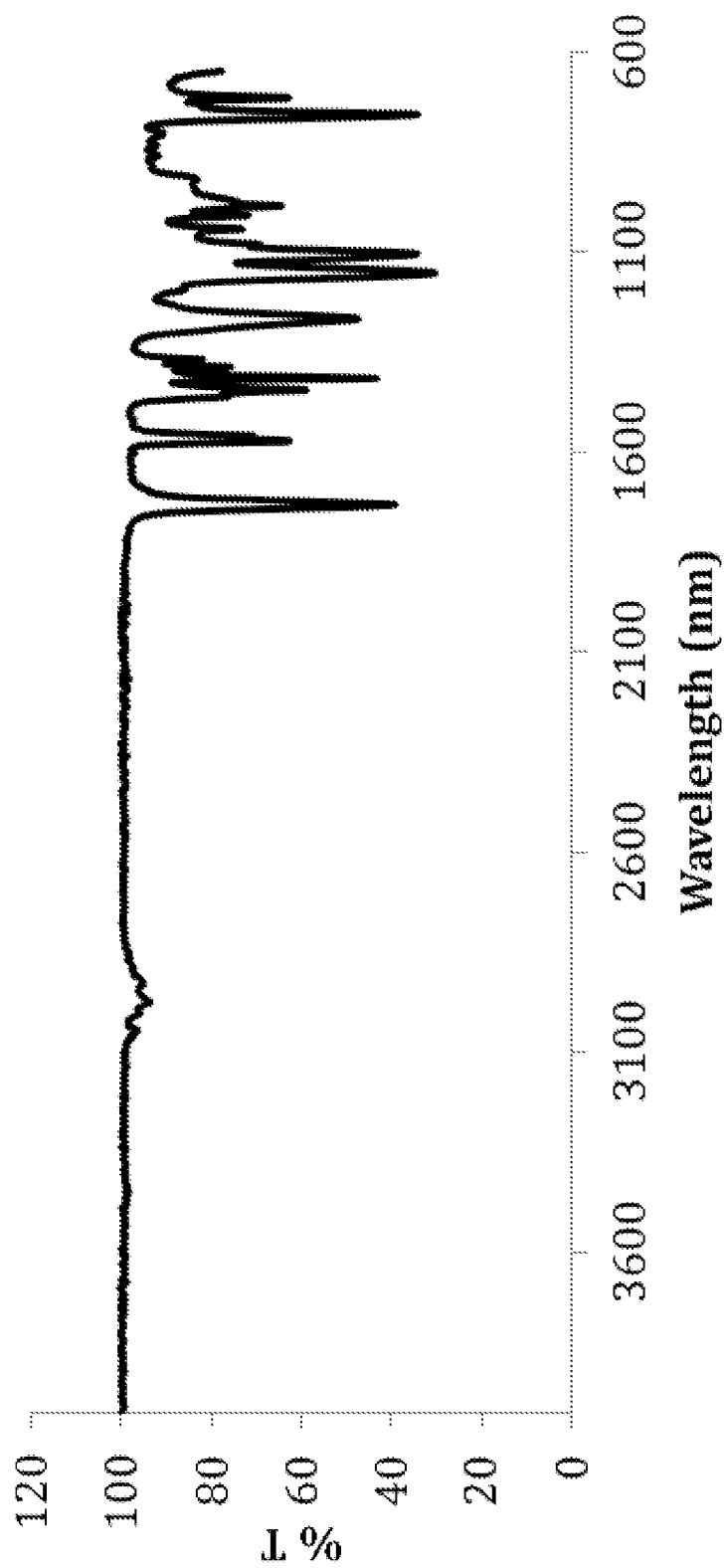

The following groups were tested: 1 ng/ml of bFGF, 1 ng/ml of bFGF with 1 µg/ml of heparin, and 1 ng/ml bFGF-pSS-co-PEGMA. The data was normalized to the blank group containing no PD173074. FIG. 6 shows that for 1 ng/ml of bFGF with no inhibitor present, the percent cell growth was 178±6%, while in the presence of 125 nM PD173074, the percent cell growth was decreased to 88±5%. Similarly for bFGF-pSS-co-PEGMA, the percent cell growths without and with the addition of PD173074 were 177±6% and 85±11%, respectively. In the presence of 1 µg/ml of heparin, cell proliferation at 197±14% was also reduced to 108±5% when 125 nM of PD173074 was added. This data indicates that the bFGF-heparin mimicking polymer conjugate triggers HDF proliferation through transmembrane tyrosine kinase receptor (FGFR) activation similar to the native bFGF, since activity was abrogated by an inhibitor for this receptor.

Proliferation Study of BaF3 Cells

While bFGF interacts directly with cells by binding to FGFRs, signal transduction cannot occur without the simultaneous interaction with heparan sulfate proteoglycan (HS) cell surface receptors. To investigate whether the heparin mimicking polymer pSS-co-PEGMA participated in the binding site, BaF3 cells (FR1C-11) were used. BaF3 cells are engineered to express FGFR1 and lack cell-surface HS; addition of soluble heparin is required to activate the cells with bFGF. A high concentration of heparin (1 µg/ml) effectively stimulated cell proliferation as expected. Percent cell growth was almost four times the blank control (384±35%) (FIG. 12). An addition of 1 µg/ml of the pSS-co-PEGMA did not show increase in proliferation; the percent cell growth (128±13%) was similar to the sample group where bFGF was added without heparin (127±12%). Likewise, 1 ng/ml of the bFGF-pSS-co-pPEGMA conjugate did not stimulate cell growth (147±14%), suggesting that the heparin-mimicking polymer did not participate in the receptor binding of the protein to FGFRs. Thus the role of the polymer was to stabilize the growth factor, not to also activate the receptor.

Screening for New Heparin-Mimicking Polymers with Biological Activity of the Growth Factor Various sulfonated polymers were either purchased (poly (sodium 4-styrenesulfonate) (pSS) polymers) or synthesized via radical polymerization. Poly(potassium 3-sulfopropyl methacrylate) (pSPM), Poly(potassium 3-sulfopropyl methacrylate-co-hydroxyethylmethacrylate) (pSPM-co-HEMA) (3:1 SPM:HEMA), poly(sodium vinyl sulfonic acid) (pVS) and poly(sodium 1-allyloxy-2 hydroxypropyl sulfonate) (pAHPS) were synthesized via free radical polymerization using 4,4'-azobis(4-cyanovaleric acid) (V501) as the initiator. The different sizes were obtained by varying the ratio of monomer:initiator. Poly(2-acrylamido-2-methylpropane sulfonic acid-co-hydroxyethylmethacrylate) (pAMPS-co-HEMA) were prepared via reversible addition-fragmentation chain transfer (RAFT) polymerization using ethyl (1-oxo-1-((2-(pyridin-2-yldisulfanyl)ethyl)amino)propan-2-yl) carbonotrithioate and azobisisobutyronitrile (AIBN) as chain transfer agent (CTA) and initiator, respectively. However, any polymerization method may be utilized to make these polymers.

To study for the capacity of the polymers to replace the biological role of heparin/heparin sulfate, various concentrations of each polymer were incubated with BaF3 cells in the presence of bFGF. The extent of induced proliferation was compared to the positive controls that contained equivalent concentrations of heparin. FIG. 13 summarizes the results obtained for select polymers (structures shown on right of each bar graph). A 100% cell growth indicated no proliferation induction; less than 100% means inhibition in proliferation; and over 100% means proliferation activation.

Statistical Analysis.

The data was presented as the average and the standard deviation or standard error of the mean (SEM) where $SEM = STDEV/(n^{1/2})$ were n=the number of repeats. A two-way ANOVA was performed with sample groups and treatments as the two factors and found that the p values were $1 \times 10^{-46}$ and $4 \times 10^{-47}$. Individual comparisons were made with Student's t-test. Statistical analysis was made with Student's t-test. All tests were two-tailed, unpaired and p<0.05 was considered significant.

REFERENCES (1) Nimni, M. E. Biomaterials 1997, 18, 1201-1225.
(2) Richard, J. L. et al. Effect of topical basic fibroblast growth-factor on the healing of chronic diabetic neuropathic ulcer of the foot—A pilot, randomized, double-blind, placebo-controlled study. *Diabetes Care* 18, 64-69 (1995).
(3) Gospodarowicz, D. & Cheng, J. Heparin protects basic and acidic FGF from inactivation. *J. Cell Physiol.*, 475-484 (1986).
(4) Folkman, J.; Klagsbrun, M.; Sasse, J.; Wadzinski, M.; Ingber, D.; Vlodaysky, I. American Journal of Pathology 1988, 130, 393-400.
(5) Capila, I.; Linhardt, R. J. Angewandte Chemie-International Edition 2002, 41, 391-412.
(6) Edelman, E. R., Mathiowitz, E., Langer, R., Klagsbrun, M. Biomaterials 1991, 18.
(7) Sakiyama-Elber, S. E. 4.420—Drug Delivery via Heparin Conjugates. *Comprehensive Biomaterials* 4, 6 (2011).
(8) Folkman, J.; Weisz, P.; Joullie, M.; Li, W.; Ewing, W. Science 1989, 243, 1490-1493.
(9) Danesi, R.; Delbianchi, S.; Soldani, P.; Campagni, A.; Larocca, R. V.; Myers, C. E.; Paparelli, A.; Deltacca, M. British Journal of Cancer 1993, 68, 932-938.
(10) Waltenberger, J.; Mayr, U.; Frank, H.; Hombach, V. Journal of Molecular and Cellular Cardiology 1996, 28, 1523-1529.
(11) Manetti, F.; Cappello, V.; Botta, M.; Corelli, F.; Mongelli, N.; Biasoli, G.; Borgia, A. L.; Ciomei, M. Bioorganic & Medicinal Chemistry 1998, 6, 947-958.
(12) Firsching, A.; Nickel, P.; Mora, P.; Allolio, B. Cancer Research 1995, 55, 4957-4961.
(13) Folkman, M. J.; Shing, Y. 1993. U.S. Pat. No. 5,202, 311.

(14) Liekens, S. et al. Modulation of fibroblast growth factor-2 receptor binding, signaling, and mitogenic activity by heparin-mimicking polysulfonated compounds. *Mol. Pharmacol.* 56, 204-213 (1999).

(15) Liekens, S.; Neyts, J.; Degreve, B.; DeClercq, E. Oncology Research 1997, 9, 173-181.

(16) Presta, M.; Leali, D.; Stabile, H.; Ronca, R.; Camozzi, M.; Coco, L.; Moroni, E.; Liekens, S.; Rusnati, M. Current Pharmaceutical Design 2003, 9, 553-566.

(17) Guan, R., Sun, X. L., Hou, S. J., Wu, P. Y. & Chaikof, E. L. A glycopolymer chaperone for fibroblast growth factor-2. *Bioconjugate Chem.* 15, 145-151 (2004).

(18) Barritault, D.; Caruelle, J. P.; Desgranges, P.; Gautron, J.; Meddahi, A. 1998. U.S. Pat. No. 5,852,003.

(19) Barritault, D.; Caruelle, J. P.; Aamiri, A.; Gautron, J. 2003. U.S. Pat. No. 6,573,251.

(20) Akashi, M.; Sakamoto, N.; Suzuki, K.; Kishida, A. Bioconjugate Chemistry 1996, 7, 393-395.

(21) Bentolila, A.; Vlodaysky, 1.; Haloun, C.; Domb, A. J. Polymers for Advanced Technologies 2000, 11, 377-387.

(22) Porte-Durrieu, M. C.; Aymes-Chodur, C.; Betz, N.; Baquey, C. Journal of Biomedical Materials Research Part A 2000, 52, 119-127.

(23) Benezra, M.; Vogel, T.; Ben-Sasson, S. A.; Panet, A.; Sehayek, E.; Al-Haideiri, M.; Decklbaum, R. J.; Vlodaysky, I. Journal of Cellular Biochemistry 2001, 81, 114-127.

(24) Papy-Garcia, D. B.-C., V.; Rouet, V.; Keros, M.; Klochendler, C.; Tournaire, M.; Barritault, D.; Caruelle, J.; Petit, E. Macromolecules 2005, 38, 4647-4654.

(25) Garcia-Fernandez, L.; Halstenberg, S.; Unger, R. E.; Aguilar, M. R.; Kirkpatrick, C. J.; Roman, J. S. Biomaterials 2010, 31, 7863-7872.

(26) Imamura, T.; Mitsui, Y. Experimental Cell Research 1987, 172, 92-100.

(27) Cariou, R., Harousseau, J. L. & Tobelem, G. Inhibition of human-endothelial cell-proliferation by heparin and steroids. *Cell Biol. Int. Rep.* 12, 1037-1047 (1988).

(28) Ferrao, A. V. & Mason, R. M. The effect of heparin on cell-proliferation and type-I collagen-synthesis by adult human dermal fibroblasts. *Biochim. Biophys. Acta* 1180, 225-230 (1993).

(29) Kolodziej, C. M. et al. Combination of integrin-binding peptide and growth factor promotes cell adhesion on electron-beam-fabricated patterns. *J. Am. Chem. Soc.* 134, 247-255 (2012).

(30) Buechler, Y. J.; Sosnowski, B. A.; Victor, K. D.; Parandoosh, Z.; Bussell, S. J.; Shen, C.; Ryder, M.; Houston, L. L. European Journal of Biochemistry 1995, 234, 706-713.

(31) Lappi, D. A.; Baird, J. A. 1997. U.S. Pat. No. 5,679,637.

(32) Calabresi, P.; Beitz, J. G.; Clark, J. W.; Frackelton, A. R., Jr.; Lappi, D. A.; Baird, A. J. 1995. U.S. Pat. No. 5,478,804.

(33) Kobatake, E.; Takahashi, R.; Mie, M. Bioconjugate Chemistry 2011, 22, 2038-2042.

(34) Griffith, B. R., Allen, B. L., Rapraeger, A. C. & Kiessling, L. L. A polymer scaffold for protein oligomerization. *J. Am. Chem. Soc.* 126, 1608-1609 (2004).

(35) Khondee, S., Olsen, C. M., Zeng, Y. H., Middaugh, C. R. & Berkland, C. Noncovalent PEGylation by polyanion complexation as a means to stabilize keratinocyte growth factor-2 (KGF-2). *Biomacromolecules* 12, 3880-3894 (2011).

(36) DeLong, S. A., Moon, J. J. & West, J. L. Covalently immobilized gradients of bFGF on hydrogel scaffolds for directed cell migration. *Biomaterials* 26, 3227-3234 (2005).

(37) Kang, C. E., Tator, C. H. & Shoichet, M. S. Poly (ethylene glycol) modification enhances penetration of fibroblast growth factor 2 to injured spinal cord tissue from an intrathecal delivery system. *J. Control Release* 144, 25-31 (2010).

(38) Wu, X. L., Zeng, Y., Zheng, Q. & Wu, S. Site-directed PEGylation of human basic fibroblast growth factor. *Protein Expres. Purif.* 48, 24-27 (2006).

(39) Wu, X. L., Xiao, Y., Huang, Z., Xiao, J., Lin, S., Cai, L., Feng, W. & Li, X. Purification and modification by polyethylene glycol of a new human basic fibroblast growth factor mutant-hbFGFSer25,87,92. *J. Chromatogr. A* 1161, 51-55 (2007).

(40) Bhaskaran, S. S.; Sherman, M. R.; Saifer, M. G. P.; Williams, L. D. 2008. U.S. Pat. No. 0,058,246.

(41) Christman, K. L. et al. Nanoscale growth factor patterns by immobilization on a heparin-mimicking polymer. *J. Am. Chem. Soc.* 130, 16585-16591 (2008).

(42) Chiefari, J.; Chong, Y. K.; Ercole, F.; Krstina, J.; Jeffery, J.; Le, T. P. T.; Mayadunne, R. T. A.; Meijs, G. F.; Moad, C. L.; Moad, G.; Rizzardo, E.; Thang, S. H. Macromolecules 1998, 31, 5559-5562.

(43) Le, T.; Moad, G.; Rizzardo, E.; Thang, S. H. 1998. PCT Int. Appl. WO 9801478.

(44) Alconcel, S. N. S.; Grover, G. N.; Matsumoto, N. M.; Maynard, H. D. Australian Journal of Chemistry 2009, 62, 1496-1500.

(45) Wood, M. R.; Duncalf, D. J.; Rannard, S. P.; Perrier, S. *Organic Letters* 2006, 8, 553-556.

(46) Kaddis, C. S.; Lomeli, S. H.; Yin, S.; Berhane, B.; Apostol, M. I.; Kickhoefer, V. A.; Rome, L. H.; Loo, J. A. American Society for Mass Spectrometry 2007, 18, 1206-1216.

(47) Heredia, K. L. et al. Reversible siRNA-polymer conjugates by RAFT polymerization. *Chem. Commun.* 3245-3247 (2008).

(48) Kaufman, S. L.; Skogen, J. W.; Dorman, F. D.; Zarrin, F.; Lewis, K. C. Analytical Chemistry 1996, 68, 1895-1904.

(49) Abuchowski, A. & Davis, F. F. Preparation and properties of polyethylene glycol trypsin adducts. *Biochim. Biophys. Acta* 578, 41-46 (1979).

(50) Hadley, K. B. & Sato, P. H. Catalytic activity of administered guclonolactone oxidase polyethylene-glycol conjugates. *Enzyme* 42, 225-234 (1989).

(51) Alconcel, S. N. S., Baas, A. S. & Maynard, H. D. FDA-approved poly(ethylene glycol)-protein conjugate drugs. *Polymer Chemistry* 2, 1442-1448 (2011).

(52) Keefe, A. J. & Jiang, S. Poly(zwitterionic)protein conjugates offer increased stability without sacrificing binding affinity or bioactivity. *Nat. Chem.* 4, 59-63 (2012).

(53) Mancini, R. J., Lee, J. & Maynard, H. D. Trehalose glycopolymers for stabilization of protein conjugates to environmental stressors. *J. Am. Chem. Soc.* 134, 8474-8479 (2012).

(54) Cardin, A. D. & Weintraub, H. J. R. Molecular modeling of protein-glycosaminoglycan interactions. *Arteriosclerosis* 9, 21-32 (1989).

(55) Slack, J. M. W., Darlington, B. G., Heath, J. K. & Godsave, S. F. Mesoderm induction in early *xenopus* embryos by heparin-binding growth-factors. *Nature* 326, 197-200 (1987).

(56) Abraham, J. A. et al. Nucleotide-sequence of a bovine clone encoding the angiogenic protein, basic fibroblast growth factor. *Science* 233, 545-548 (1986).
(57) Kawai, K., Suzuki, S., Tabata, Y., Ikada, Y. & Nishimura, Y. Accelerated tissue regeneration through incorporation of basic fibroblast growth factor-impregnated gelatin microspheres into artificial dermis. *Biomaterials* 21, 489-499 (2000).
(58) Canalis, E., Centrella, M. & McCarthy, T. Effects of basic fibroblasat growth-factor on bone-formation invitro. *J. Clin. Invest.* 81, 1572-1577 (1988).
(59) Timmer, M. et al. Fibroblast growth factor (FGF)-2 and FGF receptor 3 are required for the development of the substantia nigra, and FGF-2 plays a crucial role for the rescue of dopaminergic neurons after 6-hydroxydopamine lesion. *J. Neurosci.* 27, 459-471 (2007).
(60) Levenstein, M. E. et al. Basic fibroblast growth factor support of human embryonic stem cell self-renewal. *Stem Cells* 24, 568-574 (2006).
(61) Barrientos, S., Stojadinovic, O., Golinko, M. S., Brem, H. & Tomic-Canic, M. Growth factors and cytokines in wound healing. *Wound Repair Regen.* 16, 585-601 (2008).
(61) Shipley, G. D., Keeble, W. W., Hendrickson, J. E., Coffey, R. J. & Pittelkow, M. R. Growth of normal human keratinocytes and fibroblasts in serum-free medium is stimulated by acidic and basic fibroblast growth-factor. *J. Cell Physiol.* 138, 511-518 (1989).
(62) Pittelkow, M. R. & Shipley, G. D. Serum-free culture of normal human melanocytes—growth-kinetics and growth-factor requirements. *J. Cell Physiol.* 140, 565-576 (1989).
(63) Chang, C. W., Bays, E., Tao, L., Alconcel, S. N. S. & Maynard, H. D. Differences in cytotoxicity of poly(PEGA)s synthesized by reversible addition-fragmentation chain transfer polymerization. *Chem. Commun.* 3580-3582 (2009).
(64) Tao, L. et al. Synthesis of maleimide-end-functionalized star polymers and multimeric protein-polymer conjugates. *Macromolecules* 42, 8028-8033 (2009).
(65) Loo, J. A. et al. Electrospray ionization mass spectrometry and ion mobility analysis of the 20S proteasome complex. *J. Am. Soc. Mass Spectr.* 16, 998-1008 (2005).
(66) Gethin, G. The significance of surface pH in chronic wounds. *Wounds UK* 3, 52-56 (2007).
(67) Mohammadi, M. et al. Structures of the tyrosine kinase domain of fibroblast growth factor receptor in complex with inhibitors. *Science* 276, 955-960 (1997).
(68) Johnson, D. E., Lu, J., Chen, H., Werner, S. & Williams, L. T. The human fibroblast growth-factor receptor genes—a common structural arrangement underlies the mechanisms for generating receptor forms that differ in their 3rd immunoglobulin domain, *Mol. Cell Biol.* 11, 4627-4634 (1991).
(69) Mohammadi, M. et al. Crystal structure of an angiogenesis inhibitor bound to the FGF receptor tyrosine kinase domain. *Embo Journal* 17, 5896-5904 (1998).
(70) Schlessinger, J. et al. Crystal structure of a ternary FGF-FGFR-heparin complex reveals a dual role for heparin in FGFR binding and dimerization. *Molecular Cell* 6, 743-750 (2000).
(71) Ornitz, D. M. & Leder, P. Ligand specificity and heparin dependence of fibroblast growth-factor receptor-1 and receptor-3. *J. Biol. Chem.* 267, 16305-16311 (1992).
(72) Fishburn, C. S. The pharmacology of PEGylation: balancing PD with PK to generate novel therapeutics. *J. Pharm. Sci.* 97, 4167-4183 (2008).
(73) Pasut, G. & Veronese, F. M. Polymer-drug conjugation, recent achievements and general strategies. *Prog. Polym. Sci.* 32, 933-961 (2007).
(74) Faham, S., Hileman, R. E., Fromm, J. R., Linhardt, R. J. & Rees, D. C. Heparin structure and interactions with basic fibroblast growth factor. *Science* 271, 1116-1120 (1996).
(75) Murthy, N., Campbell, J., Fausto, N., Hoffman, A. S. & Stayton, P. S. Bioinspired pH-responsive polymers for the intracellular delivery of biomolecular drugs. *Bioconjugate Chem.* 14, 412-419 (2003).
(76) Saucy, D. A., Ude, S., Lenggoro, I. W. & de la Mora, J. F. Mass analysis of water-soluble polymers by mobility measurement of charge-reduced ions generated by electrosprays. *Anal. Chem.* 76, 1045-1053 (2004).
(77) Gospodarowicz, D. Fibroblast growth factor and its involvement in developmental processes. *Current Topics in Developmental Biology* 24, 57-93 (1990).
(78) Yayon, A. K., Michael; Esko, Jeffrey D.; Leder, Philip; Ornitz, David Cell Surface, Heparin-like Molecules are Required for Binding of Basic Fibrobast Growth Factor to Its High Affinity Receptor. *Cell* 64, 841-848 (1991).
(79) Plotnikov, A. N. S., J.; Hubbard, S. R.; Mohammadi, M. Structural Basis for FGF Receptor Dimerization and Activation. *Cell* 98, 641-650 (1999).
(80) Ornitz, D. M. Y., A.; Flanagan, J. G.; Svahn, C. M.; Levi, E.; Leder, P. Heparin is required for cell-free binding of bFGF to a soluble receptor and for mitogenesis in whole cells. *Molecular Cell Biology* 12, 240-247 (1992).
(81) Mori, H., Kudo, E., Saito, Y., Onuma, A. & Morishima, M. RAFT Polymerization of Vinyl Sulfonate Esters for the Controlled Synthesis of Poly(lithium vinyl sulfonate) and Sulfonated Block Copolymers. *Macromolecules* 43, 7021-7032 (2010).
(82) Seely, J. E. & Richey, C. W. Use of ion-exchange chromatography and hydrophobic interaction chromatography in the preparation and recovery of polyethylene glycol-linked proteins. *Journal of Chromatography A* 908, 235-241 (2001).
(83) Kolodziej, C. M. et al. Combination of Integrin-Binding Peptide and Growth Factor Promotes Cell Adhesion on Electron-Beam-Fabricated Patterns. *Journal of the American Chemical Society* 134, 247-255 (2011).
(84) Lutolf, M. P. & Hubbell, J. A. Synthesis and Physicochemical Characterization of End-Linked Poly(ethylene glycol)-co-peptide Hydrogels Formed by Michael-Type Addition. *Biomacromolecules* 4, 713-722 (2003).
(85) Spivak-Kroizman, T. L., M. A.; Dikic, I.; Ladbury, J. E.; Pinchasi, D.; Huang, J.; Jaye, M.; Crumley, G.; Schlessinger, J.; Lax, I. Heparin-induced oligomerization of FGF molecules is responsible for FGF receptor dimerization, activation, and cell proliferation. *Cell* 79, 1015-1024 (1994).

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

We claim:

1. A conjugate comprising a heparin mimicking polymer and a biologic agent, wherein the heparin mimicking polymer comprises a reactive group that reacts with a moiety in a target protein to form a covalent attachment of the polymer to the target protein.

2. The conjugate of claim 1, wherein the biologic agent is a member of the fibroblast growth factor family.

3. The conjugate of claim 1, wherein the biologic agent is selected from the group consisting of a fibroblast growth factor, a keratinocyte growth factor (KGF), a vascular endothelial growth factor (VEGF), a platelet derived growth factor (PDGF), a placental growth factor (PIGF), a hepatocyte growth factor (HGF), an insulin-like growth factor-binding protein, a TGF-β family members, pleiotrophin (PLN), anti-thrombin III (AT III), a secretory leukocyte protease inhibitor (SLKI), a C1 esterase inhibitor (C1 INH), a valosin-containing protein (VCP), platelet factor 4 (PF-4), interleukin 8 (IL-8), stromal cell-derived factor α (SDF-1α), interferon-gamma (INF-gamma), macrophage inflammatory protein-1 (MIP-1), monocyte chemoattractant protein-1 (MCP-1), interferon-γ-inducible protein-10 (IP-10), an Annexin, apolipoprotein E (ApoE), apolipoprotein B (ApoB), apolipoprotein A-V (ApoA-V), human immunodeficiency virus type-1 gp120 (HIV-1 gp120), cyclophilin A, HIV-Tat transactivating factor (Tat), herpes simplex virus (HSV), dengue virus envelop protein, malaria CS protein, lipoprotein lipase, hepatic lipase, selectins, vitronectin, fibronectin, laminin, heparin-binding growth associated molecule (HB-GAM), adaptor protein (AP), and a combination thereof.

4. The conjugate of claim 1, wherein the moiety in the target protein is selected from the group consisting of a free thiol group, an amine group, an aldehyde group, a carboxyl group, a hydroxyl group, a ketone group, an oxo group, an azide group, an alkyne group, and a combination thereof.

5. The conjugate of claim 1, wherein the moiety in the target protein is present naturally in the target protein or added by chemical or biological modification.

6. The conjugate of claim 1, wherein the heparin mimicking polymer is selected from the group consisting of poly(styrene sulfonate) (pSS), poly(styrene sulfonate)-co-poly(polyethylene glycol methacrylate) (pSS-co-PEGMA), poly(sodium vinyl sulfonic acid) (pVS), and a combination thereof.

7. The conjugate of claim 3, comprising a plurality of bFGFs attached to one or more heparin mimicking polymer.

8. A method of treating or ameliorating a disorder, comprising:
administering to a subject an effective amount of the conjugate of claim 1, such that the disease is treated or ameliorated.

9. The method of claim 8, wherein the polymer is in the form of a conjugate comprising the polymer and a biologic agent, wherein the heparin mimicking polymer comprises a reactive group that reacts with a moiety in a target protein to form a covalent attachment of the polymer to the target protein.

10. The method of claim 8, wherein the biologic agent is selected from the group consisting of a fibroblast growth factor, a keratinocyte growth factor (KGF), a vascular endothelial growth factor (VEGF), a platelet derived growth factor (PDGF), a placental growth factor (PIGF), a hepatocyte growth factor (HGF), an insulin-like growth factor-binding protein, a TGF-β family members, pleiotrophin (PLN), anti-thrombin III (AT III), a secretory leukocyte protease inhibitor (SLKI), a C1 esterase inhibitor (C1 INH), a valosin-containing protein (VCP), platelet factor 4 (PF-4), interleukin 8 (IL-8), stromal cell-derived factor α (SDF-1α), interferon-gamma (INF-gamma), macrophage inflammatory protein-1 (MIP-1), monocyte chemoattractant protein-1 (MCP-1), interferon-γ-inducible protein-10 (IP-10), an Annexin, apolipoprotein E (ApoE), apolipoprotein B (ApoB), apolipoprotein A-V (ApoA-V), human immunodeficiency virus type-1 gp120 (HIV-1 gp120), cyclophilin A, HIV-Tat transactivating factor (Tat), herpes simplex virus (HSV), dengue virus envelop protein, malaria CS protein, lipoprotein lipase, hepatic lipase, selectins, vitronectin, fibronectin, laminin, heparin-binding growth associated molecule (HB-GAM), adaptor protein (AP), and a combination thereof.

11. The method of claim 8, wherein the moiety in the target protein is selected from the group consisting of a free thiol group, an amine group, an aldehyde group, a carboxyl group, a hydroxyl group, a ketone group, an oxo group, an azide group, an alkyne group, and a combination thereof.

12. The method of claim 10, wherein the conjugate comprises a plurality of bFGFs attached to one or more heparin mimicking polymer.

* * * * *

UNITED STATES PATENT AND TRADEMARK OFFICE
CERTIFICATE OF CORRECTION

PATENT NO. : 9,925,270 B2
APPLICATION NO. : 14/361167
DATED : March 27, 2018
INVENTOR(S) : Heather D. Maynard et al.

Page 1 of 1

It is certified that error appears in the above-identified patent and that said Letters Patent is hereby corrected as shown below:

On the Title Page

Title, Item (54), "BFGF" should be --bFGF--.

In the Specification

Column 1, Line 1, "BFGF" should be --bFGF--.

Column 5, Line 44, "amination" should be --amidation--.

Column 32, Line 45, "Vlodaysky" should be --Vlodavsky--.

Column 33, Line 20, "Vlodaysky" should be --Vlodavsky--.

Column 33, Lines 26-27, "Vlodaysky" should be --Vlodavsky--.

Signed and Sealed this
Nineteenth Day of March, 2019

Andrei Iancu
*Director of the United States Patent and Trademark Office*